United States Patent [19]

Masure et al.

[11] Patent Number: 5,928,900

[45] Date of Patent: Jul. 27, 1999

[54] BACTERIAL EXPORTED PROTEINS AND ACELLULAR VACCINES BASED THEREON

[75] Inventors: H. Robert Masure; Barbara J. Pearce; Elaine Tuomanen, all of New York, N.Y.

[73] Assignee: The Rockefeller University, New York, N.Y.

[21] Appl. No.: 08/245,511

[22] Filed: May 18, 1994

Related U.S. Application Data

[63] Continuation-in-part of application No. 08/116,541, Sep. 1, 1993, abandoned.

[51] Int. Cl.⁶ .......................... C12P 21/06; A61K 39/00; A61K 39/02; C07K 1/00
[52] U.S. Cl. .................. 435/69.3; 424/185.1; 424/190.1; 424/244.1; 530/350
[58] Field of Search .................. 530/350; 424/185.1, 424/190.1, 244.1; 435/69.3

[56] References Cited

FOREIGN PATENT DOCUMENTS

| 274425 | 7/1988 | European Pat. Off. |
|---|---|---|
| WO 90/06951 | 6/1990 | WIPO. |
| WO 92/14488 | 9/1992 | WIPO. |
| WO 93/10238 | 5/1993 | WIPO. |
| WO 93/14198 | 7/1993 | WIPO. |
| 274425 | 12/1993 | WIPO .......................... C12N 15/53 |

OTHER PUBLICATIONS

Harlow et al. Antibodies: A Laboratory Manual, Cold Spring Harbor Laboratory, 1988.
Pearce el al. Molecular Microbiology 9(5):1037–50, 1993.
Yother et al. Journal of Bacteriology 174(2): 610–618, 1992.
Talkington et al. Microbial Pathogenesis 13: 343–355, 1992.
Andersson et al. Microbial Pathogenesis 4: 267–78, 1988.
Pearce et al., 1994, Molec. Microbiol. 12:881–92.
Geelen et al., 1993, Infect. Immun. 61:1538–1543.
Park, 1993, J Bacteriol. 175:7–11.
Ruhfel et al., 1993, J. Bacteriol. 175:5253–59.
Tanimoto et al., 1993 J. Bacteriol. 175:5260–4.
Pearce et al., 1993, Mol. Microbiol. 9:1037–50.
Trombe, 1993, J. Gen. Microbiol. 139:433–9.
Wang et al., 1993, Proc. Natl. Acad. Sci. USA 90:4156–60.
Hoepelman and Tuomanen, 1992, Infect. Immun. 60:1729–33.
Jenkinson, 1992, Infect. Immun. 60:1225–8.
Martin et al., 1992, EMBO J. 11:3831–6.
Martin et al., 1992, J. Bacteriol. 174:4517–4523.
Pearce and Masure, 1992, Abstr. Gen. Meet. Am. Soc. Microbiol. 92:127, D–188.
Perez–Martinez et al., 1992, Mol. Gen. Genet. 234:401–11.
Saier and Reizer, 1992, J. Bacteriol. 174:1433–1448.
Schmid and Linder, 1992, Mol. Microbiol. 6:283–92.
Squires and Squires, 1992, J. Bacteriol. 174:1081–5.
Taha et al., 1992, J. Bacteriol. 174:5978–81.
Talkington et al., 1992, Microb. Pathog. 13:343–55.
Tang et al., 1992, Nature 356:152–54.
Yother et al., 1992, J. Bacteriol. 174:610–8.
Gonzy–Tréboul et al., 1991, Mol. Microbiol. 5:1241–9.
Payne and Jackson, 1991, J. Bacteriol. 173:2278–82.
Snavely et al., 1991, J. Biol. Chem. 266:815–23.
Toone et al., 1991, J. Bacteriol. 173:3291–3302.
Alloing et al., 1990, Mol. Microbiol. 4:633–44.
Gottesman et al., 1990, Proc. Natl. Acad. Sci. USA 87:3513–7.
Holmberg et al., 1990, J. Gen. Microbiol. 136:2367–75.
Alloing et al., 1989, Gene– 76:363–8.
Guitierrez and Devedjian, 1989, Nucleic Acid Res. 17:3999.
Andersson et al., 1988, Microb. Pathogen. 4:267–278.
Chen and Morrison, 1988, Gene 64:155–64.
Gilson et al., 1988, EMBO J. 7:3971–4.
Glaser et al., 1988, Mol. Microbiol. 2:19–30.
Glaser et al., 1988, EMBO J. 7:3997–4004.
Smith et al., 1988, Gene 70:351–61.
Taha et al., 1988, EMBO J. 7:4367–78.
Smith et al., 1987, J. Bacteriol. 169:3321–28.
Hoffman and Wright, 1985, Proc. Natl. Acad. Sci. U.S.A. 82:5107–11.
Manoil and Beckwith, 1985, Proc. Natl. Acad. Sci. U.S.A. 82:8129–33.
Beachey, 1981, J. Inf. Diseases 143:325.
Tiraby and Fox, 1973, Proc. Natl. Acad. Sci. U.S.A. 70:3541–3545.

*Primary Examiner*—James C. Housel
*Assistant Examiner*—V. Ryan
*Attorney, Agent, or Firm*—Klauber & Jackson

[57] ABSTRACT

The present invention relates to the identification of Gram positive bacterial exported proteins, and the genes encoding such proteins. In particular, the invention relates to adhesion associated exported proteins, and to antigens common to many or all strains of a species of Gram positive bacterium. The invention also relates to acellular vaccines to provide protection from Gram positive bacterial infection using such genes or such proteins, and to antibodies against such proteins for use in diagnosis and passive immune therapy. In specific embodiments, fragments of ten genes encoding exported proteins of *S. pneumoniae* are disclosed, and the functional activity of some of these proteins in adherence is demonstrated.

2 Claims, 29 Drawing Sheets

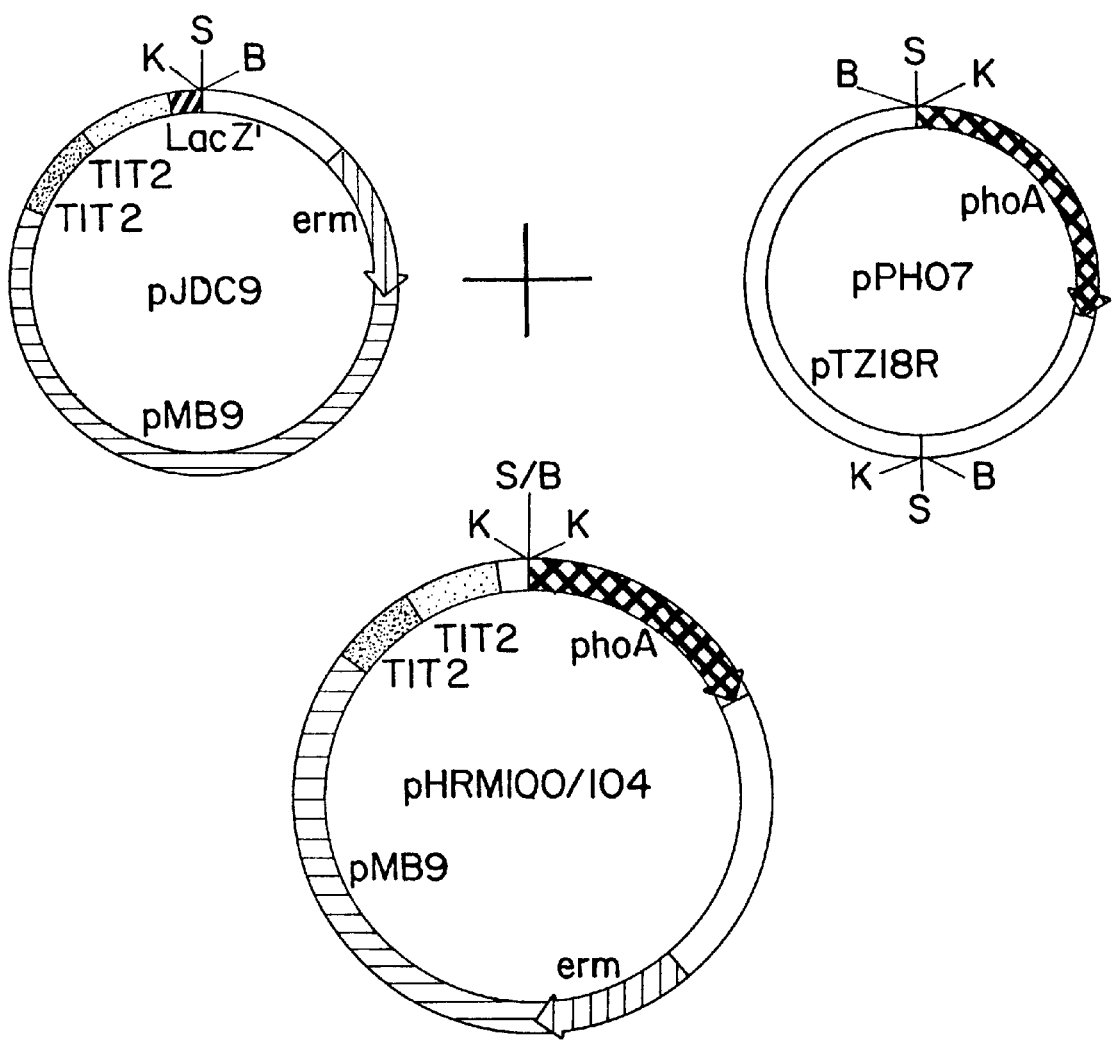
FIG. IA

FIG. 4

```
Exp1    1 DRTAYASQLN GQTGASKILR NLFVPPTEVQ ADGKNFGDMV KEKLVTYGDE WKDVNLADSQ  60
       61 DGLYNPEKAK AEFAKAKSAL QAEGVTFPIH LDMPVDQTAT TKVQRVQSMK QSLEATLGAD 120
      121 NVIIDIQQLQ KDEVNNITYF AENAAGEDWD LSDNVGWGPD FAD 163

Exp2    1 TTGMDVYTNV DQEAQKHLWD IVNTDEYVAY PDDELQVAST IVDVSNGKVI AQLGARHQSS  60
       61 NVSFGINQAV ETNRDWG 77

Exp3    1 DPLSINQQGN DRGRQYRTGI YYQDEADLPA IYTVVQEQER MLGRKIAVEV EQLRHYILAE  60
       61 DYHQDYLRKN PSGYCHIDVT DADKPLIDAA NYEKPSQEVL KASLSEESYR VTQEAATEAP 120
      121 FTNAYDQTFE EGIYVDITTG EPLFFAKDKF ASGCGWPSFS RPISKELIHY YKD 173

Exp4    1 SNAGTGKTEA SVGFGAAREG RTNSVLGELG NFFSPEFMNR FDGIIEFKAL SKDNLLQIVE  60
       61 LMLADVNKRL SSNNIRLDVT DKVKEKLVDL GYD 93

Exp5    1 VKVDDGSQAV NIINLLGGRV NIVDVDACMT RLRVTVKDAD KVGNAEQWKA EGAMGLVMKG  60
       61 QGVQAIYGPK ADILKSDIQD ILDSGEIIPE TLPSQMTEVQ QNTVHFKD 108

Exp6    1 SQPVSFDTGL GDGRMVFVLP RENKTYFGTT DTDYTGDLEH PKVTQEDVDY LLGIVNNRFP  60
       61 ESNITIDDIE SSWAGLRPLI AGNSASDYNG GNNGTIRDES FDNLIATVES YLSKEKTRED 120
      121 VESAVSKLES STSEKHLD 139

Exp7    1 TASEFELGTP LSQEKLDHHK PQKPSDIQAL ALLEILDPIR EGAAEFLDYL RSQEVGLKII  60
       61 SGDNPVTVSS IAQKAGFADY H 71

Exp8    1 RLSWVTPGFS QSRRCKTTAS EFELGTLRKN IGLVLQEPFL YHGTIKSNIA MYQEISDEQV  60
       61 QAAAAFVDAD SFIQELPQGY DSPVSERGSS FSTGQR 96

Exp9 a   1 SSIEKQIKAL KSGAHIVVGT PGRLLDLIKR KALKLQDIET LILDEADEML NMGFLEDIEA  60
Exp9 b  61 IISRVPENRQ TLLFSATMPD AIKRIGVQFM KAPEHVRIAA KELTTELVDQ YYI 115
         1 AFVFGRTKRR VDELTRGLKI RGFRAEGIHG DLDQNKRLRV LRDFKNGNLD VLVATDVAAR  60
        61 GLDISGVTHV YNVDIPQD 78
```

FIG. 5A

```
                                                                                  %ID   %SIM
Exp1    1   DRTAYASQLNGQTGASKILRNLFVPPTFVQADGKNFGDMVKEKLVTYGDEWKDVNLADSQDGLYNPEKAKAEFAKAKSALQAEGV  85
            DR+AY++Q+NG  GA+  +RNLFV P FV A  K FGD+V   L +YGDEWK VNLAD+QDGL+N++KAKAEF KAK AL+A+GV       60    79
AmiA  348   DRSAYSAQINGKGAALAVRNLFVKPDFVSAGEKTFGDLVAAQLPAYGDEWKGVNLADGQDGLFNADKAKAEFRKAKALEADGV 433

Exp1   86   TFPIHLDMPVDQTATTKVQRVQSMKQSLEATLGADNVIIDIQQLQKDEVNNITYFAENAAGEDWDLSDNVGWGPDFAD 163
            FPIHLD+PVDQ++    R+QS KQS+E+ LG  +NV++DIQQ+   DE  NITY+A  NA++EDWD+S  V+WGPD+ D
AmiA  434   QFPIHLDVPVDQASKNYISRIQSFKQSVETVLGVENVVDIQQMTSDEFLNITYAANASSEDWDVSGGVSWGPDYQD 510
```

FIG. 5B

```
                                                                                  %ID   %SIM
Exp2    1   TTGMDVYTNVDQEAQKHLWDIYNTDEYVAYPDDELQVASTIVDVSNGKVIAQLGARHQSSNVSFGINQAVETNRDWG  77
            TTGMDVYTNVDQEAQKHLWDIYNTDEYVAYPDDELQVASTIVDVSNGKVIAQLGARHQSSNVSFGINQAVETNRDWG      100   100
PonA  353   TTGMDVYTNVDQEAQKHLWDIYNTDEYVAYPDDELQVASTIVDVSNGKVIAQLGARHQSSNVSFGINQAVETNRDWG 369
```

FIG. 5C

```
                                                                                  %ID   %SIM
Exp3    1   DPLSINQQGNDRGRQYRTGIYYQDEADLPAIYTVVQEQERMLGRKIAVEVEQLRHYILAEDYHQDYLRKNPSGYCHIDVTDADKPL  86
            DP S+N QGND G QYR+G+YY D A+  I  +   +++     + VE E L+++   AE+YHQDYL KNP+GYCHID+  AD PL    40    64
PilB  274   DPTSLNKQGNDTGTQYRSGVYYTDPAEKAVIAAALKRSQQKYQLPLVVENEPLKNFYDAEEYHQDYLIKNPNGYCHIDIRKADEPL 359

Exp3   87   IDAANYEKPSQEVLKASLSEESYRVT 112
            +  A   +PSQE+L ++ ++  +R+T                                                              nd    nd
PilB  360   PGKTKAAPCGQRLRRGRIKNRVTPNSNAPDRRAIPSD 397

Exp3  113   QEAATERFTNAYDCTFEEGIYVDITTGEPLFFAKDKFASGGGWPSFSRPI 163
            Q++ATE  F++  YD+  F  GIYVD+  +GEPLF  + DK+  SGGGW+SF+R+PI                               60    82
pilB  398   QNSATEYAFSEEYDHLFKPGIYDVVSGEPLFSSADKYDSGGGWPSFTRPI 448
```

FIG. 5D

```
                                                                                  %ID   %SIM
Exp4   25   VLGELGNFFSPEEMNRFDGIIEFKALSKDNLLQIVELMLADVNKRLSSNNIRLDVTTDKVKEKLVDLGYD  93
            V  EL   +F  +F PEF+NR D + F+ L+K ++ +I  ++ML  +V  RL  ++I  L+VT++  +++VD GY+         41    74
Cd4B  790   VTEELKQYFRPEFLNRLDEMIVFRQLTKLEVEKEIADIMLKEVTERLKVKEIELQVTERSFRDRVVDEGYN 858
```

FIG. 5E

```
                                                                              %ID  %SIM
                                                                              41   65
Exp5    4 DDGSQAVNIINLLGRVNIVDVDAC+TRLRVTVKDADKVGNAEQWKAEGAMGLVMKGQGVQAIYGP+ADILKSDIQDIDSGEII  88
          + G  + +I+  +G + NI  +DAC+TRLRVTV+D  KV +  ++ K  GA G++  +QAI+GP++D LK+++QDI+ +
PtsG  189 EAGDLPYEILQAMGDQENIKHLDACITRLRVTVNDQKKV DKDRLKQLGASGVLEVGNNIQAIFGPRSDGLKTQMDDIAGRKPR   274

Exp5   89 PETLPSQMTEVQQ  101
          PE  S   EV Q
PtsG  275 PEPKTSAQEEVGQ  285
```

FIG. 5F

```
                                                                              %ID  %SIM
                                                                              68   78
Exp6   12 DGRMVFVLPRENKTYFGTTDTDYTGDLEHPKVTQEDVDYLLGIVNNRFPESNITIDDIESSWAGLRPLI  80
          DGRM/F +PRE KTY GTTDT Y    LEHP++T ED DY++    +N  FPE NIT +DIESSWAGLRPLI
GlpD  278 DGRMVFAIPRSGKTVGTTDTVYKEALEHPRMTTEDRDYVIKSINYMFPELNITANDIESSWAGLRPLI   346
```

FIG. 5G

```
                                                                              %ID  %SIM
                                                                              36   68
Exp7   31 ALLEILDPVREGAAETLDYLRSQEVGLKIISGVNPVTVSSI   71
          ++L  LDP +E+A+ ++ LR   V++K+++G NPV  + I
MgtB  548 GMLTFLDPPKESAGKAIAALRDNGVAVKVLTGDNPVVTARI   588
```

FIG. 5H

```
                                                                              %ID  %SIM
                                                                              40   67
Exp8   25 GTLRKNIGLVLQEPFLYKGTIKSNIAMYQEISDE      QVQAAAAFVDADSFIQELPQGYDSPVSERGSSFSTGQR  96
          ++LR+ +G+VLQE+ L++ ++ NIA-         +V AAA  A  F  +LP+GYD+  ++E G + S GQR
CyaB  542 ASLRRQLGVVLQESTLFNRSYRDNIALTRPGASMH     EVVAAARLAGAHEFICQLPEGVDTMLGENGVGLSGGQR   614
```

FIG. 5I

```
                                                                              %ID  %SIM
                                                                              61   84
Exp9    6 QIKALKSGAHIVVGTPGRLLDLIKRKALKLQDIETLILDEADEMLNMGFLEDIEAIISRVPENRQTLLFSATMPDAIKRIGVQFMK  91
          Q++AL+ G++IVVGTPGRLLD +KR +L L  +  L+LDEADEML MGF +ED+E+I++++PE +QT LFSATMP+AI+RI  +FMK
DeaD  135 QLRALRQGPQIVVGTPGRLLDHLKRGTLDLSKLSGLVLDEADEMLRMGFIEDVETIMAQIPEGHQTALFSATMPEAIRRITRRSMK   220

%ID  %SIM
                                                                              34   67
Exp9    1 AFVFGRTKRRVDELTRGLKIRGFRAEGIHGDLDQNKRLRVLRDFKNGNLDVLVATDVAARGLDISGVTHVVNYDIPQD  78
          A +F RTK    E++ +L  G+ + +++GD++Q  R + L   K+G LD++ATDVAARGLD+ ++ V NYDIP D
DeaD  265 AIIFVRTKNATLEVAEALERNGYNSAALNGDMNQALRSCTLERLKDGRLDILIATDVAARGLDVERISLVVNYDIPMD   342
```

FIG. 10

```
              10                30                50
CCAGATGCGCTTCGAAAGCCAACGTGTTCTCTCCACCGAGAATTTGACCGCCTCTCAA
ProAspAlaLeuArgLysProThrCysSerLeuHisArgGluPheAspArgLeuSerGln
                      70                90               110
AGGAGCCATAAACGATTTTGAAGGCGTTGAATCGTATCATGAATCGTATCATGAATACAACAATACGACAA
ArgSerHisAsnAspPheGluGlyValGluSerTyrHisGluTyrThrThrIleArgGln
                     130               150               170
ACTCTCACCATATCCTCATATGTAACAGAAGGATTACCAATTTTAGATTATCAATAATT
ThrLeuThrIleSerSerTyrValThrGluGlyLeuProIlePheArgLeuSerIleIle
                     190               210               230
GTCCCTGTAAAGAGTCTATGGTCTCTGTGGAATGTAGGAAATTTCTTACGTAGTTTACCAT
ValProValLysSerLeuTrpSerValGluCysArgLysPheSerTyrValValTyrHis
                     250
AGTCAAGATC
SerGlnAsp
```

FIG. 11A

```
         10                    30                     50
ggtgtacttgcagcatgtctctggatcaggttcaaggtgctaaaggtgagaagacattctca
GlyValLeuAlaAlaCysSerGlySerGlySerSerAlaLysGlyGluLysThrPheSer
         70                                          90                                          110 tacatttatgagacagacccctgataacctcaactatttgacaactgctaaggctgcgaca
TyrIleTyrGluThrAspProAspAsnLeuAsnTyrLeuThrThrAlaLysAlaAlaThr
         130                   150                    170 gcaaatattaccagtaacgtggttgatggtttgatggtttgctagaaaatgatcgctacgggaacttt
AlaAsnIleThrSerAsnValValAspGlyLeuLeuGluAsnAspArgTyrGlyAsnPhe
         190                   210                    230 gtgccgtctatggctgaggattggtctgtatccaaggatggattgacttacacttatact
ValProSerMetAlaGluAspTrpSerValSerLysAspGlyLeuThrTyrThrTyrThr
         250                   270                    290 atccgtaaggatgcaaaatgtatactctgaaggtgaagaatacgcggcagtcaaagct
IleArgLysAspAlaLysTrpTyrThrSerGluGlyGluTyrAlaAlaValLysAla
         310                   330                    350 caagactttgtaacagaggactaaaatatgctgataaaaatcagatgctctttaccct
GlnAspPheValThrGlyLeuLysTyrAlaAlaAspLysLysSerAspAlaLeuTyrPro
         370                   390                    410 gttcaagaatcaatcaaaggttggatgcctatgtaaaagggaaatcaaagatttctca
ValGlnGluSerIleLysGlyLeuAspAlaTyrValLysGlyLysGluIleLysAspPheSer
         430                   450                    470 caagtaggaattaaggctctggatgaacagacagttcagtacacctttgaacaaaccagaa
GlnValGlyIleLysAlaLeuAspGluGlnThrValGlnThrTyrThrLeuAsnLysProGlu
         490                   510                    530 agcttctggaattctaagacaaccatgggtgtgcttgcgccagttaatgaagagttttg
SerPheTrpAsnSerLysThrThrMetGlyValLeuAlaProValAsnGluGluPheLeu
         550                   570                    590 aattcaaaaggagatgattttgccaagatccacgatccaagtagtctcttgtataacggt
AsnSerLysGlyAspAspPheAlaLysAlaThrAspProSerLeuLeuTyrAsnGly
```

FIG. 11B

```
       610                         630                         650
ccttatttgttgaaatccattgtgaccaaatcctctgttgaatttgcgaaaaatccgaac
ProTyrLeuLeuLysSerIleValThrLysSerSerValGluPheAlaLysAsnProAsn
                         670                         690                         710 tactgggataaggacaatgtgcatattgacaaagttaaatgtcattctgggatggtcaa
TyrTrpAspLysAspAsnValHisIleAspLysValLysLeuSerPheTrpAspGlyGln
                         730                         750                         770 gataccagcaaacctgcagaaacttaaagatggtagccttacagcagctcgtctctat
AspThrSerLysProAlaGluAsnPheLysAspGlySerLeuThrAlaAlaArgLeuTyr
                         790                         810                         830 ccaacaagtgcaagtttcgcagagcttgagagagtatgaaggacaatattgtctatact
ProThrSerAlaSerPheAlaGluLeuGluGluValMetLysAspAsnIleValTyrThr
                         850                         870                         890 caacaagactctattacgtatcggtacaaatattgaccgtcagtcctataaatac
GlnGlnAspSerIleThrTyrLeuValGlyThrAsnIleAspArgGlnSerTyrLysTyr
                         910                         930                         950 acatctaagaccagcgatgaacaaaaggcatcgactaaaaaggctctcttaaacaaggat
ThrSerLysThrSerAspGluGlnLysAlaSerThrLysLysAlaLeuLeuAsnLysAsp
                         970                         990                         1010 ttccgtcaggctattgcctttgttgatcgtacagcctatgcctctcagttgaatgga
PheArgGlnAlaIleAlaPheGlyPheAspArgThrAlaTyrAlaSerGlnLeuAsnGly
                         1030                        1050                        1070 caaactggagcaagtaaaatcttgctaatctctcttgtgccaccaacattgttcaagca
GlnThrGlyAlaSerLysIleLeuLeuArgAsnLeuPheValProProThrPheValGlnAla
                         1090                        1110                        1130 gatggtaaaactttggcgatatggtcaaagagaaattggtcacttatggggatgaatgg
AspGlyLysAsnPheGlyAspMetValLysGluLysLeuValThrTyrGlyAspGluTrp
                         1150                        1170                        1190 aaggatgttaatcttgcagattctcaggatggtctttacaatccagaaaagccaaggct
LysAspValAsnLeuAlaAspSerGlnAspGlyLeuTyrAsnProGluLysAlaLysAla
```

FIG. IIC

```
                                                        1230                                                        1250
gaatttgctaaagctaaatcagcccttacaagcagaaggtgtgacattcccaattcattg
GluPheAlaLysAlaLysSerAlaLeuGlnAlaGluGlyValThrPheProIleHisLeu
   1270                                                       1290                                                       1310
gatatgccagttgaccagacagcaactacaaaagttcagcgcgtccaatctatgaaacaa
AspMetProValAspGlnThrAlaThrThrLysValGlnArgValGlnSerMetLysGln
         1330                                                      1350                                                      1370
tccttggaagcaacttTaggagctgataatgtcattattgatattcaacaactacaaaaa
SerLeuGluAlaThrLeuGlyAlaAspAsnValIleIleAspIleGlnGlnLeuGlnLys
               1390                                                    1410                                                    1430
gacgaagtaaacaatattacatatttgctgaaaatgctgctggcgaagactggaagatta
AspGluValAsnAsnIleThrTyrPheAlaGluAsnAlaAlaGlyGluAspTrpAspLeu
                     1450                                              1470                                              1490
tcagataatgtcggttggggtccagactttgccgatccatcaacctacctgatatcatc
SerAspAsnValGlyTrpGlyProAspPheAlaAspProSerThrTyrLeuAspIleIle
                           1510                                        1530                                        1550
aaaccatctgtaggagaaagtactaaaacatatttagggtttgactcagggaagataat
LysProSerValGlyGluSerThrLysThrTyrLeuGlyPheAspSerGlyGluAspAsn
                                 1570                                  1590                                  1610
gtagctgctaaaaagtaggtctatatgactacgaaaaattggttactgaggctggtgat
ValAlaAlaLysLysValGlyLeuTyrAspTyrGluLysLeuValThrGluAlaGlyAsp
```

FIG. IID

```
                       1630                     1650                     1670
gagactacagatgttgctaaacgctatgataatacgctgcagcccaagcttggttgaca
GluThrThrAspValAlaLysArgTyrAspLysTyrAlaAlaGlnAlaTrpLeuThr
                       1690                     1710                     1730
gatagtgctttgattattccaactactctcgtacagggcgtccaatcttgtctaagatg
AspSerAlaLeuIleIleProThrThrSerArgThrGlyArgProIleLeuSerLysMet
                       1750                     1770                     1790
gtaccattacaataccatttgcattgtcaggaaataaaggtacaagtgaaccagtcttg
ValProPheThrIleProPheAlaLeuSerGlyAsnLysGlyThrSerGluProValLeu
                       1810                     1830                     1850
tataaatacttggaacttcaagacaaggcagtcactgtagatgaataccaaaagctcag
TyrLysTyrLeuGluLeuGlnAspLysAlaValThrValAspGluTyrGlnLysAlaGln
                       1870                     1890                     1910
gaaaaatggatgaaagaaagagaagtctaataaaaaggctcaagaagatctcgcaaaa
GluLysTrpMetLysGluLysGluLysSerAsnLysLysAlaGlnGluAspLeuAlaLys
                       1930                     1950                     1970
catgtgaaataactgttgcaaaatataagaaaaggattagtattcttgaatgctgaa
HisValLysEnd
                       1990                     2010
tcctttttacatttgtaaagaaagattctaaatgtact
```

FIG. 12A

```
        *
PlpA  GVLAACSGS- GSSAKGEKTF SYIYETDPDN LNYLTTAKAA TANITSNVVD  49
AmiA  GVLAACSSSK SSDSSAPKAY GYVYTADPET LDYLISRKNS TVVTSNGID   50

PlpA  GLLENDRYGN FVPSMAEDWS VSKDGLTYTY TIRKDAKWYT SEGEEYAAVK  99
AmiA  GLFTNDNYGN LAPAVAEDWE VSKDGLTYTY KIRKGVKWFT SDGEEYAEVT 100

PlpA  ADDFVTGLKY AADKKSDALY PVQESIKGLD AYVKGEIKDF SDVGIKALDE 149
AmiA  AKDFVNGLKH AADKKSEAMY LAENSVKGLA DYLSGTSTDF STVGVKAVDD 150

PlpA  QTVQYTLNKP ESFWNSKTTM GVLAPVNEEF LNSKGDDFAK ATDPSSLLYN 199
AmiA  YTLQYTLNQP EPFWNSKLTY SIFWPLNEEF ETSKGSDFAK PTDPTSLLYN 200

PlpA  GPYLLKSIVT KSSVEFAKNP NYWDKDVHI  DKVKLSFWDG QDTSKPAENF 249
AmiA  GPFLLKGLTA KSSVEFVKNE QYWDKENVHL DTINLAYYDG SDQESLERNF 250

PlpA  KDGSLTAARL YPTSASFAEL EKSMKDNIVY TQDDSITYLV GTNIDRQSYK 299
AmiA  TSGAYSYARL YPTSSNYSKV AEEYKDNIYY TQSGSGIAGL GVNIDRQSYN 300

PlpA  YTSKTSDEQK ASTKKALLNK DFRQAIAFGF DRTAYASQLN GQTGASKILR 349
AmiA  YTSKTTDSEK VATKKALLNK DFRQALNFAL DRSAYSAQIN GKDGAALAVR 350

PlpA  NLFVPPTFVQ ADGKNFGDMV KEKLVTYGDE WKDVNLADSQ DGLYNPEKAK 399
AmiA  NLFVKPDFVS AGEKTFGDLV AAQLPAYGDE WKGVNLADGQ DGLFNADKAK 400

PlpA  AEFAKAKSAL QAEGVTFPIH LDMPVDQTAT TKVQRVQSMK QSLEATLGAD 449
AmiA  AEFRKAKKAL EADGVQFPIH LDVPVDQASK NYISRIQSFK QSVETVLGVE 450

PlpA  NVIIDIQQLQ KDEVNNITYF AENAAGEDWD LSDNVGWGPD FADPSTYLDI 499
AmiA  NVVVDIQQMT SDEFLNITYY AANASSEDWD VSGGVSWGPD YQDPSTYLDI 497

PlpA  IKPSVGESTK TYLGFDSGED NVAAKKVGLY DYEKLVTEAG DETTDVAKRY 549
AmiA  LKTTSSETTK TYLGFDNPN- SPSVVQVGLK EYDKLVDEAA KETSDFNVRY 546

PlpA  DKYAAAQAWL TDSALIIPTT SRTG-RPILS KMVPFTIPFA LSGNKGTSEP 598
AmiA  EKYAAAQAWL TDSSLFIPAM ASSGAAPVLS RIVPFTGASA QTGSKGSD-- 594

PlpA  VLYKYLELQD KAVTVDEYQK AQEKWMKEKE ESNKKAQEDL AKHVK       643
AmiA  VYFKYLKLQD KAVTKEEYEK AREKWLKEKA ESNEKAQKEL ASHVK       639
```

FIG. 13
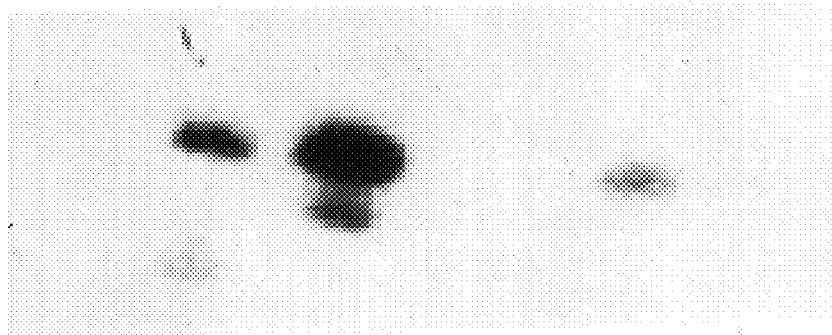
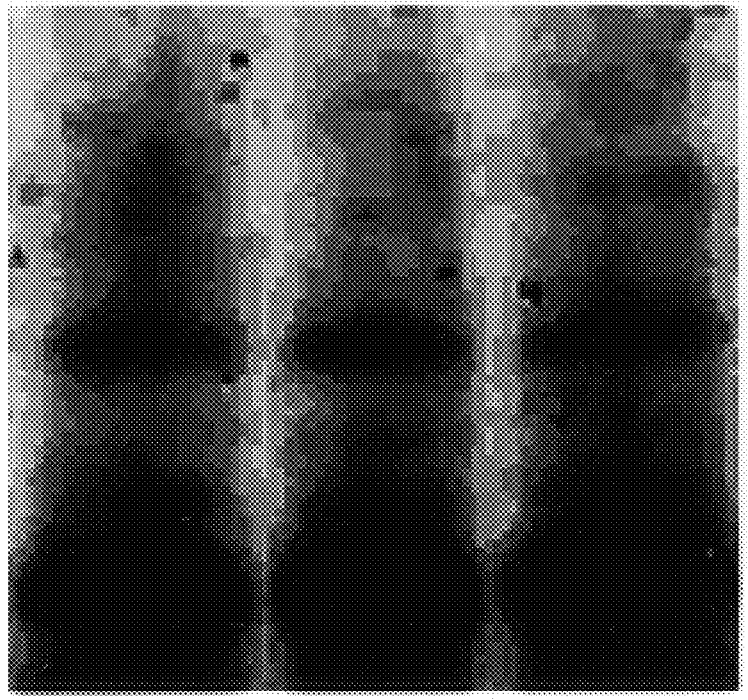

FIG. 15

| Chromosomal gene construction | Strain | Percent of control |
|---|---|---|
| plpA | R6x | 100.0 ± 17.6 |
| plpA / phoA / E | SPRU98 | 12.5 ± 3.2 |
| plpA / E | SPRU107 | 6.3 ± 1.6 |
| plpA / phoA / E | SPRU58 | 49.3 ± 0.8 |
| plpA / E | SPRU122 | 7.8 ± 1.6 |
| amiA / amiC | R6x | 100.0 ± 28.2 |
| amiA / phoA / E | SPRU121 | 116.3 ± 16.1 |
| amiA / E | SPRU114 | 130.2 ± 16.1 |
| amiA / amiC / E | SPRU148 | 371.5 ± 31.9 |

A B C D E F

Membrane   Cytoplasm

A, D R6, parent
B, E *Pad1*
C, F *Pad1b*

A B C

Membrane

A, R6, parent
B, *Pad1*
C, *Pad1b*

FIG. 23A

Upstream region

[contains ribosome binding site, putative −10 and −35 sites; translation initiation codon (bold)]

ttgagcagatttagaaaagtcagcataatatgatacaggtggaatagtaaaatttggagaacgtttccaattctatgt
atcggtatctccaagtttaaaaaaattgaaggagagttatcatatgactactcaagggaaaattactgcatctgcagcaat
gcttaacgtattgaaaacatggggcgtagatacaatctacggtatccatcaggaacactcagctcattgatgacgctt
tggctgaagacaaagatatcc

FIG. 23B

Protein translation

MTQGKITASAAMLNVLKTWGVDTIYGIPSGTLSSLMDALAEDKDI

FIG.23C

Continuing sequence aagtccgccacgaagagacaggtgtcttgcattcggttatgcaagctaaattcggcggctcaatcggggttgcagttgg
ttcaggtggtccagtgcgactcactgattaacgtgttacgatgcagctatggataacactccattcctagcgatcc
ttggatcacgtccagttaacgaattgaacatggatgcttccaagagcttaaccaaaaccaatgtacaacggtatcgct
gtttacaacaaacgtgtagcttacgctgagcaattgccaaaagtaattgacgaagcctgccgtgctgcaatttctaaaaa
aggtccagctgttgttgaaattccagtaaaactcggtttccaagaaatcgacgaaaatcatactacggttcaggttcat
acgaacgctcattcatcgctcctgcttgaacgaagttgaaatcgacaaagctgttgaaatcttgaacaatgctgaacgc
ccagttatctatgctgaatttggtggtgttaaagctgtggtgaagtgattactgaaggtttgacagttctgcttaccgtgttggttgga
catcacaactggtaaaaacttgaagcttcgaatgaactatgaagcttcttttcctgttcaaactcgcattgctgaagtttacgaa
aaccagccaacgaagtggtctttgaagcagacacagtcgatatcgacccttacaaagtaaaccgtcatgccctgacgcttc
gcattcaagaacactgaaaaattcatacaagtcgtcaagcagctaaagctatcctgacaaagtaaacccagttgaatcaactcatggtgccgtg
aatccttggtgatgctggtcaagcagcagctaaagctatcctgacaaagtaaacccagttgaatcaactcatggtgccgtg
caaacgttaagaacaaccaaaactggcgtgattacatgaacaaactcgaaggtaaaactgaaggtaaaactgaggtgaaattgtat
caagtttacaatgcaatcaacaaacatgctgatc

FIG. 23D

Protein translation

KSATKRQVLLHSVMQAKFGGSIGVAVGSGGPGATHLINGVYDAAMDNTPFLAIL
GSRPVNELNMDAFQELNQNPMYNGIA
VYNKRVAYAEQLPKVIDEACRAAISKKGPAVVEIPVNFGFQEIDENSYYGSGSYE
RSFIAPALNEVEIDKAVEILNNAER
PVIYAGFGGVKAGEVITELSRKIKAPIITGKNFEAFEWNYEGLTGSAYRVGWKP
ANEVVFEADTVLFLGSNFAFAEVYE
AFKNTEKFIQVDIDPYKLGKRHALDASILGDAGQAAKAILDKVNPVESTPWWRA
NVKNNQNWRDYMNKLEGKTEGELQLY
QVYNAINKHAD

Based on sequence homology there are about 200 AA missing for the complete gene

SEQUENCE LISTING (1) GENERAL INFORMATION:

(iii) NUMBER OF SEQUENCES: 58

(2) INFORMATION FOR SEQ ID NO:1:

(i) SEQUENCE CHARACTERISTICS:
        (A) LENGTH: 490 base pairs
        (B) TYPE: nucleic acid
        (C) STRANDEDNESS: both
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
              (A) ORGANISM: Streptococcus pneumoniae
              (B) STRAIN: R6

(vii) IMMEDIATE SOURCE:
              (B) CLONE: SPRU98

(ix) FEATURE:
              (A) NAME/KEY: CDS
              (B) LOCATION: 1..490

(xi) SEQUENCE DESCRIPTION: SEQ ID NO:1:

```
GAT CGT ACA GCC TAT GCC TCT CAG TTG AAT GGA CAA ACT GGA GCA AGT         48
Asp Arg Thr Ala Tyr Ala Ser Gln Leu Asn Gly Gln Thr Gly Ala Ser
 1               5                  10                  15

AAA ATC TTG CGT AAT CTC TTT GTG CCA CCA ACA TTT GTT CAA GCA GAT         96
Lys Ile Leu Arg Asn Leu Phe Val Pro Pro Thr Phe Val Gln Ala Asp
             20                  25                  30

GGT AAA AAC TTT GGC GAT ATG GTC AAA GAG AAA TTG GTC ACT TAT GGG        144
Gly Lys Asn Phe Gly Asp Met Val Lys Glu Lys Leu Val Thr Tyr Gly
         35                  40                  45

GAT GAA TGG AAG GAT GTT AAT CTT GCA GAT TCT CAG GAT GGT CTT TAC        192
Asp Glu Trp Lys Asp Val Asn Leu Ala Asp Ser Gln Asp Gly Leu Tyr
 50                  55                  60

AAT CCA GAA AAA GCC AAG GCT GAA TTT GCT AAA GCT AAA TCA GCC TTA        240
Asn Pro Glu Lys Ala Lys Ala Glu Phe Ala Lys Ala Lys Ser Ala Leu
 65                  70                  75                  80

CAA GCA GAA GGT GTG ACA TTC CCA ATT CAT TTG GAT ATG CCA GTT GAC        288
Gln Ala Glu Gly Val Thr Phe Pro Ile His Leu Asp Met Pro Val Asp
                 85                  90                  95

CAG ACA GCA ACT ACA AAA GTT CAG CGC GTC CAA TCT ATG AAA CAA TCC        336
Gln Thr Ala Thr Thr Lys Val Gln Arg Val Gln Ser Met Lys Gln Ser
            100                 105                 110

TTG GAA GCA ACT TTA GGA GCT GAT AAT GTC ATT ATT GAT ATT CAA CAA        384
Leu Glu Ala Thr Leu Gly Ala Asp Asn Val Ile Ile Asp Ile Gln Gln
        115                 120                 125

CTA CAA AAA GAC GAA GTA AAC AAT ATT ACA TAT TTT GCT GAA AAT GCT        432
Leu Gln Lys Asp Glu Val Asn Asn Ile Thr Tyr Phe Ala Glu Asn Ala
    130                 135                 140

GCT GGC GAA GAC TGG GAT TTA TCA GAT AAT GTC GGT TGG GGT CCA GAC        480
Ala Gly Glu Asp Trp Asp Leu Ser Asp Asn Val Gly Trp Gly Pro Asp
145                 150                 155                 160

TTT GCC GAT C                                                          490
Phe Ala Asp
```

(2) INFORMATION FOR SEQ ID NO:2:

(i) SEQUENCE CHARACTERISTICS:
              (A) LENGTH: 163 amino acids
              (B) TYPE: amino acid
              (D) TOPOLOGY: linear (ii) MOLECULE TYPE: protein (xi) SEQUENCE DESCRIPTION: SEQ ID NO:2:

```
Asp Arg Thr Ala Tyr Ala Ser Gln Leu Asn Gly Gln Thr Gly Ala Ser
 1               5                  10                  15

Lys Ile Leu Arg Asn Leu Phe Val Pro Pro Thr Phe Val Gln Ala Asp
             20                  25                  30
```

-continued

```
Gly Lys Asn Phe Gly Asp Met Val Lys Glu Lys Leu Val Thr Tyr Gly
         35                  40                  45

Asp Glu Trp Lys Asp Val Asn Leu Ala Asp Ser Gln Asp Gly Leu Tyr
 50                  55                  60

Asn Pro Glu Lys Ala Lys Ala Glu Phe Ala Lys Ala Lys Ser Ala Leu
 65                  70                  75                  80

Gln Ala Glu Gly Val Thr Phe Pro Ile His Leu Asp Met Pro Val Asp
                 85                  90                  95

Gln Thr Ala Thr Thr Lys Val Gln Arg Val Gln Ser Met Lys Gln Ser
                100                 105                 110

Leu Glu Ala Thr Leu Gly Ala Asp Asn Val Ile Ile Asp Ile Gln Gln
            115                 120                 125

Leu Gln Lys Asp Glu Val Asn Asn Ile Thr Tyr Phe Ala Glu Asn Ala
130                 135                 140

Ala Gly Glu Asp Trp Asp Leu Ser Asp Asn Val Gly Trp Gly Pro Asp
145                 150                 155                 160

Phe Ala Asp
```

(2) INFORMATION FOR SEQ ID NO:3:

(i) SEQUENCE CHARACTERISTICS:
        (A) LENGTH: 960 base pairs
        (B) TYPE: nucleic acid
        (C) STRANDEDNESS: both
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pneumoniae
        (B) STRAIN: R6

(vii) IMMEDIATE SOURCE:
        (B) CLONE: SPRU42

(ix) FEATURE:
        (A) NAME/KEY: CDS
        (B) LOCATION: 1..960

(xi) SEQUENCE DESCRIPTION: SEQ ID NO:3:

```
ACA ACT TCT AGT AAA ATC TAC GAC AAT AAA AAT CAA CTC ATT GCT GAC     48
Thr Thr Ser Ser Lys Ile Tyr Asp Asn Lys Asn Gln Leu Ile Ala Asp
 1               5                  10                  15

TTG GGT TCT GAA CGC CGC GTC AAT GCC CAA GCT AAT GAT ATT CCC ACA     96
Leu Gly Ser Glu Arg Arg Val Asn Ala Gln Ala Asn Asp Ile Pro Thr
             20                  25                  30

GAT TTG GTT AAG GCA ATC GTT TCT ATC GAA GAC CAT CGC TTC TTC GAC    144
Asp Leu Val Lys Ala Ile Val Ser Ile Glu Asp His Arg Phe Phe Asp
         35                  40                  45

CAC AGG GGG ATT GAT ACC ATC CGT ATC CTG GGA GCT TTC TTG CGC AAT    192
His Arg Gly Ile Asp Thr Ile Arg Ile Leu Gly Ala Phe Leu Arg Asn
 50                  55                  60

CTG CAA AGC AAT TCC CTC CAA GGT GGA TCA GCT CTC ACT CAA CAG TTG    240
Leu Gln Ser Asn Ser Leu Gln Gly Gly Ser Ala Leu Thr Gln Gln Leu
 65                  70                  75                  80

ATT AAG TTG ACT TAC TTT TCA ACT TCG ACT TCC GAC CAG ACT ATT TCT    288
Ile Lys Leu Thr Tyr Phe Ser Thr Ser Thr Ser Asp Gln Thr Ile Ser
                 85                  90                  95
```

-continued

```
CGT AAG GCT CAG GAA GCT TGG TTA GCG ATT CAG TTA GAA CAA AAA GCA            336
Arg Lys Ala Gln Glu Ala Trp Leu Ala Ile Gln Leu Glu Gln Lys Ala
        100                 105                 110

ACC AAG CAA GAA ATC TTG ACC TAC TAT ATA AAT AAG GTC TAC ATG TCT            384
Thr Lys Gln Glu Ile Leu Thr Tyr Tyr Ile Asn Lys Val Tyr Met Ser
    115                 120                 125

AAT GGG AAC TAT GGA ATG CAG ACA GCT GCT CAA AAC TAC TAT GGT AAA            432
Asn Gly Asn Tyr Gly Met Gln Thr Ala Ala Gln Asn Tyr Tyr Gly Lys
130                 135                 140

GAC CTC AAT AAT TTA AGT TTA CCT CAG TTA GCC TTG CTG GCT GGA ATG            480
Asp Leu Asn Asn Leu Ser Leu Pro Gln Leu Ala Leu Leu Ala Gly Met
145                 150                 155                 160

CCT CAG GCA CCA AAC CAA TAT GAC CCC TAT TCA CAT CCA GAA GCA GCC            528
Pro Gln Ala Pro Asn Gln Tyr Asp Pro Tyr Ser His Pro Glu Ala Ala
                165                 170                 175

CAA GAC CGC CGA AAC TTG GTC TTA TCT GAA ATG AAA AAT CAA GGC TAC            576
Gln Asp Arg Arg Asn Leu Val Leu Ser Glu Met Lys Asn Gln Gly Tyr
            180                 185                 190

ATC TCT GCT GAA CAG TAT GAG AAA GCA GTC AAT ACA CCA ATT ACT GAT            624
Ile Ser Ala Glu Gln Tyr Glu Lys Ala Val Asn Thr Pro Ile Thr Asp
        195                 200                 205

GGG CTA CAA AGT CTC AAA TCA GCA AGT AAT TAC CCT GCT TAC ATG GAT            672
Gly Leu Gln Ser Leu Lys Ser Ala Ser Asn Tyr Pro Ala Tyr Met Asp
    210                 215                 220

AAT TAC CTC AAG GAA GTC ATC AAT CAA GTT GAA GAA GAA ACA GGC TAT            720
Asn Tyr Leu Lys Glu Val Ile Asn Gln Val Glu Glu Glu Thr Gly Tyr
225                 230                 235                 240

AAC CTA CTC ACA ACT GGG ATG GAT GTC TAC ACA AAT GTA GAC CAA GAA            768
Asn Leu Leu Thr Thr Gly Met Asp Val Tyr Thr Asn Val Asp Gln Glu
                245                 250                 255

GCT CAA AAA CAT CTG TGG GAT ATT TAC AAT ACA GAC GAA TAC GTT GCC            816
Ala Gln Lys His Leu Trp Asp Ile Tyr Asn Thr Asp Glu Tyr Val Ala
            260                 265                 270

TAT CCA GAC GAT GAA TTG CAA GTC GCT TCT ACC ATT GTT GAT GTT TCT            864
Tyr Pro Asp Asp Glu Leu Gln Val Ala Ser Thr Ile Val Asp Val Ser
        275                 280                 285

AAC GGT AAA GTC ATT GCC CAG CTA GGA GCA CGC CAT CAG TCA AGT AAT            912
Asn Gly Lys Val Ile Ala Gln Leu Gly Ala Arg His Gln Ser Ser Asn
    290                 295                 300

GTT TCC TTC GGA ATT AAC CAA GCA GTA GAA ACA AAC CGC GAC TGG GGA            960
Val Ser Phe Gly Ile Asn Gln Ala Val Glu Thr Asn Arg Asp Trp Gly
305                 310                 315                 320
```

(2) INFORMATION FOR SEQ ID NO:4:

(i) SEQUENCE CHARACTERISTICS:
        (A) LENGTH: 320 amino acids
        (B) TYPE: amino acid
        (D) TOPOLOGY: linear (ii) MOLECULE TYPE: protein (xi) SEQUENCE DESCRIPTION: SEQ ID NO:4:

```
Thr Thr Ser Ser Lys Ile Tyr Asp Asn Lys Asn Gln Leu Ile Ala Asp
  1               5                  10                  15

Leu Gly Ser Glu Arg Arg Val Asn Ala Gln Ala Asn Asp Ile Pro Thr
                20                  25                  30

Asp Leu Val Lys Ala Ile Val Ser Ile Glu Asp His Arg Phe Phe Asp
            35                  40                  45

His Arg Gly Ile Asp Thr Ile Arg Ile Leu Gly Ala Phe Leu Arg Asn
        50                  55                  60
```

```
Leu Gln Ser Asn Ser Leu Gln Gly Gly Ser Ala Leu Thr Gln Gln Leu
 65                  70                  75                  80

Ile Lys Leu Thr Tyr Phe Ser Thr Ser Thr Ser Asp Gln Thr Ile Ser
                 85                  90                  95

Arg Lys Ala Gln Glu Ala Trp Leu Ala Ile Gln Leu Glu Gln Lys Ala
            100                 105                 110

Thr Lys Gln Glu Ile Leu Thr Tyr Tyr Ile Asn Lys Val Tyr Met Ser
        115                 120                 125

Asn Gly Asn Tyr Gly Met Gln Thr Ala Ala Gln Asn Tyr Tyr Gly Lys
130                 135                 140

Asp Leu Asn Asn Leu Ser Leu Pro Gln Leu Ala Leu Leu Ala Gly Met
145                 150                 155                 160

Pro Gln Ala Pro Asn Gln Tyr Asp Pro Tyr Ser His Pro Glu Ala Ala
                165                 170                 175

Gln Asp Arg Arg Asn Leu Val Leu Ser Glu Met Lys Asn Gln Gly Tyr
            180                 185                 190

Ile Ser Ala Glu Gln Tyr Glu Lys Ala Val Asn Thr Pro Ile Thr Asp
        195                 200                 205

Gly Leu Gln Ser Leu Lys Ser Ala Ser Asn Tyr Pro Ala Tyr Met Asp
    210                 215                 220

Asn Tyr Leu Lys Glu Val Ile Asn Gln Val Glu Glu Thr Gly Tyr
225                 230                 235                 240

Asn Leu Leu Thr Thr Gly Met Asp Val Tyr Thr Asn Val Asp Gln Glu
                245                 250                 255

Ala Gln Lys His Leu Trp Asp Ile Tyr Asn Thr Asp Glu Tyr Val Ala
            260                 265                 270

Tyr Pro Asp Asp Glu Leu Gln Val Ala Ser Thr Ile Val Asp Val Ser
        275                 280                 285

Asn Gly Lys Val Ile Ala Gln Leu Gly Ala Arg His Gln Ser Ser Asn
290                 295                 300

Val Ser Phe Gly Ile Asn Gln Ala Val Glu Thr Asn Arg Asp Trp Gly
305                 310                 315                 320
```

(2) INFORMATION FOR SEQ ID NO:5:

(i) SEQUENCE CHARACTERISTICS:
        (A) LENGTH: 520 base pairs
        (B) TYPE: nucleic acid
        (C) STRANDEDNESS: both
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pneumoniae
        (B) STRAIN: R6

(vii) IMMEDIATE SOURCE:
        (B) CLONE: SPRU40

(ix) FEATURE:
        (A) NAME/KEY: CDS
        (B) LOCATION: 1..519

(xi) SEQUENCE DESCRIPTION: SEQ ID NO:5:

```
GAT CCT CTA TCT ATC AAT CAA CAA GGG AAT GAC CGT GGT CGC CAA TAT      48
Asp Pro Leu Ser Ile Asn Gln Gln Gly Asn Asp Arg Gly Arg Gln Tyr
  1               5                  10                  15
```

-continued

```
CGA ACT GGG ATT TAT TAT CAG GAT GAA GCA GAT TTG CCA GCT ATC TAC        96
Arg Thr Gly Ile Tyr Tyr Gln Asp Glu Ala Asp Leu Pro Ala Ile Tyr
            20                  25                  30

ACA GTG GTG CAG GAG CAG GAA CGC ATG CTG GGT CGA AAG ATT GCA GTA       144
Thr Val Val Gln Glu Gln Glu Arg Met Leu Gly Arg Lys Ile Ala Val
        35                  40                  45

GAA GTG GAG CAA TTA CGC CAC TAC ATT CTG GCT GAA GAC TAC CAC CAA       192
Glu Val Glu Gln Leu Arg His Tyr Ile Leu Ala Glu Asp Tyr His Gln
    50                  55                  60

GAC TAT CTC AGG AAG AAT CCT TCA GGT TAC TGT CAT ATC GAT GTG ACC       240
Asp Tyr Leu Arg Lys Asn Pro Ser Gly Tyr Cys His Ile Asp Val Thr
65                  70                  75                  80

GAT GCT GAT AAG CCA TTG ATT GAT GCA GCA AAC TAT GAA AAG CCT AGT       288
Asp Ala Asp Lys Pro Leu Ile Asp Ala Ala Asn Tyr Glu Lys Pro Ser
                85                  90                  95

CAA GAG GTG TTG AAG GCC AGT CTA TCT GAA GAG TCT TAT CGT GTC ACA       336
Gln Glu Val Leu Lys Ala Ser Leu Ser Glu Glu Ser Tyr Arg Val Thr
            100                 105                 110

CAA GAA GCT GCT ACA GAG GCT CCA TTT ACC AAT GCC TAT GAC CAA ACC       384
Gln Glu Ala Ala Thr Glu Ala Pro Phe Thr Asn Ala Tyr Asp Gln Thr
        115                 120                 125

TTT GAA GAG GGG ATT TAT GTA GAT ATT ACG ACA GGT GAG CCA CTC TTT       432
Phe Glu Glu Gly Ile Tyr Val Asp Ile Thr Thr Gly Glu Pro Leu Phe
    130                 135                 140

TTT GCC AAG GAT AAG TTT GCT TCA GGT TGT GGT TGG CCA AGT TTT AGC       480
Phe Ala Lys Asp Lys Phe Ala Ser Gly Cys Gly Trp Pro Ser Phe Ser
145                 150                 155                 160

CGT CCG ATT TCC AAA GAG TTG ATT CAT TAT TAC AAG GAT C                 520
Arg Pro Ile Ser Lys Glu Leu Ile His Tyr Tyr Lys Asp
                165                 170
```

(2) INFORMATION FOR SEQ ID NO:6:

(i) SEQUENCE CHARACTERISTICS:
        (A) LENGTH: 173 amino acids
        (B) TYPE: amino acid
        (D) TOPOLOGY: linear (ii) MOLECULE TYPE: protein (xi) SEQUENCE DESCRIPTION: SEQ ID NO:6:

```
Asp Pro Leu Ser Ile Asn Gln Gln Gly Asn Asp Arg Gly Arg Gln Tyr
1               5                   10                  15

Arg Thr Gly Ile Tyr Tyr Gln Asp Glu Ala Asp Leu Pro Ala Ile Tyr
            20                  25                  30

Thr Val Val Gln Glu Gln Glu Arg Met Leu Gly Arg Lys Ile Ala Val
        35                  40                  45

Glu Val Glu Gln Leu Arg His Tyr Ile Leu Ala Glu Asp Tyr His Gln
    50                  55                  60

Asp Tyr Leu Arg Lys Asn Pro Ser Gly Tyr Cys His Ile Asp Val Thr
65                  70                  75                  80

Asp Ala Asp Lys Pro Leu Ile Asp Ala Ala Asn Tyr Glu Lys Pro Ser
                85                  90                  95

Gln Glu Val Leu Lys Ala Ser Leu Ser Glu Glu Ser Tyr Arg Val Thr
            100                 105                 110

Gln Glu Ala Ala Thr Glu Ala Pro Phe Thr Asn Ala Tyr Asp Gln Thr
        115                 120                 125

Phe Glu Glu Gly Ile Tyr Val Asp Ile Thr Thr Gly Glu Pro Leu Phe
    130                 135                 140
```

```
Phe Ala Lys Asp Lys Phe Ala Ser Gly Cys Gly Trp Pro Ser Phe Ser
145                 150                 155                 160

Arg Pro Ile Ser Lys Glu Leu Ile His Tyr Tyr Lys Asp
                165                 170
```

(2) INFORMATION FOR SEQ ID NO:7:

(i) SEQUENCE CHARACTERISTICS:
        (A) LENGTH: 282 base pairs
        (B) TYPE: nucleic acid
        (C) STRANDEDNESS: both
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pneumoniae
        (B) STRAIN: R6

(vii) IMMEDIATE SOURCE:
        (B) CLONE: SPRU39

(ix) FEATURE:
        (A) NAME/KEY: CDS
        (B) LOCATION: 3..281

(xi) SEQUENCE DESCRIPTION: SEQ ID NO:7:

```
CC TCA AAT GCA GGT ACA GGA AAG ACC GAA GCT AGC GTT GGA TTT GGT         47
   Ser Asn Ala Gly Thr Gly Lys Thr Glu Ala Ser Val Gly Phe Gly
   1               5                  10                  15

GCT GCT AGA GAA GGA CGT ACC AAT TCT GTC CTC GGT GAA CTC GGT AAC        95
Ala Ala Arg Glu Gly Arg Thr Asn Ser Val Leu Gly Glu Leu Gly Asn
            20                  25                  30

TTC TTT AGC CCA GAG TTT ATG AAC CGT TTT GAT GGC ATT ATC GAA TTT       143
Phe Phe Ser Pro Glu Phe Met Asn Arg Phe Asp Gly Ile Ile Glu Phe
        35                  40                  45

AAG GCT CTC AGC AAG GAT AAC CTC CTT CAG ATT GTC GAG CTC ATG CTA       191
Lys Ala Leu Ser Lys Asp Asn Leu Leu Gln Ile Val Glu Leu Met Leu
    50                  55                  60

GCA GAT GTT AAC AAG CGC CTC TCT AGT AAC AAC ATT CGT TTG GAT GTA       239
Ala Asp Val Asn Lys Arg Leu Ser Ser Asn Asn Ile Arg Leu Asp Val
65                  70                  75

ACT GAT AAG GTC AAG GAA AAG TTG GTT GAC CTA GGT TAT GAT               281
Thr Asp Lys Val Lys Glu Lys Leu Val Asp Leu Gly Tyr Asp
80                  85                  90

C                                                                     282
```

(2) INFORMATION FOR SEQ ID NO:8:

(i) SEQUENCE CHARACTERISTICS:
        (A) LENGTH: 93 amino acids
        (B) TYPE: amino acid
        (D) TOPOLOGY: linear (ii) MOLECULE TYPE: protein (xi) SEQUENCE DESCRIPTION: SEQ ID NO:8:

```
Ser Asn Ala Gly Thr Gly Lys Thr Glu Ala Ser Val Gly Phe Gly Ala
1               5                  10                  15

Ala Arg Glu Gly Arg Thr Asn Ser Val Leu Gly Glu Leu Gly Asn Phe
            20                  25                  30

Phe Ser Pro Glu Phe Met Asn Arg Phe Asp Gly Ile Ile Glu Phe Lys
        35                  40                  45
```

Ala Leu Ser Lys Asp Asn Leu Leu Gln Ile Val Glu Leu Met Leu Ala
             50                  55                  60

Asp Val Asn Lys Arg Leu Ser Ser Asn Asn Ile Arg Leu Asp Val Thr
 65                  70                  75                  80

Asp Lys Val Lys Glu Lys Leu Val Asp Leu Gly Tyr Asp
                 85                  90

(2) INFORMATION FOR SEQ ID NO:9:

(i) SEQUENCE CHARACTERISTICS:
        (A) LENGTH: 327 base pairs
        (B) TYPE: nucleic acid
        (C) STRANDEDNESS: both
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pneumoniae
        (B) STRAIN: R6

(vii) IMMEDIATE SOURCE:
        (B) CLONE: SPRU87

(ix) FEATURE:
        (A) NAME/KEY: CDS
        (B) LOCATION: 3..326

(xi) SEQUENCE DESCRIPTION: SEQ ID NO:9:

```
AA GTG AAA GTT GAC GAC GGC TCT CAA GCT GTA AAC ATT ATC AAC CTT        47
   Val Lys Val Asp Asp Gly Ser Gln Ala Val Asn Ile Ile Asn Leu
    1               5                  10                  15

CTT GGT GGA CGT GTA AAC ATC GTT GAT GTT GAT GCA TGT ATG ACT CGT        95
Leu Gly Gly Arg Val Asn Ile Val Asp Val Asp Ala Cys Met Thr Arg
                 20                  25                  30

CTT CGT GTA ACT GTT AAA GAT GCA GAT AAA GTA GGA AAT GCA GAG CAA       143
Leu Arg Val Thr Val Lys Asp Ala Asp Lys Val Gly Asn Ala Glu Gln
                     35                  40                  45

TGG AAA GCA GAA GGA GCT ATG GGT CTT GTG ATG AAA GGA CAA GGG GTT       191
Trp Lys Ala Glu Gly Ala Met Gly Leu Val Met Lys Gly Gln Gly Val
             50                  55                  60

CAA GCT ATC TAC GGT CCA AAA GCT GAC ATT TTG AAA TCT GAT ATC CAA       239
Gln Ala Ile Tyr Gly Pro Lys Ala Asp Ile Leu Lys Ser Asp Ile Gln
 65                  70                  75

GAT ATC CTT GAT TCA GGT GAA ATC ATT CCT GAA ACT CTT CCA AGC CAA       287
Asp Ile Leu Asp Ser Gly Glu Ile Ile Pro Glu Thr Leu Pro Ser Gln
 80                  85                  90                  95

ATG ACT GAA GTA CAA CAA AAC ACT GTT CAC TTC AAA GAT C                 327
Met Thr Glu Val Gln Gln Asn Thr Val His Phe Lys Asp
                100                 105
```

(2) INFORMATION FOR SEQ ID NO:10:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO:10:

Val Lys Val Asp Asp Gly Ser Gln Ala Val Asn Ile Ile Asn Leu Leu
 1               5                  10                  15

```
Gly Gly Arg Val Asn Ile Val Asp Val Asp Ala Cys Met Thr Arg Leu
            20                  25                  30

Arg Val Thr Val Lys Asp Ala Asp Lys Val Gly Asn Ala Glu Gln Trp
        35                  40                  45

Lys Ala Glu Gly Ala Met Gly Leu Val Met Lys Gly Gln Gly Val Gln
    50                  55                  60

Ala Ile Tyr Gly Pro Lys Ala Asp Ile Leu Lys Ser Asp Ile Gln Asp
65                  70                  75                  80

Ile Leu Asp Ser Gly Glu Ile Ile Pro Glu Thr Leu Pro Ser Gln Met
            85                  90                  95

Thr Glu Val Gln Gln Asn Thr Val His Phe Lys Asp
            100                 105
```

(2) INFORMATION FOR SEQ ID NO:11:

(i) SEQUENCE CHARACTERISTICS:
        (A) LENGTH: 417 base pairs
        (B) TYPE: nucleic acid
        (C) STRANDEDNESS: both
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pneumoniae
        (B) STRAIN: R6

(vii) IMMEDIATE SOURCE:
        (B) CLONE: SPRU24

(ix) FEATURE:
        (A) NAME/KEY: CDS
        (B) LOCATION: 3..416

(xi) SEQUENCE DESCRIPTION: SEQ ID NO:11:

```
TT TCA CAG CCA GTT TCA TTT GAC ACA GGT TTG GGT GAC GGT CGT ATG         47
   Ser Gln Pro Val Ser Phe Asp Thr Gly Leu Gly Asp Gly Arg Met
    1               5                  10                  15

GTC TTT GTT CTC CCA CGT GAA AAC AAG ACT TAC TTT GGT ACA ACT GAT        95
Val Phe Val Leu Pro Arg Glu Asn Lys Thr Tyr Phe Gly Thr Thr Asp
                    20                  25                  30

ACA GAC TAC ACA GGT GAT TTG GAG CAT CCA AAA GTA ACT CAA GAA GAT       143
Thr Asp Tyr Thr Gly Asp Leu Glu His Pro Lys Val Thr Gln Glu Asp
                35                  40                  45

GTA GAT TAT CTA CTT GGC ATT GTC AAC AAC CGC TTT CCA GAA TCC AAC       191
Val Asp Tyr Leu Leu Gly Ile Val Asn Asn Arg Phe Pro Glu Ser Asn
            50                  55                  60

ATC ACC ATT GAT GAT ATC GAA AGC AGC TGG GCA GGT CTT CGT CCA TTG       239
Ile Thr Ile Asp Asp Ile Glu Ser Ser Trp Ala Gly Leu Arg Pro Leu
65                  70                  75

ATT GCA GGG AAC AGT GCC TCT GAC TAT AAT GGT GGA AAT AAC GGT ACC       287
Ile Ala Gly Asn Ser Ala Ser Asp Tyr Asn Gly Gly Asn Asn Gly Thr
80                  85                  90                  95

ATC AGA GAT GAA AGC TTT GAC AAC TTG ATT GCG ACT GTT GAA TCT TAT       335
Ile Arg Asp Glu Ser Phe Asp Asn Leu Ile Ala Thr Val Glu Ser Tyr
                100                 105                 110

CTC TCC AAA GAA AAA ACA CGT GAA GAT GTT GAG TCT GCT GTC AGC AAG       383
Leu Ser Lys Glu Lys Thr Arg Glu Asp Val Glu Ser Ala Val Ser Lys
            115                 120                 125
```

```
CTT GAA AGT AGC ACA TCT GAG AAA CAT TTG GAT C                                    417
Leu Glu Ser Ser Thr Ser Glu Lys His Leu Asp
        130                 135
```

(2) INFORMATION FOR SEQ ID NO:12:

(i) SEQUENCE CHARACTERISTICS:
        (A) LENGTH: 138 amino acids
        (B) TYPE: amino acid
        (D) TOPOLOGY: linear (ii) MOLECULE TYPE: protein (xi) SEQUENCE DESCRIPTION: SEQ ID NO:12:

```
Ser Gln Pro Val Ser Phe Asp Thr Gly Leu Gly Asp Gly Arg Met Val
 1               5                  10                  15

Phe Val Leu Pro Arg Glu Asn Lys Thr Tyr Phe Gly Thr Thr Asp Thr
                20                  25                  30

Asp Tyr Thr Gly Asp Leu Glu His Pro Lys Val Thr Gln Glu Asp Val
            35                  40                  45

Asp Tyr Leu Leu Gly Ile Val Asn Asn Arg Phe Pro Glu Ser Asn Ile
        50                  55                  60

Thr Ile Asp Asp Ile Glu Ser Ser Trp Ala Gly Leu Arg Pro Leu Ile
 65                  70                  75                  80

Ala Gly Asn Ser Ala Ser Asp Tyr Asn Gly Gly Asn Asn Gly Thr Ile
                85                  90                  95

Arg Asp Glu Ser Phe Asp Asn Leu Ile Ala Thr Val Glu Ser Tyr Leu
            100                 105                 110

Ser Lys Glu Lys Thr Arg Glu Asp Val Glu Ser Ala Val Ser Lys Leu
        115                 120                 125

Glu Ser Ser Thr Ser Glu Lys His Leu Asp
        130                 135
```

(2) INFORMATION FOR SEQ ID NO:13:

(i) SEQUENCE CHARACTERISTICS:
        (A) LENGTH: 246 base pairs
        (B) TYPE: nucleic acid
        (C) STRANDEDNESS: both
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pneumoniae
        (B) STRAIN: R6

(vii) IMMEDIATE SOURCE:
        (B) CLONE: SPRU75

(ix) FEATURE:
        (A) NAME/KEY: CDS
        (B) LOCATION: 3..245

(xi) SEQUENCE DESCRIPTION: SEQ ID NO:13:

```
CG ACG GCC AGT GAA TTC GAG CTC GGT ACC CCT CTC AGT CAG GAG AAA       47
   Thr Ala Ser Glu Phe Glu Leu Gly Thr Pro Leu Ser Gln Glu Lys
    1               5                  10                  15

TTA GAC CAT CAC AAA CCA CAG AAA CCA TCT GAT ATT CAG GCT CTA GCC      95
Leu Asp His His Lys Pro Gln Lys Pro Ser Asp Ile Gln Ala Leu Ala
                20                  25                  30
```

```
TTG CTG GAA ATC TTG GAC CCC ATT CGA GAG GGA GCA GCA GAG ACG CTG      143
Leu Leu Glu Ile Leu Asp Pro Ile Arg Glu Gly Ala Ala Glu Thr Leu
            35                  40                  45

GAC TAT CTC CGT TCT CAG GAG GTG GGA CTC AAG ATT ATC TCT GGT GAC      191
Asp Tyr Leu Arg Ser Gln Glu Val Gly Leu Lys Ile Ile Ser Gly Asp
     50                  55                  60

AAT CCA GTT ACG GTG TCC AGC ATT GCC CAG AAG GCT GGT TTT GCG GAC      239
Asn Pro Val Thr Val Ser Ser Ile Ala Gln Lys Ala Gly Phe Ala Asp
 65                  70                  75

TAT CAC A                                                             246
Tyr His
 80

(2) INFORMATION FOR SEQ ID NO:14:

(i) SEQUENCE CHARACTERISTICS:
        (A) LENGTH: 81 amino acids
        (B) TYPE: amino acid
        (D) TOPOLOGY: linear (ii) MOLECULE TYPE: protein (xi) SEQUENCE DESCRIPTION: SEQ ID NO:14:

Thr Ala Ser Glu Phe Glu Leu Gly Thr Pro Leu Ser Gln Glu Lys Leu
 1               5                  10                  15

Asp His His Lys Pro Gln Lys Pro Ser Asp Ile Gln Ala Leu Ala Leu
             20                  25                  30

Leu Glu Ile Leu Asp Pro Ile Arg Glu Gly Ala Ala Glu Thr Leu Asp
         35                  40                  45

Tyr Leu Arg Ser Gln Glu Val Gly Leu Lys Ile Ile Ser Gly Asp Asn
     50                  55                  60

Pro Val Thr Val Ser Ser Ile Ala Gln Lys Ala Gly Phe Ala Asp Tyr
 65                  70                  75                  80

His (2) INFORMATION FOR SEQ ID NO:15:

(i) SEQUENCE CHARACTERISTICS:
        (A) LENGTH: 292 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pneumoniae
        (B) STRAIN: R6

(vii) IMMEDIATE SOURCE:
        (B) CLONE: SPRU81

(ix) FEATURE:
        (A) NAME/KEY: CDS
        (B) LOCATION: 3..290

(xi) SEQUENCE DESCRIPTION: SEQ ID NO:15:

GG CGA TTA AGT TGG GTA ACG CCA GGG TTT TCC CAG TCA CGA CGT TGT        47
   Arg Leu Ser Trp Val Thr Pro Gly Phe Ser Gln Ser Arg Arg Cys
    1               5                  10                  15

AAA ACG ACG GCC AGT GAA TTC GAG CTC GGT ACC CTG AGA AAA AAC ATC       95
Lys Thr Thr Ala Ser Glu Phe Glu Leu Gly Thr Leu Arg Lys Asn Ile
             20                  25                  30
```

```
GGT TTG GTT TTA CAG GAA CCC TTC CTC TAT CAT GGA ACT ATT AAG TCC        143
Gly Leu Val Leu Gln Glu Pro Phe Leu Tyr His Gly Thr Ile Lys Ser
            35                  40                  45

AAT ATC GCC ATG TAC CAA GAA ATC AGT GAT GAG CAG GTT CAG GCT GCG        191
Asn Ile Ala Met Tyr Gln Glu Ile Ser Asp Glu Gln Val Gln Ala Ala
        50                  55                  60

GCA GCC TTT GTG GAT GCA GAT TCC TTT ATT CAA GAA CTT CCT CAG GGG        239
Ala Ala Phe Val Asp Ala Asp Ser Phe Ile Gln Glu Leu Pro Gln Gly
    65                  70                  75

TAC GAC TCC CCT GTT TCC GAG CGT GGT TCG AGC TTC TCT ACT GGG CAG        287
Tyr Asp Ser Pro Val Ser Glu Arg Gly Ser Ser Phe Ser Thr Gly Gln
80                  85                  90                  95

CGC CA                                                                  292
Arg
```

(2) INFORMATION FOR SEQ ID NO:16:

(i) SEQUENCE CHARACTERISTICS:
        (A) LENGTH: 96 amino acids
        (B) TYPE: amino acid
        (D) TOPOLOGY: linear (ii) MOLECULE TYPE: protein (xi) SEQUENCE DESCRIPTION: SEQ ID NO:16:

```
Arg Leu Ser Trp Val Thr Pro Gly Phe Ser Gln Ser Arg Arg Cys Lys
 1               5                  10                  15

Thr Thr Ala Ser Glu Phe Glu Leu Gly Thr Leu Arg Lys Asn Ile Gly
             20                  25                  30

Leu Val Leu Gln Glu Pro Phe Leu Tyr His Gly Thr Ile Lys Ser Asn
         35                  40                  45

Ile Ala Met Tyr Gln Glu Ile Ser Asp Glu Gln Val Gln Ala Ala Ala
     50                  55                  60

Ala Phe Val Asp Ala Asp Ser Phe Ile Gln Glu Leu Pro Gln Gly Tyr
65                  70                  75                  80

Asp Ser Pro Val Ser Glu Arg Gly Ser Ser Phe Ser Thr Gly Gln Arg
                 85                  90                  95
```

(2) INFORMATION FOR SEQ ID NO:17:

(i) SEQUENCE CHARACTERISTICS:
        (A) LENGTH: 342 base pairs
        (B) TYPE: nucleic acid
        (C) STRANDEDNESS: both
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pneumoniae
        (B) STRAIN: R6

(vii) IMMEDIATE SOURCE:
        (B) CLONE: SPRU17

(ix) FEATURE:
        (A) NAME/KEY: CDS
        (B) LOCATION: 3..341

(xi) SEQUENCE DESCRIPTION: SEQ ID NO:17:

```
GA TCA AGC ATT GAA AAA CAA ATT AAG GCT CTT AAA TCT GGT GCC CAT       47
   Ser Ser Ile Glu Lys Gln Ile Lys Ala Leu Lys Ser Gly Ala His
   1               5                   10                  15

ATC GTG GTG GGA ACT CCA GGT CGC CTC TTG GAC TTG ATT AAA CGC AAG      95
Ile Val Val Gly Thr Pro Gly Arg Leu Leu Asp Leu Ile Lys Arg Lys
                    20                  25                  30

GCC TTG AAA TTA CAA GAC ATT GAA ACC CTT ATC CTT GAC GAA GCG GAT     143
Ala Leu Lys Leu Gln Asp Ile Glu Thr Leu Ile Leu Asp Glu Ala Asp
                35                  40                  45

GAA ATG CTT AAC ATG GGC TTC CTT GAA GAC ATC GAA GCC ATT ATT TCC     191
Glu Met Leu Asn Met Gly Phe Leu Glu Asp Ile Glu Ala Ile Ile Ser
            50                  55                  60

CGT GTA CCT GAG AAC CGT CAA ACT TTG CTT TTC TCA GCA ACT ATG CCA     239
Arg Val Pro Glu Asn Arg Gln Thr Leu Leu Phe Ser Ala Thr Met Pro
        65                  70                  75

GAT GCC ATC AAA CGT ATC GGT GTT CAG TTT ATG AAA GCC CCT GAA CAT     287
Asp Ala Ile Lys Arg Ile Gly Val Gln Phe Met Lys Ala Pro Glu His
80                  85                  90                  95

GTC AGA ATT GCG GCT AAG GAA TTG ACA ACA GAA TTG GTT GAC CAG TAC     335
Val Arg Ile Ala Ala Lys Glu Leu Thr Thr Glu Leu Val Asp Gln Tyr
                    100                 105                 110

TAT ATC C                                                           342
Tyr Ile (2) INFORMATION FOR SEQ ID NO:18:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO:18:

Ser Ser Ile Glu Lys Gln Ile Lys Ala Leu Lys Ser Gly Ala His Ile
1               5                   10                  15

Val Val Gly Thr Pro Gly Arg Leu Leu Asp Leu Ile Lys Arg Lys Ala
                20                  25                  30

Leu Lys Leu Gln Asp Ile Glu Thr Leu Ile Leu Asp Glu Ala Asp Glu
            35                  40                  45

Met Leu Asn Met Gly Phe Leu Glu Asp Ile Glu Ala Ile Ile Ser Arg
        50                  55                  60

Val Pro Glu Asn Arg Gln Thr Leu Leu Phe Ser Ala Thr Met Pro Asp
65                  70                  75                  80

Ala Ile Lys Arg Ile Gly Val Gln Phe Met Lys Ala Pro Glu His Val
                85                  90                  95

Arg Ile Ala Ala Lys Glu Leu Thr Thr Glu Leu Val Asp Gln Tyr Tyr
            100                 105                 110

Ile (2) INFORMATION FOR SEQ ID NO:19:

(i) SEQUENCE CHARACTERISTICS:
        (A) LENGTH: 235 base pairs
        (B) TYPE: nucleic acid
        (C) STRANDEDNESS: both
        (D) TOPOLOGY: unknown (ii) MOLECULE TYPE: DNA (genomic)

(iii) HYPOTHETICAL: NO (iv) ANTI-SENSE: NO
```

(vi) ORIGINAL SOURCE:
    (A) ORGANISM: Streptococcus pneumoniae
    (B) STRAIN: R6

(vii) IMMEDIATE SOURCE:
    (B) CLONE: SPRU17

(ix) FEATURE:
    (A) NAME/KEY: CDS
    (B) LOCATION: 1..234

(xi) SEQUENCE DESCRIPTION: SEQ ID NO:19:

```
GCA TTT GTA TTT GGT CGT ACC AAA CGC CGT GTG GAT GAA TTG ACT CGT      48
Ala Phe Val Phe Gly Arg Thr Lys Arg Arg Val Asp Glu Leu Thr Arg
 1               5                  10                  15

GGT TTG AAA ATT CGT GGC TTC CGT GCA GAA GGA ATT CAT GGC GAC CTA      96
Gly Leu Lys Ile Arg Gly Phe Arg Ala Glu Gly Ile His Gly Asp Leu
                20                  25                  30

GAC CAA AAC AAA CGT CTT CGT GTC CTT CGT GAC TTT AAA AAT GGC AAT     144
Asp Gln Asn Lys Arg Leu Arg Val Leu Arg Asp Phe Lys Asn Gly Asn
        35                  40                  45

CTT GAT GTT TTG GTT GCG ACA GAC GTT GCA GCG CGT GGT TTG GAT ATT     192
Leu Asp Val Leu Val Ala Thr Asp Val Ala Ala Arg Gly Leu Asp Ile
    50                  55                  60

TCA GGT GTG ACC CAT GTC TAC AAC TAC GAT ATT CCA CAA GAT             234
Ser Gly Val Thr His Val Tyr Asn Tyr Asp Ile Pro Gln Asp
65                  70                  75

C                                                                    235
```

(2) INFORMATION FOR SEQ ID NO:20:

(i) SEQUENCE CHARACTERISTICS:
       (A) LENGTH: 78 amino acids
       (B) TYPE: amino acid
       (D) TOPOLOGY: linear (ii) MOLECULE TYPE: protein (xi) SEQUENCE DESCRIPTION: SEQ ID NO:20:

```
Ala Phe Val Phe Gly Arg Thr Lys Arg Arg Val Asp Glu Leu Thr Arg
 1               5                  10                  15

Gly Leu Lys Ile Arg Gly Phe Arg Ala Glu Gly Ile His Gly Asp Leu
                20                  25                  30

Asp Gln Asn Lys Arg Leu Arg Val Leu Arg Asp Phe Lys Asn Gly Asn
        35                  40                  45

Leu Asp Val Leu Val Ala Thr Asp Val Ala Ala Arg Gly Leu Asp Ile
    50                  55                  60

Ser Gly Val Thr His Val Tyr Asn Tyr Asp Ile Pro Gln Asp
65                  70                  75
```

(2) INFORMATION FOR SEQ ID NO:21:

(i) SEQUENCE CHARACTERISTICS:
       (A) LENGTH: 251 base pairs
       (B) TYPE: nucleic acid
       (C) STRANDEDNESS: both
       (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
       (A) ORGANISM: Streptococcus pneumoniae (B) STRAIN: R6

(vii) IMMEDIATE SOURCE:
            (B) CLONE: SPRU25

(ix) FEATURE:
            (A) NAME/KEY: CDS
            (B) LOCATION: complement (2..250)

(xi) SEQUENCE DESCRIPTION: SEQ ID NO:21:

GATCTTGACT ATGGTAAACT ACGTAAGAAA ATTTCCTACA TTCCACAGAC CATAGACTCT    60

TTACAGGGAC AATTATTGAT AATCTAAAAA TTGGTAATCC TTCTGTTACA TATGAGGATA   120

TGGTGAGAGT TTGTCGTATT GTTGTGTATT CATGATACGA TTCAACGCCT TCAAAATCGT   180

TATGGCTCCT TTGAGAGAGG CGGTCAAATT CTCGGTGGAG AGAACACGTT GGCTTTCGAA   240

GCGCATCTGG G                                                       251

(2) INFORMATION FOR SEQ ID NO:22:

(i) SEQUENCE CHARACTERISTICS:
            (A) LENGTH: 83 amino acids
            (B) TYPE: amino acid
            (D) TOPOLOGY: linear (ii) MOLECULE TYPE: protein (xi) SEQUENCE DESCRIPTION: SEQ ID NO:22:

Pro Asp Ala Leu Arg Lys Pro Thr Cys Ser Leu His Arg Glu Phe Asp
  1               5                  10                  15

Arg Leu Ser Gln Arg Ser His Asn Asp Phe Glu Gly Val Glu Ser Tyr
             20                  25                  30

His Glu Tyr Thr Thr Ile Arg Gln Thr Leu Thr Ile Ser Ser Tyr Val
         35                  40                  45

Thr Glu Gly Leu Pro Ile Phe Arg Leu Ser Ile Ile Val Pro Val Lys
     50                  55                  60

Ser Leu Trp Ser Val Glu Cys Arg Lys Phe Ser Tyr Val Val Tyr His
 65                  70                  75                  80

Ser Gln Asp (2) INFORMATION FOR SEQ ID NO:23:

(i) SEQUENCE CHARACTERISTICS:
            (A) LENGTH: 163 amino acids
            (B) TYPE: amino acid
            (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
            (A) ORGANISM: Streptococcus pneumoniae (xi) SEQUENCE DESCRIPTION: SEQ ID NO:23:

Asp Arg Ser Ala Tyr Ser Ala Gln Ile Asn Gly Lys Asp Gly Ala Ala
  1               5                  10                  15

Leu Ala Val Arg Asn Leu Phe Val Lys Pro Asp Phe Val Ser Ala Gly
             20                  25                  30

Glu Lys Thr Phe Gly Asp Leu Val Ala Ala Gln Leu Pro Ala Tyr Gly
         35                  40                  45

```
Asp Glu Trp Lys Gly Val Asn Leu Ala Asp Gly Gln Asp Gly Leu Phe
         50                  55                  60

Asn Ala Asp Lys Ala Lys Ala Glu Phe Arg Lys Ala Lys Lys Ala Leu
 65                  70                  75                  80

Glu Ala Asp Gly Val Gln Phe Pro Ile His Leu Asp Val Pro Val Asp
                 85                  90                  95

Gln Ala Ser Lys Asn Tyr Ile Ser Arg Ile Gln Ser Phe Lys Gln Ser
                100                 105                 110

Val Glu Thr Val Leu Gly Val Glu Asn Val Val Asp Ile Gln Gln
                115                 120                 125

Met Thr Ser Asp Glu Phe Leu Asn Ile Thr Tyr Tyr Ala Ala Asn Ala
                130                 135                 140

Ser Ser Glu Asp Trp Asp Val Ser Gly Gly Val Ser Trp Gly Pro Asp
145                 150                 155                 160

Tyr Gln Asp
```

(2) INFORMATION FOR SEQ ID NO:24:

(i) SEQUENCE CHARACTERISTICS:
       (A) LENGTH: 77 amino acids
       (B) TYPE: amino acid
       (D) TOPOLOGY: unknown (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: Streptococcus pneumoniae
        (B) STRAIN: R6

(vii) IMMEDIATE SOURCE:
         (B) CLONE: SPRU42

(xi) SEQUENCE DESCRIPTION: SEQ ID NO:24:

```
Thr Thr Gly Met Asp Val Tyr Thr Asn Val Asp Gln Glu Ala Gln Lys
 1               5                  10                  15

His Leu Trp Asp Ile Tyr Asn Thr Asp Glu Tyr Val Ala Tyr Pro Asp
                 20                  25                  30

Asp Glu Leu Gln Val Ala Ser Thr Ile Val Asp Val Ser Asn Gly Lys
                 35                  40                  45

Val Ile Ala Gln Leu Gly Ala Arg His Gln Ser Ser Asn Val Ser Phe
 50                  55                  60

Gly Ile Asn Gln Ala Val Glu Thr Asn Arg Asp Trp Gly
 65                  70                  75
```

(2) INFORMATION FOR SEQ ID NO:25:

(i) SEQUENCE CHARACTERISTICS:
       (A) LENGTH: 173 amino acids
       (B) TYPE: amino acid
       (D) TOPOLOGY: unknown (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(A) ORGANISM: Streptococcus pneumoniae
            (B) STRAIN: R6

(vii) IMMEDIATE SOURCE:
            (B) CLONE: SPRU40

(xi) SEQUENCE DESCRIPTION: SEQ ID NO:25:

Asp Pro Leu Ser Ile Asn Gln Gln Gly Asn Asp Arg Gly Arg Gln Tyr
1               5                   10                  15

Arg Thr Gly Ile Tyr Tyr Gln Asp Glu Ala Asp Leu Pro Ala Ile Tyr
            20                  25                  30

Thr Val Val Gln Glu Gln Glu Arg Met Leu Gly Arg Lys Ile Ala Val
        35                  40                  45

Glu Val Glu Gln Leu Arg His Tyr Ile Leu Ala Glu Asp Tyr His Gln
    50                  55                  60

Asp Tyr Leu Arg Lys Asn Pro Ser Gly Tyr Cys His Ile Asp Val Thr
65                  70                  75                  80

Asp Ala Asp Lys Pro Leu Ile Asp Ala Ala Asn Tyr Glu Lys Pro Ser
                85                  90                  95

Gln Glu Val Leu Lys Ala Ser Leu Ser Glu Glu Ser Tyr Arg Val Thr
            100                 105                 110

Gln Glu Ala Ala Thr Glu Ala Pro Phe Thr Asn Ala Tyr Asp Gln Thr
        115                 120                 125

Phe Glu Glu Gly Ile Tyr Val Asp Ile Thr Thr Gly Glu Pro Leu Phe
    130                 135                 140

Phe Ala Lys Asp Lys Phe Ala Ser Gly Cys Gly Trp Pro Ser Phe Ser
145                 150                 155                 160

Arg Pro Ile Ser Lys Glu Leu Ile His Tyr Tyr Lys Asp
                165                 170

(2) INFORMATION FOR SEQ ID NO:26:

(i) SEQUENCE CHARACTERISTICS:
            (A) LENGTH: 175 amino acids
            (B) TYPE: amino acid
            (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
            (A) ORGANISM: Neisseria gonorrheae (xi) SEQUENCE DESCRIPTION: SEQ ID NO:26:

Asp Pro Thr Ser Leu Asn Lys Gln Gly Asn Asp Thr Gly Thr Gln Tyr
1               5                   10                  15

Arg Ser Gly Val Tyr Tyr Thr Asp Pro Ala Glu Lys Ala Val Ile Ala
            20                  25                  30

Ala Ala Leu Lys Arg Glu Gln Gln Lys Tyr Gln Leu Pro Leu Val Val
        35                  40                  45

Glu Asn Glu Pro Leu Lys Asn Phe Tyr Asp Ala Glu Tyr His Gln
    50                  55                  60

Asp Tyr Leu Ile Lys Asn Pro Asn Gly Tyr Cys His Ile Asp Ile Arg
65                  70                  75                  80

Lys Ala Asp Glu Pro Leu Pro Gly Lys Thr Lys Ala Ala Pro Gln Gly
                85                  90                  95

```
Gln Arg Leu Arg Arg Gly Gln Arg Ile Lys Asn Arg Val Thr Pro Asn
            100                 105                 110

Ser Asn Ala Pro Asp Arg Arg Ala Ile Pro Ser Asp Gln Asn Ser Ala
        115                 120                 125

Thr Glu Tyr Ala Phe Ser His Glu Tyr Asp His Leu Phe Lys Pro Gly
    130                 135                 140

Ile Tyr Val Asp Val Val Ser Gly Glu Pro Leu Phe Ser Ser Ala Asp
145                 150                 155                 160

Lys Tyr Asp Ser Gly Cys Gly Trp Pro Ser Phe Thr Arg Pro Ile
                165                 170                 175

(2) INFORMATION FOR SEQ ID NO:27:

(i) SEQUENCE CHARACTERISTICS:
        (A) LENGTH: 69 amino acids
        (B) TYPE: amino acid
        (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Streptococcus pneumoniae
        (B) STRAIN: R6

(vii) IMMEDIATE SOURCE:
        (B) CLONE: SPRU39

(xi) SEQUENCE DESCRIPTION: SEQ ID NO:27:

Val Leu Gly Glu Leu Gly Asn Phe Phe Ser Pro Glu Phe Met Asn Arg
1               5                   10                  15

Phe Asp Gly Ile Ile Glu Phe Lys Ala Leu Ser Lys Asp Asn Leu Leu
            20                  25                  30

Gln Ile Val Glu Leu Met Leu Ala Asp Val Asn Lys Arg Leu Ser Ser
        35                  40                  45

Asn Asn Ile Arg Leu Asp Val Thr Asp Lys Val Lys Glu Lys Leu Val
    50                  55                  60

Asp Leu Gly Tyr Asp
65

(2) INFORMATION FOR SEQ ID NO:28:

(i) SEQUENCE CHARACTERISTICS:
        (A) LENGTH: 69 amino acids
        (B) TYPE: amino acid
        (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Lycopersicon esculentum (tomato)

(xi) SEQUENCE DESCRIPTION: SEQ ID NO:28:

Val Thr Glu Glu Leu Lys Gln Tyr Phe Arg Pro Glu Phe Leu Asn Arg
1               5                   10                  15
```

-continued

```
Leu Asp Glu Met Ile Val Phe Arg Gln Leu Thr Lys Leu Glu Val Lys
            20                  25                  30

Glu Ile Ala Asp Ile Met Leu Lys Glu Val Phe Glu Arg Leu Lys Val
            35                  40                  45

Lys Glu Ile Glu Leu Gln Val Thr Glu Arg Phe Arg Asp Arg Val Val
    50                  55                  60

Asp Glu Gly Tyr Asn
65
```

(2) INFORMATION FOR SEQ ID NO:29:

(i) SEQUENCE CHARACTERISTICS:
        (A) LENGTH: 98 amino acids
        (B) TYPE: amino acid
        (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Streptococcus pneumoniae
        (B) STRAIN: R6

(vii) IMMEDIATE SOURCE:
        (B) CLONE: SPRU87

(xi) SEQUENCE DESCRIPTION: SEQ ID NO:29:

```
Asp Asp Gly Ser Gln Ala Val Asn Ile Ile Asn Leu Leu Gly Gly Arg
1               5                   10                  15

Val Asn Ile Val Asp Val Asp Ala Cys Met Thr Arg Leu Arg Val Thr
            20                  25                  30

Val Lys Asp Ala Asp Lys Val Gly Asn Ala Glu Gln Trp Lys Ala Glu
            35                  40                  45

Gly Ala Met Gly Leu Val Met Lys Gly Gln Val Gln Ala Ile Tyr
    50                  55                  60

Gly Pro Lys Ala Asp Ile Leu Lys Ser Asp Ile Gln Asp Ile Leu Asp
65                  70                  75                  80

Ser Gly Glu Ile Ile Pro Glu Thr Leu Pro Ser Gln Met Thr Glu Val
                85                  90                  95

Gln Gln
```

(2) INFORMATION FOR SEQ ID NO:30:

(i) SEQUENCE CHARACTERISTICS:
        (A) LENGTH: 97 amino acids
        (B) TYPE: amino acid
        (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Bacillus subtilis (xi) SEQUENCE DESCRIPTION: SEQ ID NO:30:

```
Glu Ala Gly Asp Leu Pro Tyr Glu Ile Leu Gln Ala Met Gly Asp Gln
1               5                   10                  15
```

```
Glu Asn Ile Lys His Leu Asp Ala Cys Ile Thr Arg Leu Arg Val Thr
             20                  25                  30

Val Asn Asp Gln Lys Lys Val Asp Lys Asp Arg Leu Lys Gln Leu Gly
             35                  40                  45

Ala Ser Gly Val Leu Glu Val Gly Asn Asn Ile Gln Ala Ile Phe Gly
 50                  55                  60

Pro Arg Ser Asp Gly Leu Lys Thr Gln Met Gln Asp Ile Ile Ala Gly
 65                  70                  75                  80

Arg Lys Pro Arg Pro Glu Pro Lys Thr Ser Ala Gln Glu Glu Val Gly
             85                  90                  95

Gln
```

(2) INFORMATION FOR SEQ ID NO:31:

(i) SEQUENCE CHARACTERISTICS:
        (A) LENGTH: 69 amino acids
        (B) TYPE: amino acid
        (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Streptococcus pneumoniae
        (B) STRAIN: R6

(vii) IMMEDIATE SOURCE:
        (B) CLONE: SPRU24

(xi) SEQUENCE DESCRIPTION: SEQ ID NO:31:

```
Asp Gly Arg Met Val Phe Val Leu Pro Arg Glu Asn Lys Thr Tyr Phe
 1               5                  10                  15

Gly Thr Thr Asp Thr Asp Tyr Thr Gly Asp Leu Glu His Pro Lys Val
             20                  25                  30

Thr Gln Glu Asp Val Asp Tyr Leu Leu Gly Ile Val Asn Asn Arg Phe
             35                  40                  45

Pro Glu Ser Asn Ile Thr Ile Asp Asp Ile Glu Ser Ser Trp Ala Gly
 50                  55                  60

Leu Arg Pro Leu Ile
 65
```

(2) INFORMATION FOR SEQ ID NO:32:

(i) SEQUENCE CHARACTERISTICS:
        (A) LENGTH: 69 amino acids
        (B) TYPE: amino acid
        (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Bacillus subtilis (xi) SEQUENCE DESCRIPTION: SEQ ID NO:32:

```
Asp Gly Arg Met Val Phe Ala Ile Pro Arg Glu Gly Lys Thr Tyr Val
1               5                   10                  15

Gly Thr Thr Asp Thr Val Tyr Lys Glu Ala Leu Glu His Pro Arg Met
            20                  25              30

Thr Thr Glu Asp Arg Asp Tyr Val Ile Lys Ser Ile Asn Tyr Met Phe
        35                  40              45

Pro Glu Leu Asn Ile Thr Ala Asn Asp Ile Glu Ser Ser Trp Ala Gly
    50                  55              60

Leu Arg Pro Leu Ile
65
```

(2) INFORMATION FOR SEQ ID NO:33:

(i) SEQUENCE CHARACTERISTICS:
        (A) LENGTH: 41 amino acids
        (B) TYPE: amino acid
        (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Streptococcus pneumoniae
        (B) STRAIN: R6

(vii) IMMEDIATE SOURCE:
        (B) CLONE: SPRU75

(xi) SEQUENCE DESCRIPTION: SEQ ID NO:33:

```
Ala Leu Leu Glu Ile Leu Asp Pro Val Arg Glu Gly Ala Ala Glu Thr
1               5                   10                  15

Leu Asp Tyr Leu Arg Ser Gln Glu Val Gly Leu Lys Ile Ile Ser Gly
            20                  25              30

Val Asn Pro Val Thr Val Ser Ser Ile
        35                  40
```

(2) INFORMATION FOR SEQ ID NO:34:

(i) SEQUENCE CHARACTERISTICS:
        (A) LENGTH: 41 amino acids
        (B) TYPE: amino acid
        (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Streptococcus typhimurium (xi) SEQUENCE DESCRIPTION: SEQ ID NO:34:

```
Gly Met Leu Thr Phe Leu Asp Pro Pro Lys Glu Ser Ala Gly Lys Ala
1               5                   10                  15

Ile Ala Ala Leu Arg Asp Asn Gly Val Ala Val Lys Val Leu Thr Gly
            20                  25              30

Asp Asn Pro Val Val Thr Ala Arg Ile
        35                  40
```

(2) INFORMATION FOR SEQ ID NO:35:

(i) SEQUENCE CHARACTERISTICS:
        (A) LENGTH: 72 amino acids
        (B) TYPE: amino acid
        (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Streptococcus pneumoniae
        (B) STRAIN: R6

(vii) IMMEDIATE SOURCE:
        (B) CLONE: SPRU81

(xi) SEQUENCE DESCRIPTION: SEQ ID NO:35:

```
Gly Thr Leu Arg Lys Asn Ile Gly Leu Val Leu Gln Glu Pro Phe Leu
1               5                   10                  15

Tyr His Gly Thr Ile Lys Ser Asn Ile Ala Met Tyr Gln Glu Ile Ser
                20                  25                  30

Asp Glu Gln Val Gln Ala Ala Ala Phe Val Asp Ala Asp Ser Phe
            35                  40                  45

Ile Gln Glu Leu Pro Gln Gly Tyr Asp Ser Pro Val Ser Glu Arg Gly
        50                  55                  60

Ser Ser Phe Ser Thr Gly Gln Arg
65                  70
```

(2) INFORMATION FOR SEQ ID NO:36:

(i) SEQUENCE CHARACTERISTICS:
        (A) LENGTH: 73 amino acids
        (B) TYPE: amino acid
        (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Bordetella pertussis (xi) SEQUENCE DESCRIPTION: SEQ ID NO:36:

```
Ala Ser Leu Arg Arg Gln Leu Gly Val Val Leu Gln Glu Ser Thr Leu
1               5                   10                  15

Phe Asn Arg Ser Val Arg Asp Asn Ile Ala Leu Thr Arg Pro Gly Ala
                20                  25                  30

Ser Met His Glu Val Val Ala Ala Ala Arg Leu Ala Gly Ala His Glu
            35                  40                  45

Phe Ile Cys Gln Leu Pro Glu Gly Tyr Asp Thr Met Leu Gly Glu Asn
        50                  55                  60

Gly Val Gly Leu Ser Gly Gly Gln Arg
65                  70
```

(2) INFORMATION FOR SEQ ID NO:37:

(i) SEQUENCE CHARACTERISTICS:
        (A) LENGTH: 86 amino acids (B) TYPE: amino acid
            (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
            (A) ORGANISM: Streptococcus pneumoniae
            (B) STRAIN: R6

(vii) IMMEDIATE SOURCE:
            (B) CLONE: SPRU17

(xi) SEQUENCE DESCRIPTION: SEQ ID NO:37:

Gln Ile Lys Ala Leu Lys Ser Gly Ala His Ile Val Val Gly Thr Pro
1               5                   10                  15

Gly Arg Leu Leu Asp Leu Ile Lys Arg Lys Ala Leu Lys Leu Gln Asp
                20                  25                  30

Ile Glu Thr Leu Ile Leu Asp Glu Ala Asp Glu Met Leu Asn Met Gly
            35                  40                  45

Phe Leu Glu Asp Ile Glu Ala Ile Ile Ser Arg Val Pro Glu Asn Arg
        50                  55                  60

Gln Thr Leu Leu Phe Ser Ala Thr Met Pro Asp Ala Ile Lys Arg Ile
65                  70                  75                  80

Gly Val Gln Phe Met Lys
                85

(2) INFORMATION FOR SEQ ID NO:38:

(i) SEQUENCE CHARACTERISTICS:
            (A) LENGTH: 86 amino acids
            (B) TYPE: amino acid
            (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
            (A) ORGANISM: Escherichia coli (xi) SEQUENCE DESCRIPTION: SEQ ID NO:38:

Gln Leu Arg Ala Leu Arg Gln Gly Pro Gln Ile Val Val Gly Thr Pro
1               5                   10                  15

Gly Arg Leu Leu Asp His Leu Lys Arg Gly Thr Leu Asp Leu Ser Lys
                20                  25                  30

Leu Ser Gly Leu Val Leu Asp Glu Ala Asp Glu Met Leu Arg Met Gly
            35                  40                  45

Phe Ile Glu Asp Val Glu Thr Ile Met Ala Gln Ile Pro Glu Gly His
        50                  55                  60

Gln Thr Ala Leu Phe Ser Ala Thr Met Pro Glu Ala Ile Arg Arg Ile
65                  70                  75                  80

Thr Arg Arg Phe Met Lys
                85

(2) INFORMATION FOR SEQ ID NO:39:

(i) SEQUENCE CHARACTERISTICS:
        (A) LENGTH: 78 amino acids
        (B) TYPE: amino acid
        (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Escherichia coli (xi) SEQUENCE DESCRIPTION: SEQ ID NO:39:

Ala Ile Ile Phe Val Arg Thr Lys Asn Ala Thr Leu Glu Val Ala Glu
1               5                  10                  15

Ala Leu Glu Arg Asn Gly Tyr Asn Ser Ala Ala Leu Asn Gly Asp Met
            20                  25                  30

Asn Gln Ala Leu Arg Glu Gln Thr Leu Glu Arg Leu Lys Asp Gly Arg
        35                  40                  45

Leu Asp Ile Leu Ile Ala Thr Asp Val Ala Ala Arg Gly Leu Asp Val
50                  55                  60

Glu Arg Ile Ser Leu Val Val Asn Tyr Asp Ile Pro Met Asp
65                  70                  75

(2) INFORMATION FOR SEQ ID NO:40:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pneumoniae (xi) SEQUENCE DESCRIPTION: SEQ ID NO:40:

AAAGGATCCA TGAARAARAA YMGHGTNTTY                                              30

(2) INFORMATION FOR SEQ ID NO:41:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pneumoniae (xi) SEQUENCE DESCRIPTION: SEQ ID NO:41:

TTTGGATCCG TTGGTTTAGC AAAATCGCTT                                              30

(2) INFORMATION FOR SEQ ID NO:42:

```
    (i) SEQUENCE CHARACTERISTICS:
        (A) LENGTH: 15 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pneumoniae (xi) SEQUENCE DESCRIPTION: SEQ ID NO:42:

AATATCGCCC TGAGC                                                    15

(2) INFORMATION FOR SEQ ID NO:43:

(i) SEQUENCE CHARACTERISTICS:
        (A) LENGTH: 17 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pneumoniae (xi) SEQUENCE DESCRIPTION: SEQ ID NO:43:

ATCACGCAGA GCGGCAG                                                  17

(2) INFORMATION FOR SEQ ID NO:44:

(i) SEQUENCE CHARACTERISTICS:
        (A) LENGTH: 52 amino acids
        (B) TYPE: amino acid
        (D) TOPOLOGY: unknown (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: Streptococcus pneumoniae (xi) SEQUENCE DESCRIPTION: SEQ ID NO:44:

Met Lys His Leu Leu Ser Tyr Phe Lys Pro Tyr Ile Lys Glu Ser Ile
1               5                   10                  15

Leu Ala Pro Leu Phe Lys Leu Leu Glu Ala Val Phe Glu Leu Leu Val
            20                  25                  30

Pro Met Val Ile Ala Gly Ile Val Asp Gln Ser Leu Pro Gln Gly Asp
        35                  40                  45

Pro Arg Val Pro
    50

(2) INFORMATION FOR SEQ ID NO:45:

(i) SEQUENCE CHARACTERISTICS:
        (A) LENGTH: 56 amino acids
        (B) TYPE: amino acid
```

(D) TOPOLOGY: unknown (ii) MOLECULE TYPE: peptide (iii) HYPOTHETICAL: NO (iv) ANTI-SENSE: NO (v) FRAGMENT TYPE: N-terminal (vi) ORIGINAL SOURCE:
         (A) ORGANISM: Streptococcus pneumoniae (xi) SEQUENCE DESCRIPTION: SEQ ID NO:45:

Met Ala Lys Asn Asn Lys Val Ala Val Val Thr Thr Val Pro Ser Val
1               5                  10                  15

Ala Glu Gly Leu Lys Asn Val Asn Gly Val Asn Phe Asp Tyr Lys Asp
            20                  25                  30

Glu Ala Ser Ala Lys Glu Ala Ile Lys Glu Glu Lys Leu Lys Gly Tyr
        35                  40                  45

Leu Thr Ile Asp Pro Arg Val Pro
50                  55

(2) INFORMATION FOR SEQ ID NO:46:

(i) SEQUENCE CHARACTERISTICS:
         (A) LENGTH: 2019 base pairs
         (B) TYPE: nucleic acid
         (C) STRANDEDNESS: both
         (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Streptococcus pneumoniae
         (B) STRAIN: R6

(vii) IMMEDIATE SOURCE:
         (B) CLONE: SPRU98

(ix) FEATURE:
         (A) NAME/KEY: CDS
         (B) LOCATION: 1..1932

(xi) SEQUENCE DESCRIPTION: SEQ ID NO:46:

GGT GTA CTT GCA GCA TGC TCT GGA TCA GGT TCA AGC GCT AAA GGT GAG        48
Gly Val Leu Ala Ala Cys Ser Gly Ser Gly Ser Ser Ala Lys Gly Glu
1               5                  10                  15

AAG ACA TTC TCA TAC ATT TAT GAG ACA GAC CCT GAT AAC CTC AAC TAT        96
Lys Thr Phe Ser Tyr Ile Tyr Glu Thr Asp Pro Asp Asn Leu Asn Tyr
            20                  25                  30

TTG ACA ACT GCT AAG GCT GCG ACA GCA AAT ATT ACC AGT AAC GTG GTT       144
Leu Thr Thr Ala Lys Ala Ala Thr Ala Asn Ile Thr Ser Asn Val Val
        35                  40                  45

GAT GGT TTG CTA GAA AAT GAT CGC TAC GGG AAC TTT GTG CCG TCT ATG       192
Asp Gly Leu Leu Glu Asn Asp Arg Tyr Gly Asn Phe Val Pro Ser Met
50                  55                  60

GCT GAG GAT TGG TCT GTA TCC AAG GAT GGA TTG ACT TAC ACT TAT ACT       240
Ala Glu Asp Trp Ser Val Ser Lys Asp Gly Leu Thr Tyr Thr Tyr Thr
65                  70                  75                  80

ATC CGT AAG GAT GCA AAA TGG TAT ACT TCT GAA GGT GAA GAA TAC GCG       288
Ile Arg Lys Asp Ala Lys Trp Tyr Thr Ser Glu Gly Glu Glu Tyr Ala
                85                  90                  95

```
GCA GTC AAA GCT CAA GAC TTT GTA ACA GGA CTA AAA TAT GCT GCT GAT       336
Ala Val Lys Ala Gln Asp Phe Val Thr Gly Leu Lys Tyr Ala Ala Asp
            100                 105                 110

AAA AAA TCA GAT GCT CTT TAC CCT GTT CAA GAA TCA ATC AAA GGG TTG       384
Lys Lys Ser Asp Ala Leu Tyr Pro Val Gln Glu Ser Ile Lys Gly Leu
            115                 120                 125

GAT GCC TAT GTA AAA GGG GAA ATC AAA GAT TTC TCA CAA GTA GGA ATT       432
Asp Ala Tyr Val Lys Gly Glu Ile Lys Asp Phe Ser Gln Val Gly Ile
        130                 135                 140

AAG GCT CTG GAT GAA CAG ACA GTT CAG TAC ACT TTG AAC AAA CCA GAA       480
Lys Ala Leu Asp Glu Gln Thr Val Gln Tyr Thr Leu Asn Lys Pro Glu
145                 150                 155                 160

AGC TTC TGG AAT TCT AAG ACA ACC ATG GGT GTG CTT GCG CCA GTT AAT       528
Ser Phe Trp Asn Ser Lys Thr Thr Met Gly Val Leu Ala Pro Val Asn
                165                 170                 175

GAA GAG TTT TTG AAT TCA AAA GGA GAT GAT TTT GCC AAA GCT ACG GAT       576
Glu Glu Phe Leu Asn Ser Lys Gly Asp Asp Phe Ala Lys Ala Thr Asp
            180                 185                 190

CCA AGT AGT CTC TTG TAT AAC GGT CCT TAT TTG TTG AAA TCC ATT GTG       624
Pro Ser Ser Leu Leu Tyr Asn Gly Pro Tyr Leu Leu Lys Ser Ile Val
            195                 200                 205

ACC AAA TCC TCT GTT GAA TTT GCG AAA AAT CCG AAC TAC TGG GAT AAG       672
Thr Lys Ser Ser Val Glu Phe Ala Lys Asn Pro Asn Tyr Trp Asp Lys
        210                 215                 220

GAC AAT GTG CAT ATT GAC AAA GTT AAA TTG TCA TTC TGG GAT GGT CAA       720
Asp Asn Val His Ile Asp Lys Val Lys Leu Ser Phe Trp Asp Gly Gln
225                 230                 235                 240

GAT ACC AGC AAA CCT GCA GAA AAC TTT AAA GAT GGT AGC CTT ACA GCA       768
Asp Thr Ser Lys Pro Ala Glu Asn Phe Lys Asp Gly Ser Leu Thr Ala
                245                 250                 255

GCT CGT CTC TAT CCA ACA AGT GCA AGT TTC GCA GAG CTT GAG AAG AGT       816
Ala Arg Leu Tyr Pro Thr Ser Ala Ser Phe Ala Glu Leu Glu Lys Ser
            260                 265                 270

ATG AAG GAC AAT ATT GTC TAT ACT CAA CAA GAC TCT ATT ACG TAT CTA       864
Met Lys Asp Asn Ile Val Tyr Thr Gln Gln Asp Ser Ile Thr Tyr Leu
            275                 280                 285

GTC GGT ACA AAT ATT GAC CGT CAG TCC TAT AAA TAC ACA TCT AAG ACC       912
Val Gly Thr Asn Ile Asp Arg Gln Ser Tyr Lys Tyr Thr Ser Lys Thr
        290                 295                 300

AGC GAT GAA CAA AAG GCA TCG ACT AAA AAG GCT CTC TTA AAC AAG GAT       960
Ser Asp Glu Gln Lys Ala Ser Thr Lys Lys Ala Leu Leu Asn Lys Asp
305                 310                 315                 320

TTC CGT CAG GCT ATT GCC TTT GGT TTT GAT CGT ACA GCC TAT GCC TCT      1008
Phe Arg Gln Ala Ile Ala Phe Gly Phe Asp Arg Thr Ala Tyr Ala Ser
                325                 330                 335

CAG TTG AAT GGA CAA ACT GGA GCA AGT AAA ATC TTG CGT AAT CTC TTT      1056
Gln Leu Asn Gly Gln Thr Gly Ala Ser Lys Ile Leu Arg Asn Leu Phe
            340                 345                 350

GTG CCA CCA ACA TTT GTT CAA GCA GAT GGT AAA AAC TTT GGC GAT ATG      1104
Val Pro Pro Thr Phe Val Gln Ala Asp Gly Lys Asn Phe Gly Asp Met
            355                 360                 365

GTC AAA GAG AAA TTG GTC ACT TAT GGG GAT GAA TGG AAG GAT GTT AAT      1152
Val Lys Glu Lys Leu Val Thr Tyr Gly Asp Glu Trp Lys Asp Val Asn
        370                 375                 380

CTT GCA GAT TCT CAG GAT GGT CTT TAC AAT CCA GAA AAA GCC AAG GCT      1200
Leu Ala Asp Ser Gln Asp Gly Leu Tyr Asn Pro Glu Lys Ala Lys Ala
385                 390                 395                 400

GAA TTT GCT AAA GCT AAA TCA GCC TTA CAA GCA GAA GGT GTG ACA TTC      1248
Glu Phe Ala Lys Ala Lys Ser Ala Leu Gln Ala Glu Gly Val Thr Phe
                405                 410                 415
```

| | | | | |
|---|---|---|---|---|
| CCA ATT CAT TTG GAT ATG CCA GTT GAC CAG ACA GCA ACT ACA AAA GTT | | | | 1296 |
| Pro Ile His Leu Asp Met Pro Val Asp Gln Thr Ala Thr Thr Lys Val | | | | |
| 420 425 430 | | | | |
| | | | | |
| CAG CGC GTC CAA TCT ATG AAA CAA TCC TTG GAA GCA ACT TTA GGA GCT | | | | 1344 |
| Gln Arg Val Gln Ser Met Lys Gln Ser Leu Glu Ala Thr Leu Gly Ala | | | | |
| 435 440 445 | | | | |
| | | | | |
| GAT AAT GTC ATT ATT GAT ATT CAA CAA CTA CAA AAA GAC GAA GTA AAC | | | | 1392 |
| Asp Asn Val Ile Ile Asp Ile Gln Gln Leu Gln Lys Asp Glu Val Asn | | | | |
| 450 455 460 | | | | |
| | | | | |
| AAT ATT ACA TAT TTT GCT GAA AAT GCT GCT GGC GAA GAC TGG GAT TTA | | | | 1440 |
| Asn Ile Thr Tyr Phe Ala Glu Asn Ala Ala Gly Glu Asp Trp Asp Leu | | | | |
| 465 470 475 480 | | | | |
| | | | | |
| TCA GAT AAT GTC GGT TGG GGT CCA GAC TTT GCC GAT CCA TCA ACC TAC | | | | 1488 |
| Ser Asp Asn Val Gly Trp Gly Pro Asp Phe Ala Asp Pro Ser Thr Tyr | | | | |
| 485 490 495 | | | | |
| | | | | |
| CTT GAT ATC ATC AAA CCA TCT GTA GGA GAA AGT ACT AAA ACA TAT TTA | | | | 1536 |
| Leu Asp Ile Ile Lys Pro Ser Val Gly Glu Ser Thr Lys Thr Tyr Leu | | | | |
| 500 505 510 | | | | |
| | | | | |
| GGG TTT GAC TCA GGG GAA GAT AAT GTA GCT GCT AAA AAA GTA GGT CTA | | | | 1584 |
| Gly Phe Asp Ser Gly Glu Asp Asn Val Ala Ala Lys Lys Val Gly Leu | | | | |
| 515 520 525 | | | | |
| | | | | |
| TAT GAC TAC GAA AAA TTG GTT ACT GAG GCT GGT GAT GAG ACT ACA GAT | | | | 1632 |
| Tyr Asp Tyr Glu Lys Leu Val Thr Glu Ala Gly Asp Glu Thr Thr Asp | | | | |
| 530 535 540 | | | | |
| | | | | |
| GTT GCT AAA CGC TAT GAT AAA TAC GCT GCA GCC CAA GCT TGG TTG ACA | | | | 1680 |
| Val Ala Lys Arg Tyr Asp Lys Tyr Ala Ala Ala Gln Ala Trp Leu Thr | | | | |
| 545 550 555 560 | | | | |
| | | | | |
| GAT AGT GCT TTG ATT ATT CCA ACT ACA TCT CGT ACA GGG CGT CCA ATC | | | | 1728 |
| Asp Ser Ala Leu Ile Ile Pro Thr Thr Ser Arg Thr Gly Arg Pro Ile | | | | |
| 565 570 575 | | | | |
| | | | | |
| TTG TCT AAG ATG GTA CCA TTT ACA ATA CCA TTT GCA TTG TCA GGA AAT | | | | 1776 |
| Leu Ser Lys Met Val Pro Phe Thr Ile Pro Phe Ala Leu Ser Gly Asn | | | | |
| 580 585 590 | | | | |
| | | | | |
| AAA GGT ACA AGT GAA CCA GTC TTG TAT AAA TAC TTG GAA CTT CAA GAC | | | | 1824 |
| Lys Gly Thr Ser Glu Pro Val Leu Tyr Lys Tyr Leu Glu Leu Gln Asp | | | | |
| 595 600 605 | | | | |
| | | | | |
| AAG GCA GTC ACT GTA GAT GAA TAC CAA AAA GCT CAG GAA AAA TGG ATG | | | | 1872 |
| Lys Ala Val Thr Val Asp Glu Tyr Gln Lys Ala Gln Glu Lys Trp Met | | | | |
| 610 615 620 | | | | |
| | | | | |
| AAA GAA AAA GAA GAG TCT AAT AAA AAG GCT CAA GAA GAT CTC GCA AAA | | | | 1920 |
| Lys Glu Lys Glu Glu Ser Asn Lys Lys Ala Gln Glu Asp Leu Ala Lys | | | | |
| 625 630 635 640 | | | | |
| | | | | |
| CAT GTG AAA TAACTGTTGC AAAATATAAG AAAGGATTTA GTATTCTCT | | | | 1969 |
| His Val Lys | | | | |
| | | | | |
| TGAATGCTGA ATCCTTTTTT ACATTTGTAA AGAAAGATTC TAAATGTACT | | | | 2019 |

(2) INFORMATION FOR SEQ ID NO:47:

(i) SEQUENCE CHARACTERISTICS:
        (A) LENGTH: 643 amino acids
        (B) TYPE: amino acid
        (D) TOPOLOGY: linear (ii) MOLECULE TYPE: protein (xi) SEQUENCE DESCRIPTION: SEQ ID NO:47:

Gly Val Leu Ala Ala Cys Ser Gly Ser Gly Ser Ser Ala Lys Gly Glu
1               5                   10                  15

Lys Thr Phe Ser Tyr Ile Tyr Glu Thr Asp Pro Asp Asn Leu Asn Tyr
            20                  25                  30

-continued

```
Leu Thr Thr Ala Lys Ala Ala Thr Ala Asn Ile Thr Ser Asn Val Val
         35                  40                  45

Asp Gly Leu Leu Glu Asn Asp Arg Tyr Gly Asn Phe Val Pro Ser Met
 50                  55                  60

Ala Glu Asp Trp Ser Val Ser Lys Asp Gly Leu Thr Tyr Thr Tyr Thr
 65                  70                  75                  80

Ile Arg Lys Asp Ala Lys Trp Tyr Thr Ser Glu Gly Glu Tyr Ala
                 85                  90                  95

Ala Val Lys Ala Gln Asp Phe Val Thr Gly Leu Lys Tyr Ala Ala Asp
                100                 105                 110

Lys Lys Ser Asp Ala Leu Tyr Pro Val Gln Glu Ser Ile Lys Gly Leu
                115                 120                 125

Asp Ala Tyr Val Lys Gly Glu Ile Lys Asp Phe Ser Gln Val Gly Ile
130                 135                 140

Lys Ala Leu Asp Glu Gln Thr Val Gln Tyr Thr Leu Asn Lys Pro Glu
145                 150                 155                 160

Ser Phe Trp Asn Ser Lys Thr Thr Met Gly Val Leu Ala Pro Val Asn
                165                 170                 175

Glu Glu Phe Leu Asn Ser Lys Gly Asp Asp Phe Ala Lys Ala Thr Asp
                180                 185                 190

Pro Ser Ser Leu Leu Tyr Asn Gly Pro Tyr Leu Leu Lys Ser Ile Val
                195                 200                 205

Thr Lys Ser Ser Val Glu Phe Ala Lys Asn Pro Asn Tyr Trp Asp Lys
210                 215                 220

Asp Asn Val His Ile Asp Lys Val Lys Leu Ser Phe Trp Asp Gly Gln
225                 230                 235                 240

Asp Thr Ser Lys Pro Ala Glu Asn Phe Lys Asp Gly Ser Leu Thr Ala
                245                 250                 255

Ala Arg Leu Tyr Pro Thr Ser Ala Ser Phe Ala Glu Leu Glu Lys Ser
                260                 265                 270

Met Lys Asp Asn Ile Val Tyr Thr Gln Gln Asp Ser Ile Thr Tyr Leu
                275                 280                 285

Val Gly Thr Asn Ile Asp Arg Gln Ser Tyr Lys Tyr Thr Ser Lys Thr
                290                 295                 300

Ser Asp Glu Gln Lys Ala Ser Thr Lys Lys Ala Leu Leu Asn Lys Asp
305                 310                 315                 320

Phe Arg Gln Ala Ile Ala Phe Gly Phe Asp Arg Thr Ala Tyr Ala Ser
                325                 330                 335

Gln Leu Asn Gly Gln Thr Gly Ala Ser Lys Ile Leu Arg Asn Leu Phe
                340                 345                 350

Val Pro Pro Thr Phe Val Gln Ala Asp Gly Lys Asn Phe Gly Asp Met
                355                 360                 365

Val Lys Glu Lys Leu Val Thr Tyr Gly Asp Glu Trp Lys Asp Val Asn
370                 375                 380

Leu Ala Asp Ser Gln Asp Gly Leu Tyr Asn Pro Glu Lys Ala Lys Ala
385                 390                 395                 400

Glu Phe Ala Lys Ala Lys Ser Ala Leu Gln Ala Glu Gly Val Thr Phe
                405                 410                 415

Pro Ile His Leu Asp Met Pro Val Asp Gln Thr Ala Thr Thr Lys Val
                420                 425                 430

Gln Arg Val Gln Ser Met Lys Gln Ser Leu Glu Ala Thr Leu Gly Ala
                435                 440                 445

Asp Asn Val Ile Ile Asp Ile Gln Gln Leu Gln Lys Asp Glu Val Asn
450                 455                 460
```

```
Asn Ile Thr Tyr Phe Ala Glu Asn Ala Ala Gly Glu Asp Trp Asp Leu
465                 470                 475                 480

Ser Asp Asn Val Gly Trp Gly Pro Asp Phe Ala Asp Pro Ser Thr Tyr
                485                 490                 495

Leu Asp Ile Ile Lys Pro Ser Val Gly Glu Ser Thr Lys Thr Tyr Leu
                500                 505                 510

Gly Phe Asp Ser Gly Glu Asp Asn Val Ala Ala Lys Lys Val Gly Leu
                515                 520                 525

Tyr Asp Tyr Glu Lys Leu Val Thr Glu Ala Gly Asp Glu Thr Thr Asp
530                 535                 540

Val Ala Lys Arg Tyr Asp Lys Tyr Ala Ala Gln Ala Trp Leu Thr
545                 550                 555                 560

Asp Ser Ala Leu Ile Ile Pro Thr Thr Ser Arg Thr Gly Arg Pro Ile
                565                 570                 575

Leu Ser Lys Met Val Pro Phe Thr Ile Pro Phe Ala Leu Ser Gly Asn
                580                 585                 590

Lys Gly Thr Ser Glu Pro Val Leu Tyr Lys Tyr Leu Glu Leu Gln Asp
                595                 600                 605

Lys Ala Val Thr Val Asp Glu Tyr Gln Lys Ala Gln Glu Lys Trp Met
610                 615                 620

Lys Glu Lys Glu Glu Ser Asn Lys Lys Ala Gln Glu Asp Leu Ala Lys
625                 630                 635                 640

His Val Lys (2) INFORMATION FOR SEQ ID NO:48:

(i) SEQUENCE CHARACTERISTICS:
        (A) LENGTH: 642 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (A) ORGANISM: Streptococcus pneumoniae (vii) IMMEDIATE SOURCE:
        (B) CLONE: amiA (ix) FEATURE:
        (D) OTHER INFORMATION: *** note: the reference contains a
            sequence error; the correct sequence shown below is
            obtained from GENBANK ****

(x) PUBLICATION INFORMATION:
        (A) AUTHORS: Alloing, et al.
        (C) JOURNAL: Mol. Microbiol.
        (D) VOLUME: 4
        (F) PAGES: 633-644
        (G) DATE: 1990

(xi) SEQUENCE DESCRIPTION: SEQ ID NO:48:

Gly Val Leu Ala Ala Cys Ser Ser Ser Lys Ser Ser Asp Ser Ser Ala
1               5                   10                  15

Pro Lys Ala Tyr Gly Tyr Val Tyr Thr Ala Asp Pro Glu Thr Leu Asp
                20                  25                  30

Tyr Leu Ile Ser Arg Lys Asn Ser Thr Thr Val Val Thr Ser Asn Gly
                35                  40                  45
```

-continued

```
Ile Asp Gly Leu Phe Thr Asn Asp Asn Tyr Gly Asn Leu Ala Pro Ala
 50                  55                  60

Val Ala Glu Asp Trp Glu Val Ser Lys Asp Gly Leu Thr Tyr Thr Tyr
 65                  70                  75                  80

Lys Ile Arg Lys Gly Val Lys Trp Phe Thr Ser Asp Gly Glu Glu Tyr
                 85                  90                  95

Ala Glu Val Thr Ala Lys Asp Phe Val Asn Gly Leu Lys His Ala Ala
                100                 105                 110

Asp Lys Lys Ser Glu Ala Met Tyr Leu Ala Glu Asn Ser Val Lys Gly
            115                 120                 125

Leu Ala Asp Tyr Leu Ser Gly Thr Ser Thr Asp Phe Ser Thr Val Gly
130                 135                 140

Val Lys Ala Val Asp Asp Tyr Thr Leu Gln Tyr Thr Leu Asn Gln Pro
145                 150                 155                 160

Glu Pro Phe Trp Asn Ser Lys Leu Thr Tyr Ser Ile Phe Trp Pro Leu
                165                 170                 175

Asn Glu Glu Phe Glu Thr Ser Lys Gly Ser Asp Phe Ala Lys Pro Thr
                180                 185                 190

Asp Pro Thr Ser Leu Leu Tyr Asn Gly Pro Phe Leu Leu Lys Gly Leu
            195                 200                 205

Thr Ala Lys Ser Ser Val Glu Phe Val Lys Asn Glu Gln Tyr Trp Asp
210                 215                 220

Lys Glu Asn Val His Leu Asp Thr Ile Asn Leu Ala Tyr Tyr Asp Gly
225                 230                 235                 240

Ser Asp Gln Glu Ser Leu Glu Arg Asn Phe Thr Ser Gly Ala Tyr Ser
                245                 250                 255

Tyr Ala Arg Leu Tyr Pro Thr Ser Ser Asn Tyr Ser Lys Val Ala Glu
            260                 265                 270

Glu Tyr Lys Asp Asn Ile Tyr Tyr Thr Gln Ser Gly Ser Gly Ile Ala
            275                 280                 285

Gly Leu Gly Val Asn Ile Asp Arg Gln Ser Tyr Asn Tyr Thr Ser Lys
290                 295                 300

Thr Thr Asp Ser Glu Lys Val Ala Thr Lys Ala Leu Leu Asn Lys
305                 310                 315                 320

Asp Phe Arg Gln Ala Leu Asn Phe Ala Leu Asp Arg Ser Ala Tyr Ser
                325                 330                 335

Ala Gln Ile Asn Gly Lys Asp Gly Ala Ala Leu Ala Val Arg Asn Leu
            340                 345                 350

Phe Val Lys Pro Asp Phe Val Ser Ala Gly Glu Lys Thr Phe Gly Asp
            355                 360                 365

Leu Val Ala Ala Gln Leu Pro Ala Tyr Gly Asp Glu Trp Lys Gly Val
370                 375                 380

Asn Leu Ala Asp Gly Gln Asp Gly Leu Phe Asn Ala Asp Lys Ala Lys
385                 390                 395                 400

Ala Glu Phe Arg Lys Ala Lys Lys Ala Leu Glu Ala Asp Gly Val Gln
                405                 410                 415

Phe Pro Ile His Leu Asp Val Pro Val Asp Gln Ala Ser Lys Asn Tyr
            420                 425                 430

Ile Ser Arg Ile Gln Ser Phe Lys Gln Ser Val Glu Thr Val Leu Gly
            435                 440                 445

Val Glu Asn Val Val Asp Ile Gln Gln Met Thr Ser Asp Glu Phe
450                 455                 460

Leu Asn Ile Thr Tyr Tyr Ala Ala Asn Ala Ser Ser Glu Asp Trp Asp
465                 470                 475                 480
```

```
Val Ser Gly Gly Val Ser Trp Gly Pro Asp Tyr Gln Asp Pro Ser Thr
                485                 490                 495

Tyr Leu Asp Ile Leu Lys Thr Thr Ser Ser Glu Thr Thr Lys Thr Tyr
            500                 505                 510

Leu Gly Phe Asp Asn Pro Asn Ser Pro Ser Val Val Gln Val Gly Leu
            515                 520                 525

Lys Glu Tyr Asp Lys Leu Val Asp Glu Ala Ala Lys Glu Thr Ser Asp
            530                 535                 540

Phe Asn Val Arg Tyr Glu Lys Tyr Ala Ala Gln Ala Trp Leu Thr
545                 550                 555                 560

Asp Ser Ser Leu Phe Ile Pro Ala Met Ala Ser Ser Gly Ala Ala Pro
                565                 570                 575

Val Leu Ser Arg Ile Val Pro Phe Thr Gly Ala Ser Ala Gln Thr Gly
                580                 585                 590

Ser Lys Gly Ser Asp Val Tyr Phe Lys Tyr Leu Lys Leu Gln Asp Lys
            595                 600                 605

Ala Val Thr Lys Glu Glu Tyr Glu Lys Ala Arg Glu Lys Trp Leu Lys
            610                 615                 620

Glu Lys Ala Glu Ser Asn Glu Lys Ala Gln Lys Glu Leu Ala Ser His
625                 630                 635                 640

Val Lys
```

(2) INFORMATION FOR SEQ ID NO:49:

(i) SEQUENCE CHARACTERISTICS:
        (A) LENGTH: 27 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:49:

GCCGGATCCG GWGTWCTTGC WGCWTGC                                  27

(2) INFORMATION FOR SEQ ID NO:50:

(i) SEQUENCE CHARACTERISTICS:
        (A) LENGTH: 21 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:50:

TACAAGAGAC TACTTGGATC C                                        21

(2) INFORMATION FOR SEQ ID NO:51:

(i) SEQUENCE CHARACTERISTICS:
        (A) LENGTH: 30 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:51:

ACCGGATCCT GCCAACAAGC CTAAATATTC                      30

(2) INFORMATION FOR SEQ ID NO:52:

(i) SEQUENCE CHARACTERISTICS:
      (A) LENGTH: 30 base pairs
      (B) TYPE: nucleic acid
      (C) STRANDEDNESS: both
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:52:

TTTGGATCCG TTGGTTTAGC AAAATCGCTT                      30

(2) INFORMATION FOR SEQ ID NO:53:

(i) SEQUENCE CHARACTERISTICS:
      (A) LENGTH: 18 base pairs
      (B) TYPE: nucleic acid
      (C) STRANDEDNESS: both
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:53:

CTATACCTTG GTTCCTCG                                   18

(2) INFORMATION FOR SEQ ID NO:54:

(i) SEQUENCE CHARACTERISTICS:
      (A) LENGTH: 26 base pairs
      (B) TYPE: nucleic acid
      (C) STRANDEDNESS: both
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:54:

TTTGGATTCG GAATTTCACG AGTAGC                          26

(2) INFORMATION FOR SEQ ID NO:55:

(i) SEQUENCE CHARACTERISTICS:
      (A) LENGTH: 260 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vi) ORIGINAL SOURCE:
               (A) ORGANISM: Streptococcus pneumoniae
               (B) STRAIN: R6

(vii) IMMEDIATE SOURCE:
               (B) CLONE: pad1

(xi) SEQUENCE DESCRIPTION: SEQ ID NO:55:

TTGAGCAGAT TTTAGAAAAG TCAGCATAAT ATGATACAGG TGGAATAGTA AAAATTTGGA      60

GAACGTTTCC AATTCTATGT ATCGGTATTC TCCAAGTTTA AAAAAATTGA AGGAGAGTTA     120

TCATTATGAC TCAAGGGAAA ATTACTGCAT CTGCAGCAAT GCTTAACGTA TTGAAAACAT     180

GGGGCGTAGA TACAATCTAC GGTATCCCAT CAGGAACACT CAGTCATTGA TGGACGCTTT     240

GGCTGAAGAC AAAGATATCC                                                 260

(2) INFORMATION FOR SEQ ID NO:56:

(i) SEQUENCE CHARACTERISTICS:
               (A) LENGTH: 45 amino acids
               (B) TYPE: amino acid
               (C) STRANDEDNESS: single
               (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
               (A) ORGANISM: Streptococcus pneumoniae
               (B) STRAIN: R6

(vii) IMMEDIATE SOURCE:
               (B) CLONE: pad1

(xi) SEQUENCE DESCRIPTION: SEQ ID NO:56:

Met Thr Gln Gly Lys Ile Thr Ala Ser Ala Ala Met Leu Asn Val Leu
1               5                   10                  15

Lys Thr Trp Gly Val Asp Thr Ile Tyr Gly Ile Pro Ser Gly Thr Leu
            20                  25                  30

Ser Ser Leu Met Asp Ala Leu Ala Glu Asp Lys Asp Ile
        35                  40                  45

(2) INFORMATION FOR SEQ ID NO:57:

(i) SEQUENCE CHARACTERISTICS:
               (A) LENGTH: 993 base pairs
               (B) TYPE: nucleic acid
               (C) STRANDEDNESS: double
               (D) TOPOLOGY: linear (ii) MOLECULE TYPE: cDNA (iii) HYPOTHETICAL: NO (iv) ANTI-SENSE: NO (vi) ORIGINAL SOURCE:
               (A) ORGANISM: Streptococcus pneumoniae
               (B) STRAIN: R6

(vii) IMMEDIATE SOURCE:
               (B) CLONE: pad1

(xi) SEQUENCE DESCRIPTION: SEQ ID NO:57:

```
AAGTCCGCCA CGAAGAGACA GGTGCTCTTG CATTCGGTTA TGCAAGCTAA ATTCGGCGGC      60

TCAATCGGGG TTGCAGTTGG TTCAGGTGGT CCAGGTGCGA CTCACTTGAT TAACGGTGTT     120

TACGATGCAG CTATGGATAA CACTCCATTC CTAGCGATCC TTGGATCACG TCCAGTTAAC     180

GAATTGAACA TGGATGCTTT CCAAGAGCTT AACCAAAACC AATGTACAAC GGTATCGCTG     240

TTTACAACAA ACGTGTAGCT TACGCTGAGC AATTGCCAAA AGTAATTGAC GAAGCCTGCC     300

GTGCTGCAAT TTCTAAAAAA GGTCCAGCTG TTGTTGAAAT TCCAGTAAAC TTCGGTTTCC     360

AAGAAATCGA CGAAAACTCA TACTACGGTT CAGGTTCATA CGAACGCTCA TTCATCGCTC     420

CTGCTTTGAA CGAAGTTGAA ATCGACAAAG CTGTTGAAAT CTTGAACAAT GCTGAACGCC     480

CAGTTATCTA TGCTGGATTT GGTGGTGTTA AGCTGGTGA AGTGATTACT GAATTGTCAC      540

GTAAAATCAA AGCACCAATC ATCACAACTG GTAAAAACTT TGAAGCTTTC GAATGGAACT     600

ATGAAGGTTT GACAGGTTCT GCTTACCGTG TTGGTTGGAA ACCAGCCAAC GAAGTGGTCT     660

TTGAAGCAGA CACAGTTCTT TTCCTTGGTT CAAACTTCGC ATTTGCTGAA GTTTACGAAG     720

CATTCAAGAA CACTGAAAAA TTCATACAAG TCGATATCGA CCCTTACAAA CTTGGTAAAC     780

GTCATGCCCT TGACGCTTCA ATCCTTGGTG ATGCTGGTCA AGCAGCTAAA GCTATCCTTG     840

ACAAAGTAAA CCCAGTTGAA TCAACTCCAT GGTGGCGTGC AAACGTTAAG AACAACCAAA     900

ACTGGCGTGA TTACATGAAC AAACTCGAAG GTAAAACTGA GGGTGAATTG CAATTGTATC     960

AAGTTTACAA TGCAATCAAC AAACATGCTG ATC                                  993
```

(2) INFORMATION FOR SEQ ID NO:58:

(i) SEQUENCE CHARACTERISTICS:
        (A) LENGTH: 331 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
       (A) ORGANISM: Streptococcus pneumoniae
       (B) STRAIN: R6

(vii) IMMEDIATE SOURCE:
       (B) CLONE: pad1

(xi) SEQUENCE DESCRIPTION: SEQ ID NO:58:

```
Lys Ser Ala Thr Lys Arg Gln Val Leu Leu His Ser Val Met Gln Ala
 1               5                  10                  15

Lys Phe Gly Gly Ser Ile Gly Val Ala Val Gly Ser Gly Gly Pro Gly
            20                  25                  30

Ala Thr His Leu Ile Asn Gly Val Tyr Asp Ala Ala Met Asp Asn Thr
        35                  40                  45

Pro Phe Leu Ala Ile Leu Gly Ser Arg Pro Val Asn Glu Leu Asn Met
    50                  55                  60

Asp Ala Phe Gln Glu Leu Asn Gln Asn Pro Met Tyr Asn Gly Ile Ala
65                  70                  75                  80

Val Tyr Asn Lys Arg Val Ala Tyr Ala Glu Gln Leu Pro Lys Val Ile
                85                  90                  95

Asp Glu Ala Cys Arg Ala Ala Ile Ser Lys Lys Gly Pro Ala Val Val
            100                 105                 110
```

-continued

```
Glu Ile Pro Val Asn Phe Gly Phe Gln Glu Ile Asp Glu Asn Ser Tyr
        115                 120                 125

Tyr Gly Ser Gly Ser Tyr Glu Arg Ser Phe Ile Ala Pro Ala Leu Asn
        130                 135                 140

Glu Val Glu Ile Asp Lys Ala Val Glu Ile Leu Asn Asn Ala Glu Arg
145                 150                 155                 160

Pro Val Ile Tyr Ala Gly Phe Gly Gly Val Lys Ala Gly Glu Val Ile
                165                 170                 175

Thr Glu Leu Ser Arg Lys Ile Lys Ala Pro Ile Ile Thr Thr Gly Lys
                180                 185                 190

Asn Phe Glu Ala Phe Glu Trp Asn Tyr Glu Gly Leu Thr Gly Ser Ala
            195                 200                 205

Tyr Arg Val Gly Trp Lys Pro Ala Asn Glu Val Val Phe Glu Ala Asp
        210                 215                 220

Thr Val Leu Phe Leu Gly Ser Asn Phe Ala Phe Ala Glu Val Tyr Glu
225                 230                 235                 240

Ala Phe Lys Asn Thr Glu Lys Phe Ile Gln Val Asp Ile Asp Pro Tyr
                245                 250                 255

Lys Leu Gly Lys Arg His Ala Leu Asp Ala Ser Ile Leu Gly Asp Ala
                260                 265                 270

Gly Gln Ala Ala Lys Ala Ile Leu Asp Lys Val Asn Pro Val Glu Ser
        275                 280                 285

Thr Pro Trp Trp Arg Ala Asn Val Lys Asn Asn Gln Asn Trp Arg Asp
        290                 295                 300

Tyr Met Asn Lys Leu Glu Gly Lys Thr Glu Gly Glu Leu Gln Leu Tyr
305                 310                 315                 320

Gln Val Tyr Asn Ala Ile Asn Lys His Ala Asp
                325                 330
```

BACTERIAL EXPORTED PROTEINS AND ACELLULAR VACCINES BASED THEREON

CONTINUING INFORMATION

The present invention is a continuation-in-part of copending application Ser. No. 08/116,541, filed Sep. 1, 1993, now abandoned which is incorporated by reference herein in its entirety, and applicants claim the benefit of the filing date of that application pursuant to 35 U.S.C. § 120.

The research leading to the present invention was supported in part by the United States Government, Grant No. R01-AI27913. The Government may have certain rights in the invention.

FIELD OF THE INVENTION

The present invention relates to the identification of bacterial exported proteins, and the genes encoding such proteins. The invention also relates to acellular vaccines to provide protection from bacterial infection using such proteins, and to antibodies against such proteins for use in diagnosis and passive immune therapy.

BACKGROUND OF THE INVENTION

Exported proteins in bacteria participate in many diverse and essential cell functions such as motility, signal transduction, macromolecular transport and assembly, and the acquisition of essential nutrients. For pathogenic bacteria, many exported proteins are virulence determinants that function as adhesins to colonize and thus infect the host or as toxins to protect the bacteria against the host's immune system (for a review, see Hoepelman and Tuomanen, 1992, Infect. Immun. 60:1729–33).

Since the development of the smallpox vaccine by Jenner in the 18th century, vaccination has been an important armament in the arsenal against infectious microorganisms. Prior to the introduction of antibiotics, vaccination was the major hope for protecting populations against viral or bacterial infection. With the advent of antibiotics in the early 20th century, vaccination against bacterial infections became much less important. However, the recent insurgence of antibiotic-resistant strains of infectious bacteria has resulted in the reestablishment of the importance of antibacterial vaccines.

One possibility for an anti-bacterial vaccine is the use of killed or attenuated bacteria. However, there are several disadvantages of whole bacterial vaccines, including the possibility of a reversion of killed or attenuated bacteria to virulence due to incomplete killing or attenuation and the inclusion of toxic components as contaminants.

Another vaccine alternative is to immunize with the bacterial carbohydrate capsule. Presently, vaccines against *Streptococcus pneumoniae* employ conjugates composed of the capsules of the 23 most common serotypes of this bacterium. these vaccines are ineffective in individuals most susceptible to pathological infection—the young, the old, and the immune compromised—because of its inability to elicit a T cell immune response. A recent study has shown that this vaccine is only 50% protective for these individuals (Shapiro et al., 1991, N. Engl. J. Med. 325:1453–60).

An alternative to whole bacterial vaccines are acellular vaccines or subunit vaccines in which the antigen includes a bacterial surface protein. These vaccines could potentially overcome the deficiencies of whole bacterial or capsule-based vaccines. Moreover, given the importance of exported proteins to bacterial virulence, these proteins are an important target for therapeutic intervention. Of particular importance are proteins that represent a common antigen of all strains of a particular species of bacteria for use in a vaccine that would protect against all strains of the bacteria. However, to date only a small number of exported proteins of Gram positive bacteria have been identified, and none of these represent a common antigen for a particular species of bacteria.

A strategy for the genetic analysis of exported proteins in *E. coli* was suggested following the description of translational fusions to a truncated gene for alkaline phosphatase (phoA) that lacked a functional signal sequence (Hoffman and Wright, 1985, Proc. Natl. Acad. Sci. U.S.A. 82:5107–5111). In this study, enzyme activity was readily detected in strains that had gene fusions between the coding regions of heterologous signal sequences and phoA indicating that translocation across the cytoplasmic membrane was required for enzyme activity. Subsequently, a modified transposon, TnphoA, was constructed to facilitate the rapid screening for translational gene fusions (Manoil and Beckwith, 1985, Proc. Natl. Acad. Sci. U.S.A. 82:8129–8133). This powerful tool has been modified and used in many Gram negative pathogens such as *Escherichia coli* (Guitierrez et al., 1987, J. Mol. Biol. 195:289–297), *Vibrio cholera* (Taylor et al., 1989, J. Bacteriol. 171:1870–1878), *Bordetella pertussis* (Finn et al., 1991, Infect Immun. 59:3273–9; Knapp and Mekalanos, 1988, J. Bacteriol. 170:5059–5066) and *Legionella pneumophila* (Albano et al., 1992, Mol. Microbiol. 6:1829–39), to yield a wealth of information from the identification and characterization of exported proteins. A similar strategy based on gene fusions to a truncated form of the gene for β-lactamase has been used to the same end (Broome-Smith et al., 1990, Mol. Microbiol. 4:1637–1644). A direct strategy for mapping the topology of exported proteins has also been developed based on "sandwich" gene fusions to phoA (Ehrmann et al., 1990, 87:7574–7578).

For a variety of reasons, the use of gene fusions as a genetic screen for exported proteins in Gram positive organisms has met with limited success. Plasmid vectors that will create two or three part translational fusions to genes for alkaline phosphatase, β-lactamase and a-amylase have been designed for *Bacillus subtilis* and *Lactococcus lacti* (Payne and Jackson, 1991, J. Bacteriol. 173:2278–82; Perez et al., 1992, Mol. Gen. Genet. 234:401–11; Smith et al., 1987, J. Bacteriol. 169:3321–3328; Smith et al., 1988, Gene 70:351–361). Gene fusions between phoA and the gene for protein A (spa) from *Staphylococcus aureus* have been used to determine the cellular localization of this protein (Schneewind et al., 1992, Cell. 70:267–81). In that study, however, enzyme activity for alkaline phosphatase was not reported.

Mutagenesis strategies in several streptococcal species have also been limited for several reasons. Efficient transposons similar to those that are the major tools to study Gram negative bacteria have not been developed for streptococcus. Insertion duplication mutagenesis with non-replicating plasmid vectors has been a successful alternative for *Streptococcus pneumoniae* (Chen and Morrison, 1988, Gene. 64:155–164; Morrison et al., 1984, J. Bacteriol. 159:870). This strategy has led to the mutagenesis, isolation and cloning of several pneumococcal genes (Alloing et al., 1989, Gene. 76:363–8; Berry et al., 1992, Microb. Pathog. 12:87–93; Hui and Morrison, 1991, J. Bacteriol. 173:372–81; Lacks and Greenberg, 1991, Gene. 104:11–7; Laible et al., 1989, Mol. Microbiol. 3:1337–48; Martin et al., 1992, J. Bacteriol. 174:4517–23; McDaniel et al., 1987, J.

Exp. Med. 165:381–94; Prudhomme et al., 1989, J. Bacteriol. 171:5332–8; Prudhomme et al., 1991, J. Bacteriol. 173:7196–203; Puyet et al., 1989, J. Bacteriol. 171:2278–2286; Puyet et al., 1990, J. Mol. Biol. 213:727–38; Radnis et al., 1990, J. Bacteriol. 172:3669–74; Sicard et al., 1992, J. Bacteriol. 174:2412–5; Stassi et al., 1981, Proc. Natl. Acad. Sci. U.S.A. 78:7028–7032; Tomasz et al., 1988, J. Bacteriol. 170:5931–5934; Yother et al., 1992, J. Bacteriol. 174:610–8).

Of note in the search for exported pneumococcal proteins that might be attractive targets for a vaccine is pneumococcal surface protein A (PspA) (see Yother et al., 1992, supra). PspA has been reported to be a candidate for a *S. pneumoniae* vaccine as it has been found in all pneumococci to date; the purified protein can be used to elicit protective immunity in mice; and antibodies against the protein confer passive immunity in mice (Talkington et al., 1992, Microb. Pathog. 13:343–355). However, PspA demonstrates antigenic variability between strains in the N-terminal half of the protein, which contains the immunogenic and protection eliciting epitopes (Yother et al., 1992, supra). This protein does not represent a common antigen for all strains of *S. pneumoniae*, and therefore is not an optimal vaccine candidate.

Recently, apparent fusion proteins containing PhoA were exported in species of Gram positive and Gram negative bacteria (Pearce and Masure, 1992, Abstr. Gen. Meet. Am. Soc. Microbiol. 92:127, abstract D-188). This abstract reports insertion of pneumococcal DNA upstream from the *E. coli* phoA gene lacking its signal sequence and promoter in a shuttle vector capable of expression in both *E. coli* and *S. pneumoniae*, and suggests that similar pathways for the translocation of exported proteins across the plasma membranes must be found for both species of bacteria.

Recent studies have shown that genetic transfer in several bacterial species relies on a signal response mechanism between individual cells. Conjugal plasmid transfer is mediated by homoserine lactones in *Agrobacterium tumifaciens* (Zhang et al., 1993, Scinece 362:446–448) and by small secreted polypeptides in *Enterococcus faecalis* (for a review, see Clewell, 1993, Cell 73:9–12). Low molecular weight peptide activators have been described which induce transformation in *S. pneumoniae* (Tomasz, 1965, Nature 208:155–159; Tomasz, 1966, J. Bacteriol. 91:1050–61; Tomasz and Mosser, 1966, Proc. Natl. Acad. Sci. USA 55:58–66) and *Streptococcus sanguis* (Leonard and Cole, 1972, J. Bacteriol. 110:273–280; Pakula et al., 1962, Acta Microbiol. Pol. 11:205–222; Pakula and Walczak, 1963, J. Gen. Microbiol. 31:125–133). A peptide activator which regulates both sporulation and transformation has been described for *B. subtilis* (Grossman and Losick, 1988, Proc. Natl. Acad. Sci. USA 85:4369–73). Furthermore, genetic evidence suggests that peptide permeases may be mediating these processes in both *E. faecalis* (Ruhfel et al., 1993, J. Bacteriol. 175:5253–59; Tanimoto et al., 1993, J. Bacteriol. 175:5260–64) and *B. subtilis* (Rudner et al., 1991, J. Bacteriol. 173:1388–98).

In *S. pneumoniae*, transformation occurs as a programmed event during a physiologically defined "competent" state. Induced by an unknown signal in a density dependent manner, cells exhibit a single wave of competence between $5 \times 10^6$ and $1-2 \times 10^7$ cfu/ml which is the beginning of logarithmic growth (Tomasz, 1966, supra). With induction, a unique set of competence associated proteins are expressed (Morrison and Baker, 1979, Nature 282:215–217) suggesting global regulation of transformation associated genes. Competent bacteria bind and transport exogenous DNA, which if homologous is incorporated by recombination into the genome of the recipient cell. Within one to two cell divisions, the bacteria are no longer competent. As with induction, inactivation of competence occurs by an unknown mechanism.

The citation of references herein shall not be construed as an admission that such is prior art to the present invention.

SUMMARY OF THE INVENTION

The present invention concerns genes encoding exported proteins in a Gram positive bacteria, and the proteins encoded by such genes. In particular, the invention provides for isolation of genes encoding Gram positive bacterial adhesion associated proteins, preferably adhesins, virulence determinants, toxins, or immunodominant proteins, and thus provides the genes and proteins encoded thereby. In another aspect, the exported protein can be an antigen common to many or all strains of a species of Gram positive bacteria, and that may be antigenically related to a homologous protein from a closely related species of bacteria. The invention also contemplates identification of proteins that are antigenically unique to a particular strain of bacteria. Preferably, the exported protein is an adhesin common to all strains of a species of Gram positive bacteria.

The invention further relates to a vaccine for protection of an animal subject from infection with a Gram positive bacterium comprising a vector containing a gene encoding an exported adhesion associated protein, or a gene encoding an exported protein which is an antigen common to many strains, of a species of a Gram positive bacterium operably associated with a promoter capable of directing of directing expression of the gene in the subject.

In another aspect, the invention is directed to a vaccine for protection of an animal subject from infection with a Gram positive bacterium comprising an immunogenic amount of an exported adhesion associated protein, virulence determinant, toxin, or immunodominant protein of a Gram positive bacterium, or an immunogenic amount of an exported protein which is an antigen common to many strains of a species of Gram positive bacterium, and an adjuvant. Preferably, such a vaccine contains the protein conjugated covalently to a bacterial capsule or capsules from one or more strains of bacteria. More preferably, the capsules from all the common strains of a species of bacteria are included in the vaccine.

Alternatively, the protein can be used to immunize an appropriate animal to generate polyclonal or monoclonal antibodies, as described in detail below. Thus, the invention further relates to antibodies reactive with exported proteins of Gram positive bacteria. Such antibodies can be used in immunoassays to diagnose infection with a particular strain or species of bacteria. Thus, strain-specific exported proteins can be used to generate strain-specific antibodies for diagnosis of infection with that strain. Alternatively, common antigens can be used to prepare antibodies for the diagnosis of infection with that species of bacterium. In a specific aspect, the species of bacterium is *S. pneumoniae*. The antibodies can also be used for passive immunization to treat an infection with Gram positive bacteria.

Thus, it is an object of the present invention to provide genes encoding exported proteins of Gram positive bacteria. Preferably, such genes encode adhesion associated proteins, virulence determinants, toxins, or immunodominant proteins that are immunogenic. Preferably, the protein is an antigen common to many strains of a species of Gram positive bacterium, as the products of such genes are particularly attractive vaccine candidates.

It is a further object of the invention to provide an acellular vaccine against a Gram positive bacterium, thus overcoming the deficiencies of whole killed or attenuated bacterial vaccines and capsular vaccines.

Another object of the present invention is to provide a capsular vaccine that elicits a helper T cell immune response.

It is yet a further object of the invention to provide for the diagnosis of infection with a Gram positive bacterium.

Another object of the invention is to provide for passive immune therapy for a Gram positive bacterial infection, particularly for an infection by an antibiotic resistant bacterium.

BRIEF DESCRIPTION OF THE DRAWINGS

FIG. 4. Derived amino acid sequences for the genetic loci recovered from PhoA$^+$ pneumococcal mutants. Each of the plasmids recovered from the nine PhoA$^+$ strains of S. pneumoniae (see Table 1) were transformed into E. coli and had 400 to 700 base pair inserts. Using a primer to the 5' end of phoA, approximately 200 to 500 base pairs of pneumococcal DNA immediately upstream of phoA was sequenced from each plasmid and an in-frame coding region with PhoA was established. The derived amino acid sequences from the fusions are presented for Exp1 [SEQ ID NO:2], Exp2 [SEQ ID NO:24], Exp3 [SEQ ID NO:6], Exp4 [SEQ ID NO:8], Exp5 [SEQ ID NO:10], Exp6 [SEQ ID NO:12], Exp7 [SEQ ID NO:14], Exp8 [SEQ ID NO:16], and Exp9a [SEQ ID NO:18]. The derived sequence from the 5' end of the insert from Exp9 is also presented in Exp9b [SEQ ID NO:20].

FIG. 5. Sequence alignments of the derived amino acid sequences from the Exp loci recovered from PhoA$^+$ mutants. The highest scoring match for each insert is presented. The percent identity (% ID) and percent similarity (% SIM) for each alignment is presented on the right. (A) Exp1 [SEQ ID NO:2] and AmiA from S. pneumoniae [SEQ ID NO:23] (Alloing et al., 1990, Mol. Microbiol. 4:633–44). B) Exp2 [SEQ ID NO:24] and PonA from S. pneumoniae [SEQ ID NO:24] (Martin et al., 1992, J. Bacteriol. 174:4517–23). C) Exp3 [SEQ ID NO:25] and PilB from N. gonorrhoeae [SEQ ID NO:26] (Taha et al., 1988, EMBO J. 7:4367–4378). The conserved histidine ($H_{408}$) in PilB is not present in Exp3 but is replaced by asparagine ($N_{124}$). D) Exp4 [SEQ ID NO:27] and CD4B from tomato [SEQ ID NO:28] (Gottesman et al., 1990, Proc. Natl. Acad. Sci. U.S.A. 87:3513–7). E) Exp5 [SEQ ID NO:29] and PtsG from B. subtilis [SEQ ID NO:30] (Gonzy-Tréboul et al., 1991, Mol. Microbiol. 5:1241–1294). F) Exp6 [SEQ ID NO:31] and GlpD from B. subtilis [SEQ ID NO:32] (Holmberg et al., 1990, J. Gen. Microbiol. 136–2367–2375). G) Exp7 [SEQ ID NO:33] and MgtB from S. typhimurium [SEQ ID NO:34] (Snavely et al., 1991, J. Biol. Chem. 266:815–823). The conserved aspartic acid ($D_{554}$) required for autophosphorylation is also present in Exp7 ($D_{37}$). H) Exp8 [SEQ ID NO:35] and CyaB from B. pertussis [SEQ ID NO:36] (Glaser et al., 1988, Mol. Microbiol. 2:1930; Glaser et al., 1988, EMBO J. 7:3997–4004). I) Exp9 and DeaD from E. coli (Toone et al., 1991, J. Bacteriol. 173:3291–3302). The top sequence from Exp9 [SEQ ID NO:37] is derived from the 5' end of the recovered plasmid insert, and compared to DeaD 135–220 [SEQ ID NO:38]. The bottom sequence from Exp9 [SEQ ID NO:20] is derived from the 3' end of the recovered plasmid insert just upstream from phoA, and is compared with DeaD 265–342 [SEQ ID NO:39]. The conserved DEAD sequence is highlighted.

FIG. 10. Nucleotide and deduced amino acid sequences for the genetic locus recovered from the SPRU25 mutant, exp10. The nucleotide sequence was obtained as described in FIG. 4 and in Example 1, infra.

FIG. 11. Nucleotide (SEQ ID NO: 46) and derived protein (SEQ ID NO: 47) sequences of plpA. The lipoprotein modification consensus sequence is underlined with an asterisk above the cysteine residue where cleavage would occur. Downstream from the coding region a potential rho independent transcription terminator is underlined. The positions of the PhoA fusions at Leu$_{197}$ in SPRU58 and Asp$_{492}$ in SPRU98 are indicated. (Genbank accession number: TO BE ASSIGNED).

FIG. 13. Subcellular localization and labeling of PlpA-PhoA. Upper panel: Subcellular fractions (50 μg of total protein) from SPRU98 (PhoA$^+$, pHRM104::plpA) were applied to an 8–25% SDS polyacrylamide gel, transferred to a nitrocellulose membrane and probed with anti-PhoA antisera. Bound antibodies were detected with a peroxidase conjugated second antibody and visualized with enhanced chemiluminescence. Lanes are A, culture supernatant; B, membranes; C, cytoplasm; and D, cell wall. Lower panel: Anti-PhoA immunoprecipitates of total cell lysates from bacteria grown in a chemically defined media with [$^3$H] palmitic acid were applied to an 8–25% SDS polyacrylamide gel, transferred to a nitrocellulose membrane and subjected to autoradiography. Lanes are E, parental strain R6x; F, SPRU100(PhoA$^+$, pHRM104::zzz); and G, SPRU98 (PhoA$^+$, pHRM104::plpA). The arrow marks the 93 kDa band that corresponds to the immunoprecipitated PlpA-PhoA fusion protein.

FIG. 15. Transformation efficiency of pneumococcal permease mutants. Various strains containing the depicted chromosomal gene constructs with lesions in either plpA or ami were assayed for the incorporation of a chromosomal streptomycin resistance marker as a measure of transformation efficiency. Transformation efficiency of each strain is presented as a percent of the parental strain, R6x, which routinely produces 0.3% Str$^r$ transformants in the total population of transformable cells. Values presented are the average of at least three data points with the standard error of the mean. The results are representative of assays performed on three separate occasions. E is erythromycin resistance encoded by the vector.

FIG. 23. Nucleotide and deduced amino acid sequences of Pad1. (A) Nucleotide sequence of the upstream region (SEQ ID NO: 55). The putative-35, -10 taata and riboxome binding sites are underlined. (B) Deduced amino acid sequence of the upstream region (SEQ ID NO: 56). There appears to be some "compression" in the DNA sequence, since by sequence homology, it appears that four amino acids are missing from this sequence. (C) Nucleotide sequence of the coding region of pad1 (SEQ ID NO: 57). (D) Deduced amino acid sequence of the coding region of Pad1 (SEQ ID NO: 58). Based on sequence homology, there are about 200 amino acids missing from the full length sequence.

DETAILED DESCRIPTION OF THE INVENTION

Figure 1B:
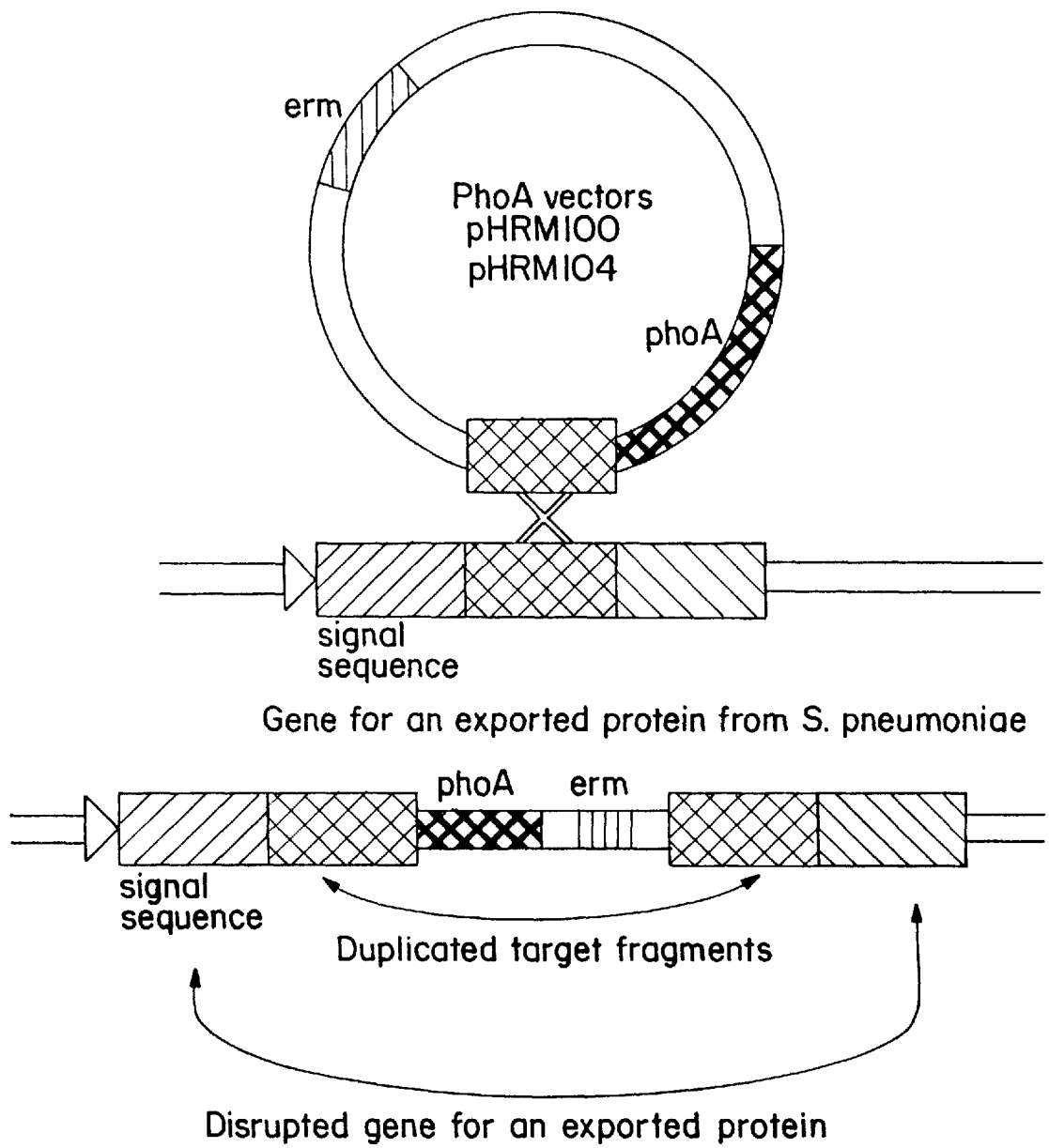
FIG. 1. Construction of PhoA fusion vectors designed for the mutation and genetic identification of exported proteins in S. pneumoniae. (A) The 2.6 kB fragment of pPHO7 containing a truncated form of phoA was inserted into either the SmaI or BamHI sites of pJDC9 to generate pHRM100 and pHRM104 respectively. T1T2 are transcription terminators and the arrows indicate gene orientation. (B) Mechanism of insertion duplication mutagenesis coupled to gene fusion. PhoA activity depends on the cloning of an internal gene fragment that is in-frame and downstream from a gene that encodes an exported protein. Transformation into S. pneumoniae results in duplication of the target fragment and subsequent gene disruption.

In accordance with the present invention there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual," Second Edition (1989) Cold Spring Harbor Laboratory Press, Cold Spring Harbor, New York (herein "Sambrook et al., 1989"); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A "replicon" is any genetic element (e.g., plasmid, chromosome, virus) that functions as an autonomous unit of DNA replication in vivo, i.e., capable of replication under its own control.

A "vector" is a replicon, such as plasmid, phage or cosmid, to which another DNA segment may be attached so as to bring about the replication of the attached segment.

The term "viral vector" refers to a virus containing a recombinant nucleic acid, whereby the virus can introduce the recombinant nucleic acid to a cell, i.e., the virus can transform the cell. According to the present invention, such vectors may have use for the delivery of a nucleic acid-based vaccine, as described herein.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. A "clone" is a population of cells derived from a single cell or common ancestor by mitosis.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989, supra). The conditions of temperature and ionic strength determine the "stringency" of the hybridization. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. Preferably a minimum length for a hybridizable nucleic acid is at least about 10 nucleotides; more preferably at least about 15 nucleotides.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of deferring the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. Eukaryotic promoters will often, but not always, contain "TATA" boxes and "CAT" boxes.

A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that directs the host cell to translocate the polypeptide to the cell surface or secrete the polypeptide into the media, and this signal peptide is selectively degraded by the cell upon exportation. Signal sequences can be found associated with a variety of proteins native to prokaryotes and eukaryotes.

As used herein, the term "exported protein" refers to a protein that contains a signal sequence, and thus is found associated with or outside of the cell membrane. Thus, secreted proteins, integral membrane proteins, surface proteins, and the like fall into the class of exported proteins. The term "surface protein" as used herein is specifically intended to refer to a protein that is accessible at the cell surface, e.g., for binding with an antibody.

An "adhesion associated protein" is a protein that is directly or indirectly involved in adherence of bacteria to target cells, such as endothelial cells or lung cells. The term "adhesion associated protein" includes proteins that may have other functional activities, such as motility, signal transduction, cell wall assembly, or macromolecular transport. An "adhesin" is an adhesion-associated protein found on the surface of a cell, such as a bacterium, that is directly involved in adherence, and thus effects some degree of adherence or adhesion to another cell. Of particular importance to the present invention are adhesins of Gram positive bacteria that promote adhesion to eukaryotic cells, i.e., that are involved in bacterial virulence. Adhesins, in order to be effective in promoting adherence, should be surface proteins, i.e., be accessible at the surface of the cell. Accessibility is also important to determine antigenicity. A vaccine that elicits antibodies against an adhesin can provide antibodies that bind to an accessible antigenic determinant and directly interfere with adherence, thus preventing infection. An adhesin of the invention need not be the only adhesin or adhesion mediator of a Gram positive bacteria, and the term contemplates any protein that demonstrates some degree of adhesion activity, whether relatively strong or relatively weak.

A "virulence determinant" is any bacterial product required for bacterial survival within an infected host. Thus, virulence determinants are also attractive vaccine candidates since neutralization of a virulence determinant can reduce the virulence of the bacteria.

A "toxin" is any bacterial product that actively damages an infected host. Thus, bacterial toxins are important targets for an immune response in order to neutralize their toxicity.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.*, 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

In its primary aspect, the present invention concerns the identification and isolation of a gene encoding an exported protein in a Gram positive bacteria. The exported protein can be a protein of unknown or of known function. Herein, all such exported proteins, whether of known or of unknown function, are referred to as "Exp" (for exported protein), and the genes encoding such proteins are referred to as "exp" genes. In particular, the invention provides for isolation of genes encoding Gram positive bacterial adhesion associated proteins, preferably adhesins, virulence determinants, toxins and immunodominant antigens. Preferably, the exported protein can be an antigen common to all strains of a species of Gram positive bacteria, or that may be antigenically related to a homologous protein from a closely related species of bacteria. The invention also contemplates identification of proteins that are antigenically unique to a particular strain of bacteria. Preferably, the exported protein is an adhesin common to all strains of a species of Gram positive bacteria, in particular, *S. pneumoniae*.

In particular, the invention concerns various exported proteins of *S. pneumoniae* (see Table 1, infra), some of which demonstrate activity as adhesins. In specific embodiments, the invention provides gene fragments of the following exported proteins: Exp1 [SEQ ID NO:2], the full length sequence of which, termed Plp1 [SEQ ID NO:47], is also provided, encoded by exp1 [SEQ ID NO:1] and plp1 [SEQ ID NO:46], respectively, a protein that appears to be related to the permease family of proteins and which is therefore surprisingly associated with adhesion; Exp2 [SEQ ID NO:3], encoded by exp2 [SEQ ID NO:4], which nucleic acid sequence is identical to ponA, which encodes penicillin-binding protein 1A (Martin et al., 1992, J. Bacteriol. 174:4517–4523), and which is unexpectedly associated with adhesion; Exp3 [SEQ ID NO:6], encoded by exp3 [SEQ ID NO:5], which is associated with adhesion; Exp4 (SEQ ID NO:8], encoded by exp4 [SEQ ID NO:7], which is associated with adhesion; Exp5 [SEQ ID NO:10], encoded by exp5 [SEQ ID NO:9]; Exp6 [SEQ ID NO:12], encoded by exp6 [SEQ ID NO:11]; Exp7 [SEQ ID NO:14], encoded by exp7 [SEQ ID NO:13]; Exp 8 [SEQ ID NO:16], encoded by exp8 [SEQ ID NO:15]; Exp9 [SEQ ID NOS. 18 and 20], encoded by exp9 [SEQ ID NOS. 17 and 19, respectively]; Exp10 [SEQ ID NO:22], encoded by exp10 [SEQ ID NO:21]; and Pad1 [SEQ ID NO:58], encoded by pad1 [SEQ ID NO:57], which is a pyruvate oxidase homolog. The strain designations of mutant bacteria in which the Exp1–9 proteins were identified are disclosed in Table 1. The strain designation of the mutant in which Exp10 was identified is SPRU25. Applicants have also isolated a mutant *S. pneumoniae* (SPRU121) in which the amiA gene encoding the AmiA protein has been mutated, and have demonstrated for the first time that this is an adhesion associated protein, and thus, that this protein can be used in a vaccine to elicit an anti-adhesion-associated protein immune response.

Once the genes encoding exported proteins are isolated, they can be used directly as an in vivo nucleic acid-based vaccine. Alternatively, the nucleotide sequence of the genes can be used to prepare oligonucleotide probes or primers for polymerase chain reaction (PCR) for diagnosis of infection with a particular strain or species of Gram positive bacterium.

Alteratively, the proteins encoded by the isolated genes can be expressed and used to prepare vaccines for protection against the strain of bacteria from which the exported protein was obtained. If the exported protein is an adhesion associated protein, such as an adhesin, it is a particularly attractive vaccine candidate since immunity can interfere with the bacterium's ability to adhere to host cells, and thus infect, i.e., colonize and survive, within host organism. If the exported protein is a virulence determinant, immunity can interfere with virulence. If the exported protein is a toxin, immunity can interfere with toxicity. More preferably, the exported protein is an antigen common to all or almost all strains of a particular species of bacterium, and thus is an ideal candidate for a vaccine against all or almost all strains of that species. In a specific embodiment, the species of bacterium is *S. pneumoniae*.

Alternatively, the protein can be used to immunize an appropriate animal to generate polyclonal or monoclonal antibodies, as described in detail below. Such antibodies can be used in immunoassays to diagnose infection with a particular strain or species of bacteria. Thus, strain-specific exported proteins can be used to generate strain-specific antibodies for diagnosis of infection with that strain. Alternatively, common antigens can be used to prepare antibodies for the diagnosis of infection with that species of bacterium. In a specific aspect, the species of bacterium is *S. pneumoniae*.

In yet another embodiment, if the Exp is an adhesin, the soluble protein can be administered to a subject suspected of suffering an infection to inhibit adherence of the bacterium.

Isolation of Genes for Exported Proteins

The present invention provides a number of gene fragments that can be used to obtain the full length gene encoding exported Gram positive bacterial antigens, in particular exported adhesins.

The invention further provides a method, using a vector that encodes an indicator protein that is functional only when exported from a bacterium, such as the phoA vector described herein, to screen for genes encoding exported pneumococcal proteins. For example, a truncated form of phoA can be placed in a pneumococcal shuttle vector, such as vector pJDC9 (Chen and Morrison, 1988, Gene 64:155–164). A cloning site containing a unique restriction site, e.g., SmaI or BamHI can be located immediately 5' to phoA, to allow insertion of DNA that may encode an export protein. Preferably, the cloning sites in the vector are flanked by two restriction sites to facilitate easy identification of an insert. In a specific embodiment, the restriction site is a KpnI site, although any restriction endonuclease can be used. Gene fragments encoding Exp's are selected on the basis of blue staining around the bacterium, which is indicative of export of the PhoA enzyme. The exp-phoA fusion genes can be expressed in *E. coli*, although a promoter fusion may be required in this instance. When integrated into the genome of a Gram positive organism, the exp-phoA fusion gene is a translational fusion involving duplication mutagenesis, and expressed in a Gram positive bacterium. In a specific embodiment, pneumococcal export proteins are identified with this technique, which requires cloning of an internal gene fragment within the vector prior to integration.

In a further embodiment, screening for genes encoding exported adhesion associated proteins can be performed on PhoA-positive transformants by testing for loss of adherence of a Gram positive bacterium to a primary cell or a cell line to which it normally adheres. Such adhesion assays can be performed on any eukaryotic cell line. Preferably, if infection of humans is important, the cell or cell line is derived from a human source or has been demonstrated to behave like human cells in a particular in vitro assay. Suitable cells and cell lines include, but are not limited to, endothelial cells, lung cells, leukocytes, buccal cells, adenoid cells, skin cells, conjunctivial cells, ciliated cells, and other cells representative of infected organs. As demonstrated in an example, infra, a human umbilical vein endothelial cell (HUVEC) line, which is available from Clonetics (San Diego, Calif.), can be used. In another example, infra, lung Type II alveolar cells, which can be prepared as described in Example 2 or can be obtained as a cell line available from the American Type Culture Collection (ATCC) under accession number ATCC A549, are used. Alternatively, adherence to human monocyte-derived macrophages, obtained from blood, can be tested. Other target cells, especially for *S. pneumoniae*, are oropharyngeal cells, such as buccal epithelial cells (Andersson et al. (1988, Microb. Pathogen. 4:267–278; 1983, J. Exp. Med. 158:559–570; 1981, Infect. Inunun. 32:311–317).

Generally, any adherence assay known in the art can be used to demonstrate loss of adhesion due to mutagenesis of the Exp. One such assay follows: The cells to which adherence is to be assayed are cultured for 4–8 days (Wright AND Silverstein, 1982, J. Exp. Med. 156:1149–1164) and then transferred to Terasaki dishes 24 hours prior to the adherence assay to allow formation of a confluent monolayer (Geelen et al., 1993, Infect. Immun. 61:1538–1543). The bacteria are labelled with fluorescein (Geelen et al., supra), adjusted to a concentration of $5 \times 10^7$ cfu/ml, and added in a volume of 5 µl to at least 6 wells. After incubation at 37° C. for 30 min, the plates are washed and fixed with PBS/glutaraldehyde 2.5%. Attached bacteria are enumerated visually using a fluorescence microscope, such as a Nikon Diaphot Inverted Microscope equipped with epifluorescence.

Since two mechanisms, the cell wall and adhesin proteins, determine adherence of a Gram positive bacterium, in particular *S. pneumoniae*, to a target cell, it may be important to distinguish whether the mutation to the exported protein that inhibits adherence is a mutation to a protein involved in cell wall synthesis or an adhesin. Mutation of the former would have an indirect affect on adherence, while mutation of the latter would directly affect adherence. The following assays can be used to distinguish whether the mutated protein is an adhesin or not: (1) since adherence to macrophages is mainly mediated by exported proteins, adherence assays on macrophages will immediately indicate whether the mutation is to an adhesin; (2) there will be a minimal effect on adherence if bacterial cell wall is separately added in the adherence assay if the mutation is to a protein indirectly involved in adherence, and a further inhibition of adherence if added to a mutant mutated at an adhesin; (3) pretreatment of the bacteria with a protease, such as trypsin, will result in further inhibition of adherence if the mutation is to a protein indirectly involved in adherence, but will have no effect if the mutated protein is an adhesin; (4) once the full length exp gene is isolated, the putative adhesin can be expressed in E. coli or another cell type, or the purified putative adhesin can be covalently associated with different support such as a bacteria, an erytlirocyte or an agarose bead, and the ability of the putative adhesin to mediated adherence can be evaluated; (5) the cell wall structure of mutants can be evaluated using standard techniques, in particular HPLC fingerprinting, to determine if the mutation resulted in changes to the cell wall structure, which is indicative of a mutation to a protein indirectly involved with adherence.

In another embodiment, the invention provides for identifying genes encoding exported virulence determinants. Generally, virulence determinants can be identified by testing the mutant strain in an animal model for virulence, for example by evaluation of the $LD_{50}$ of the animal infected with the strain. An increase in the $LD_{50}$ is indicative of a loss of virulence, and therefore the mutation occurred in a locus required for virulence.

The invention also provides for identification of an Exp that is an antigen common to all or many strains of a species of bacterium, or to closely related species of bacteria. This is readily accomplished using an antibody specific to an Exp (the preparation of which is described in detail infra). The ability of the antibody to that particular strain and to all or many other strains of that species, or to closely related species, demonstrates that the Exp is a common antigen. This antibody assay is particularly preferred since it is more immunologically relevant, since the Exp that is a common antigen is an attractive vaccine candidate.

Generally, the invention also provides for identification of a functional property of a protein produced by an exp gene by comparing the homology of the deduced amino acid or nucleotide sequence to the amino acid sequence of a known protein, or the nucleotide sequence of the gene encoding the protein.

Any Gram positive bacterial cell can potentially serve as the nucleic acid source for the molecular cloning of an exp gene. The nucleic acid sequences can be isolated from Streptococcus, Bacillus, Mycobacterium, Staphylococcus, Enterococcus, and other Gram positive bacterial sources, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired exp gene may be accomplished in a number of ways. For example, if an amount of a portion of an exp gene or a fragment thereof is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). Those DNA fragments with substantial homology to the probe will hybridize. The present invention provides specific examples of DNA fragments that can be used as hybridization probes for pneumococcal exported proteins. These DNA probes can be based, for example, on SEQ ID NOS. 1, 3, 5, 7, 9, 11, 13, 15, 17, 19 or 21. Alternatively, the screening technique of the invention can be used to isolate additional exp gene fragments for use as probes.

It is also possible to identify the appropriate fragment by restriction enzyme digestion(s) and comparison of fragment sizes with those expected according to a known restriction map if such is available. Further selection can be carried out on the basis of the properties of the gene.

As described above, the presence of the gene may be detected by assays based on the physical, chemical, or immunological properties of its expressed product. For example DNA clones that produce a protein that, e.g., has similar or identical electrophoretic migration, isoelectric focusing behavior, proteolytic digestion maps, proteolytic activity, antigenic properties, or functional properties, especially adhesion activity, as known (or in the case of an adhesion associated protein, unknown) for a particular Exp. In a specific example, infra, the ability of a pneumococcal Exp protein to mediate adhesion is demonstrated by inhibition of adhesion when the protein is mutated. Expression of Exp in another species, such as E. coli, can directly demonstrate whether the exp encodes an adhesin.

Alternatives to isolating the exp genomic DNA include, but are not limited to, chemically synthesizing the gene sequence itself from a known sequence that encodes an Exp. For example, DNA cloning of an exp gene can be isolated from Gram positive bacteria by PCR using degenerate oligonucleotides. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. In a preferred aspect of the invention, the exp coding sequence is inserted in an E. coli cloning vector. Other examples of vectors include, but are not limited to, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionation, can be done before insertion into the cloning vector.

In specific embodiments, transformation of host cells with recombinant DNA molecules that incorporate the isolated exp gene or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The present invention also relates to vectors containing genes encoding analogs and derivatives of Exp's that have the same functional activity as an Exp. The production and use of derivatives and analogs related to an Exp are within the scope of the present invention. In a specific embodiment, the derivative or analog is functionally active, i.e., capable of exhibiting one or more functional activities associated with a full-length, wild-type Exp. As one example, such derivatives or analogs demonstrate adhesin activity.

In particular, Exp derivatives can be made by altering encoding nucleic acid sequences by substitutions, additions or deletions that provide for functionally equivalent molecules. Due to the degeneracy of nucleotide coding sequences, other DNA sequences which encode substantially the same amino acid sequence as an exp gene may be used in the practice of the present invention. These include but are not limited to nucleotide sequences comprising all or portions of exp genes that are altered by the substitution of different codons that encode the same amino acid residue within the sequence, thus producing a silent change. Likewise, the Exp derivatives of the invention include, but are not limited to, those containing, as a primary amino acid sequence, all or part of the amino acid sequence of an Exp including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The genes encoding Exp derivatives and analogs of the invention can be produced by various methods known in the art. The manipulations which result in their production can occur at the gene or protein level. For example, a cloned exp gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of Exp, care should be taken to ensure that the modified gene remains within the same translational reading frame as the exp gene, uninterrupted by translational stop signals, in the gene region where the desired activity is encoded.

Additionally, the exp nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplifation*, H. Erlich, ed., Stockton Press, Chapter 6, pp. 61–70).

Expression of an Exported Protein

The gene coding for an Exp, or a functionally active fragment or other derivative thereof, can be inserted into an appropriate expression vector, i.e., a vector which contains the necessary elements for the transcription and translation of the inserted protein-coding sequence. An expression vector also preferably includes a replication origin. The necessary transcriptional and translational signals can also be supplied by the native exp gene and/or its flanking regions. A variety of host-vector systems may be utilized to express the protein-coding sequence. Preferably, however, a bacterial expression system is used to provide for high level expression of the protein with a higher probability of the native conformation. Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Preferably, the periplasmic form of the Exp (containing a signal sequence) is produced for export of the protein to the *Escherichia coli* periplasm or in an expression system based on *Bacillus subtillis*. Export to the periplasm can promote proper folding of the expressed protein.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination).

Expression of nucleic acid sequence encoding an exported protein or peptide fragment may be regulated by a second nucleic acid sequence so that the exported protein or peptide is expressed in a host transformed with the recombinant DNA molecule. For example, expression of an exported protein may be controlled by any promoter/enhancer element known in the art, but these regulatory elements must be functional in the host selected for expression. For expression in bacteria, bacterial promoters are required. Eukaryotic viral or eukaryotic promoters, including tissue specific promoters, are preferred when a vector containing an exp gene is injected directly into a subject for transient expression, resulting in heterologous protection against bacterial infection, as described in detail below. Promoters which may be used to control exp gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing exp gene inserts can be identified by four general approaches: (a) PCR amplification of the desired plasmid DNA or specific mRNA, (b) nucleic acid hybridization, (c) presence or absence of "marker" gene functions, and (d) expression of inserted sequences. In the first approach, the nucleic acids can be amplified by PCR with incorporation of radionucleotides or stained with ethidium bromide to provide for detection of the amplified product. In the second approach, the presence of a foreign gene inserted in an expression vector can be detected by nucleic acid hybridization using probes comprising sequences that are homologous to an inserted exp gene. In the third approach, the recombinant vector/host system can be identified and selected based upon the presence or absence of certain "marker" gene functions (e.g., β-galactosidase activity, PhoA activity, thymidine kinase activity, resistance to antibiotics, transformation phenotype, occlusion body formation in baculovirus, etc.) caused by the insertion of foreign genes in the vector. If the exp gene is inserted within the marker gene sequence of the vector, recombinants containing the exp insert can be identified by the absence of the marker gene function. In the fourth approach, recombinant expression vectors can be identified by assaying for the activity of the exp gene product expressed by the recombinant. Such assays can be based, for example, on the physical or functional properties of the exp gene product in in vitro assay systems, e.g., adherence to a target cell or binding with an antibody to the exported protein.

Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few. The choice of vector will depend on the desired use of the vector, e.g., for expression of the protein in prokaryotic or eukaryotic cells, or as a nucleic acid-based vaccine.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered exported protein may be controlled. Furthermore, different host cells have characteristic and specific mechanisms for the translational and post-translational processing and modification (e.g., cleavage of signal sequence) of proteins. Appropriate cell lines or host systems can be chosen to ensure the desired modification and processing of the foreign protein expressed. Different vector/host expression systems may effect processing reactions, such as proteolytic cleavages, to a different extent.

Preparation of Antibodies to Exported Proteins

According to the invention, recombinant Exp, and fragments or other derivatives or analogs thereof, or cells expressing the foregoing may be used as an immunogen to generate antibodies which recognize the Exp. Such antibodies include but are not limited to polyclonal, monoclonal, chimeric, single chain, Fab fragments, and an Fab expression library.

Various procedures known in the art may be used for the production of polyclonal antibodies to a recombinant Exp or derivative or analog thereof. For the production of antibody, various host animals can be immunized by injection with the recombinant Exp, or a derivative (e.g., fragment) thereof, including but not limited to rabbits, mice, rats, etc. In one embodiment, the recombinant Exp or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially usefull human adjuvants such as BCG (bacille Calmette-Guerin) and *Corynebacterium parvum*.

For preparation of monoclonal antibodies directed toward an Exp or analog thereof, any technique which provides for the production of antibody molecules by continuous cell lines in culture may be used. These include but are not limited to the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, J. Bacteriol. 159–870; Neuberger et al., 1984, Nature 312:604–608; Takeda et al., 1985, Nature 314:452–454) by splicing the genes from a mouse antibody molecule specific for an Exp together with genes from a human antibody molecule of appropriate biological activity can be used; such antibodies are within the scope of this invention. Such human or humanized chimeric antibodies are preferred for use in passive immune therapy (described infra), since the human or humanized antibodies are much less likely than xenogenic antibodies to induce an immune response, in particular an allergic response, themselves.

According to the invention, techniques described for the production of single chain antibodies (U.S. Pat. No. 4,946,778) can be adapted to produce Exp-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for an Exp or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodifflusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an Exp, one may assay generated hybridomas for a product which binds to a Exp fragment containing such epitope. For selection of an antibody specific to an Exp from a particular strain of bacterium, one can select on the basis of positive binding to that particular strain of bacterium and a lack of binding to Exp another strain. For selecting an antibody specific to an Exp that is an antigen common to all or many strains of a particular bacterium, or to closely related species of bacteria, one can select on the basis of binding to that particular strain and to all or many other strains of that species, or to closely related species.

The foregoing antibodies can be used in methods known in the art relating to the localization and activity of Exp, e.g., for Western blotting, imaging Exp, measuring levels thereof in appropriate physiological samples, etc.

Vaccination and Passive Immune Therapy

Active immunity against Gram positive bacteria can be induced by immunization (vaccination) with an immunogenic amount of an exported protein, or an antigenic derivative or fragment thereof, and an adjuvant, wherein the exported protein, or antigenic derivative or fragment thereof, is the antigenic component of the vaccine. Preferably, the protein is conjugated to the carbohydrate capsule or capsules of one or more species of Gram positive bacterium. Covalent conjugation of a protein to a carbohydrate is well known in the art. Generally, the conjugation can proceed via a carbodiimide condensation reaction.

The exported protein alone or conjugated to a capsule or capsules cannot cause bacterial infection, and the active immunity elicited by vaccination with the protein according to the present invention can result in both an immediate immune response and in immunological memory, and thus provide long-term protection against infection by the bacterium. The exported proteins of the present invention, or antigenic fragments thereof, can be prepared in an admixture with an adjuvant to prepare a vaccine. Preferably, the exported protein, or derivative or fragment thereof, used as the antigenic component of the vaccine is an adhesin. More preferably, the exported protein, or derivative or fragment thereof, used as the antigenic component of the vaccine is an antigen common to all or many strains of a species of Gram positive bacteria, or common to closely related species of bacteria. Most preferably, the antigenic component of the vaccine is an adhesin that is a common antigen.

Selection of an adjuvant depends on the subject to be vaccinated. Preferably, a pharmaceutically acceptable adjuvant is used. For example, a vaccine for a human should avoid oil or hydrocarbon emulsion adjuvants, including complete and incomplete Freund's adjuvant. One example of an adjuvant suitable for use with humans is alum (alumina gel). A vaccine for an animal, however, may contain adjuvants not appropriate for use with humans.

An alternative to a traditional vaccine comprising an antigen and an adjuvant involves the direct in vivo introduction of DNA encoding the antigen into tissues of a subject for expression of the antigen by the cells of the subject's tissue. Such vaccines are termed herein "nucleic acid-based vaccines." Since the exp gene by definition contains a signal sequence, expression of the gene in cells of the tissue results in secretion of membrane association of the expressed protein. Alternatively, the expression vector can be engineered to contain an autologous signal sequence instead of the exp signal sequence. For example, a naked DNA vector (see, e.g., Ulmer et al., 1993, Science 259:1745–1749), a DNA vector transporter (e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990), or a viral vector containing the desired exp gene can be injected into tissue. Suitable viral vectors include retroviruses that are packaged in cells with amphotropic host range (see Miller, 1990, Human Gene Ther. 1:5–14; Ausubel et al., Current Protocols in Molecular Biology, §9), and attenuated or defective DNA virus, such as but not limited to herpes simplex virus (HSV) (see, e.g., Kaplitt et al., 1991, Molec. Cell. Neurosci. 2:320–330), papillomavirus, Epstein Barr virus (EBV), adenovirus (see, e.g., Stratford-Perricaudet et al., 1992, J. Clin. Invest. 90:626–630), adeno-associated virus (AAV) (see, e.g., Samulski et al., 1987, J. Virol. 61:3096–3101; Samulski et al., 1989, J. Virol. 63:3822–3828), and the like. Defective viruses, which entirely or almost entirely lack viral genes, are preferred. Defective virus is not infective after introduction into a cell.

Vectors containing the nucleic acid-based vaccine of the invention can be introduced into the desired host by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

Either vaccine of the invention, i.e., a vaccines comprising an Exp antigen or antigenic derivative or fragment thereof, or an exp nucleic acid vaccine, can be administered via any parenteral route, including but not limited to intramuscular, intraperitoneal, intravenous, and the like. Preferably, since the desired result of vaccination is to elucidate an immune response to the antigen, and thereby to the pathogenic organism, administration directly, or by targeting or choice of a viral vector, indirectly, to lymphoid tissues, e.g., lymph nodes or spleen. Since immune cells are continually replicating, they are ideal target for retroviral vector-based nucleic acid vaccines, since retroviruses require replicating cells.

Passive immunity can be conferred to an animal subject suspected of suffering an infection with a Gram negative bacterium by administering antiserum, polyclonal antibodies, or a neutralizing monoclonal antibody against the Gram positive bacterium to the patient. Although passive immunity does not confer long term protection, it can be a valuable tool for the treatment of a bacterial infection of a subject who has not been vaccinated. Passive immunity is particularly important for the treatment of antibiotic resistant strains of Gram positive bacteria, since no other therapy is available. Preferably, the antibodies administered for passive immune therapy are autologous antibodies. For example, if the subject is a human, preferably the antibodies are of human origin or have been "humanized," in order to minimize the possibility of an immune response against the antibodies.

An analogous therapy to passive immunization is administration of an amount of an exported protein adhesin sufficient to inhibit adhesion of the bacterium to its target cell. The required amount can be determined by one of ordinary skill using standard techniques.

The active or passive vaccines of the invention, or the administration of an adhesin, can be used to protect an animal subject from infection of a Gram positive bacteria. Thus, a vaccine of the invention can be used in birds, such as chickens, turkeys, and pets; in mammals, preferably a human, although the vaccines of the invention are contemplated for use in other mammalian species, including but not limited to domesticated animals (canine and feline); farm animals (bovine, ovine, equine, caprine, porcine, and the like); rodents; and undomesticated animals.

Diagnosis of a Gram Positive Bacterial Infection

The antibodies of the present invention that can be generated against the exported proteins from Gram positive bacteria are valuable reagents for the diagnosis of an infection with a Gram positive microorganism. Presently, diagnosis of infection with a Gram positive bacterium is difficult. According to the invention, the presence of Gram positive bacteria in a sample from a subject suspected of having an infection with a Gram positive bacterium can be detected by detecting binding of an antibody to an exported protein to bacteria in or from the sample. In one aspect of the invention, the antibody can be specific for a unique strain or a limited number of strains of the bacterium, thus allowing for diagnosis of infection with that particular strain (or strains). Alternatively, the antibody can be specific for many or all strains of a bacterium, thus allowing for diagnosis of infection with that species.

Diagnosis of infection with a Gram positive bacterium can use any immunoassay format known in the art, as desired. Many possible immunoassay formats are described in the section entitled "Preparation of Antibodies to Exported Proteins." The antibodies can be labeled for detection in vitro, e.g., with labels such as enzymes, fluorophores, chromophores, radioisotopes, dyes, colloidal gold, latex particles, and chemiluminescent agents. Alternatively, the antibodies can be labeled for detection in vivo, e.g., with radioisotopes (preferably technetium or iodine); magnetic resonance shift reagents (such as gadolinium and manganese); or radio-opaque reagents.

Alternatively, the nucleic acids and sequences thereof of the invention can be used in the diagnosis of infection with a Gram positive bacterium. For example, the exp genes or hybridizable fragments thereof can be used for in situ hybridization with a sample from a subject suspected of harboring an infection of Gram positive bacteria. In another embodiment, specific gene segments of a Gram positive bacterium can be identified using PCR amplification with probes based on the exp genes of the invention. In one aspect of the invention, the hybridization with a probe or with the PCR primers can be performed under stringent conditions, or with a sequence specific for a unique strain or a limited number of strains of the bacterium, or both, thus allowing for diagnosis of infection with that particular strain (or strains). Alternatively, the hybridization can be under less stringent conditions, or the sequence may be homologous in any or all strains of a bacterium, thus allowing for diagnosis of infection with that species.

The present invention will be better understood from a review of the following illustrative description presenting the details of the constructs and procedures that were followed in its development and validation.

EXAMPLE 1

GENETIC IDENTIFICATION OF EXPORTED PROTEINS IN STREPTOCOCCUS PNEUMONIAE

A strategy was developed to mutate and genetically identify exported proteins in Streptococcus pneumoniae. Coupling the technique of mutagenesis with gene fusions to phoA, we have developed a tool for the mutation and genetic identification of exported proteins from *S. pneumoniae*. Vectors were created and used to screen pneumococcal DNA in *Escherichia coli* and *S. pneumoniae* for translational gene fusions to alkaline phosphatase (PhoA). In this study the identification of several genetic loci that encode exported proteins is reported. By similarity to the derived sequences from other genes from prokaryotic organisms these loci probably encode proteins that play a role in signal transduction, macromolecular transport and assembly, maintaining an intracellular chemiosmotic balance and nutrient acquisition.

Twenty five PhoA$^+$ pneumococcal mutants were isolated and the loci from eight of these mutants showed similarity to known exported or membrane associated proteins. Homologs were found to: 1] protein dependent peptide permeases, 2] penicillin binding proteins, 3] Clp proteases, 4] two component sensor regulators, 5] the phosphoenolpyruvate:carbohydrate phosphotransferase permeases, 6] membrane associated dehydrogenases, 7] P-type ($E_1E_2$-type) cation transport ATPases, 8] ABC transporters responsible for the translocation of the RTX class of bacterial toxins. Unexpectedly one PhoA$^+$ mutant contained a fusion to a member of the D-E-A-D protein family of ATP-dependent RNA helicases suggesting export of these proteins.

Materials and Methods

Strains and media.

The parent strain of *S. pneumoniae* used in these studies was R6x, which is a derivative of the unencapsulated Rockefeller University strain R36A (Tiraby and Fox, 1973, Proc. Natl. Acad. Sci. U.S.A. 70:3541–3545). *E. coli* strains used were DH5α, which is F$^-$ f80dlacZ Δ(lacZYAΔM15) lacU169 recA1 enda1 hsdR17 ($r_K^-$-$m_{K+}$) supE44 1$^-$ thy-1 gyrA relA1 (Bethesda Research Laboratories); CC118, which is Δ(ara leu)7697 ΔlacX74 araD139 phoA20 galE galK thi rpsE rpoB argE recA1 (Manoil and Beckwith, 1985, Proc. Natl. Acad. Sci. U.S.A. 82:8129–8133), S1179 which is F$^-$ ΔlacU169 dam3 rpsL (Brown, 1987, Cell. 49:825–33); and JCB607, which contains an expression vector for the production DsbA (rna met pBJ41 pMS421) (Bardwell et al., 1991, Cell. 67:581–589). Strains of *S. pneumoniae* and their relevant characteristics generated in this study are listed in Table 1.

TABLE 1

Bacterial Strains of *Streptococcus pneumoniae* created in this study.

| Strain | Relevant characteristics | Gene Family or Homolog[a] | Source |
|---|---|---|---|
| R6x | Hex, Parent strain | | (Tiraby and Fox, 1973) |
| SPRU2 | PhoA fusion to signal sequence 1 | | Current study |
| SPRU37 | PhoA fusion to signal sequence 2 | | Current study |
| SPRU96 | pHRM100::zzz | | Current study |
| SPRU97 | pHRM104::zzz | | Current study |
| SPRU121 | PhoA fusion to AmiA | peptide permeases | Current study |
| SPRU98 | PhoA fusion to Exp1 | peptide permeases | Current study |
| SPRU42 | PhoA fusion to Exp2 (PonA) | penicillin binding protein 1a | Current study |

TABLE 1-continued

Bacterial Strains of *Streptococcus pneumoniae* created in this study.

| Strain | Relevant characteristics | Gene Family or Homolog[a] | Source |
|---|---|---|---|
| SPRU40 | PhoA fusion to Exp3 | two component family of sensor regulators | Current study |
| SPRU39 | PhoA fusion to Exp4 | Clp proteases | Current study |
| SPRU87 | PhoA fusion to Exp5 | PTS family of permeases | Current study |
| SPRU24 | PhoA fusion to Exp6 | glycerol-3-phosphate dehydrogenase; GlpD; *B. subtilis* | Current study |
| SPRU75 | PhoA fusion to Exp7 | P-type cation transport ATPases | Current study |
| SPRU81 | PhoA fusion to Exp8 | RTX type traffic ATPases | Current study |
| SPRU17 | PhoA fusion to Exp9 | ATP dependent RNA helicases | Current study |

[a]The derived amino acid sequences were determined from plasmids recovered from the PhoA$^+$ mutants. Homologs were identified by searching a protein database with the BLAST algorithm. See FIG. 5 for alignments.

*S. pneumoniae* were routinely plated on tryptic soy agar supplemented with sheep blood (TSAB) to a final concentration of 3% (vol./vol.). Cultures were also grown in a liquid semi synthetic casein hydrolysate medium supplemented with yeast extract (C+Y medium) (Lacks and Hotchkiss, 1960, Biochem. Biophys. Acta. 39:508–517). In some instances, *S. pneumoniae* were grown in Todd Hewitt broth (THBY) supplemented with yeast to a final concentration of 5% (w/v).

Where indicated, *S. pneumoniae* was grown in C+Y in the presence of the disulfide oxidant 2-hydroxyethyl disulfide at a concentration of 600 μM, which is 5 times less than the minimal inhibitory concentration required for growth. *E. coli* were grown in either liquid or on solid Luria-Bertani (LB) media. Selection of *E. coli* with plasmid vectors was achieved with erythromycin (erm) at a concentration of 500 μg/ml. For the selection and maintenance of *S. pneumoniae* containing chromosomally integrated plasmids, bacteria were grown in the presence of 0.5 to 1 μg/ml of erm.

Transformation of *S. pneumoniae* was carried out as follows: Bacteria were grown in C+Y medium at 37° C. and samples were removed at 10 min. intervals between an O.D.$_{620}$ of 0.07 and 0.15 and stored at −70° C. in 10% glycerol. Samples were thawed on ice and DNA (final concentration, 1 μg/ml) was added before incubation at 37° C. for 90 min. Transformants were identified by selection on TSAB containing the appropriate antibiotic.

Recombinant DNA techniques

Plasmids pHRM100 and pHRM104 (FIG. 1) were constructed by insertion of either the 2.6 kB SmaI or BamHI fragments of pPHO7, which contain the truncated gene for phoA (Guitierrez and Devedjian, 1989, Nucleic Acid Res. 17:3999), into the corresponding sites in pJCD9 (Chen and Morrison, 1988, Gene. 64:155–164). A unique SmaI cloning site for pHRM100 and a unique BamHI cloning site for pHRM104 upstream from phoA were generated by selective deletion of duplicated sites.

Chromosomal DNA from *S. pneumoniae* was prepared by the following procedure: Cells were grown in 10 ml of THBY or C+Y with 0.5 μg/ml erm to an O.D.$_{620}$ of 0.7. The cells were isolated by centrifugation and washed once in 500 μl of TES (0.1M Tris-HCl, pH 7.5; 0.15M NaCl, 0.1M ethylenediaminetetra-acetic acid (EDTA)). The supernatant was discarded and the pellet resuspended in 500 μl of fresh TES. Bacteria were lysed with the addition of 50 μl of 1% (vol./vol.) deoxycholate. The lysate was sequentially incubated with RNase (2 μg) and pronase (400 ng) for 10 min. at 37° C. This solution was extracted three times with an equal volume of phenol:chloroform:isoamyl alcohol (25:24:1), followed by one extraction with an equal volume of chloroform:isoamyl alcohol (24:1). The DNA was precipitated with the addition of two volumes of cold ethanol, washed once with 70% ethanol, and resuspended in 10 mM Tris-HCl, pH 8.0, 1 mM EDTA. In some instances this protocol was adjusted to accommodate 400 ml of bacteria.

Plasmid libraries containing pneumococcal DNA were created with pHRM100 and pHRM104 in E. coli for insertion duplication mutagenesis in S. pneumoniae. Chromosomal DNA from S. pneumoniae was digested for 18 hr. with either AluI or RsaI or for 1.5 hr. with Sau IIIa. This DNA was size fractionated on a 0.7% agarose gel and 400–600 base pair fragments were extracted and purified with glass beads (BIO 101 Inc., La Jolla, Calif.) according to the manufacturer's instructions. DNA was ligated for 18 hr. at 4° C. into either the SmaI or BamHI sites of pHRM100 or pHRM104, respectively, at insert to vector ratio of 6:1. The ligation mixture was transformed into the E. coli strain S1179 or the PhoA⁻ strain CC118. Plasmid DNA was obtained from these libraries using the Qiagen midi plasmid preparation system (Qiagen Inc., Chatsworth, Calif.) according to the manufacturer's instructions.

The mutagenesis strategy in S. pneumoniae involved insert duplication upon plasmid integration (FIG. 1b). Because of this duplication there was a low frequency excision of the integrated plasmid with its insert that contaminated chromosomal preparations of pneumococcal DNA. Therefore, integrated plasmids containing a pneumococcal insert were easily recovered from S. pneumoniae by transformation of these excised plasmids directly into competent E. coli.

To create a gene fusion between the phoA and amiA, a 600 base pair fragment of amiA was obtained by the polymerase chain reaction of chromosomal DNA from S. pneumoniae using the forward and reverse primers:

5'AAAGGATCCATGAARAARAAYMGHGTNTTY3' (SEQ ID NO:40), and

5'TTTGGATCCGTTGGTTTAGCAAAATCGCTT3' (SEQ ID NO:41) respectively, where R=A/G, Y=T/C, M=C/A, H=T/C/A and N=G/A/T/C. Amplification of DNA was carried out with 50 ng of chromosomal DNA, 2 mM of the forward primer, 1 mM of the reverse primer and 2.5 U of AmpliTaq DNA polymerase (Perkin Elmer, Norwalk, Conn.), dNTPs and buffer provided by the manufacturer. Amplification (30 rounds) was carried out using the following procedure: 1 min. at 94° C. for denaturation, 2 min. at 72° C. for extension, and 1 min. at 45° C. for reannealing. A 600 base pair fragment was obtained, digested with BamHI and ligated into the corresponding site of pHRM104. This mixture was transformed into E. coli and a single recombinant clone that contained the vector with the insert was identified. An inframe coding sequence across the fusion joint was confirmed by sequence analysis. Plasmid DNA from this clone was transformed into S. pneumoniae and transformants were screened for PhoA activity by the colony lift assay to confirm production and export of the fusion protein.

DNA sequencing.

Oligonucleotides (5'AATATCGCCCTGAGC3', SEQ ID NO:42; and 5'ATCACGCAGAGCGGCAG3', SEQ ID NO:43) were designed for sequencing across the fusion joints of the pneumococcal inserts into pHRM100 and pHRM104. Double stranded sequence analysis was performed on plasmid DNA by the dideoxy-chain termination method (Sanger et al., 1977, Proc. Natl. Acad. Sci. U.S.A. 74:5463–5467) using the Sequenase Version 2.0 DNA sequencing kit (United States Biochemical Corp., Cleveland, Ohio) according to the manufacturer's instructions. Dimethylsulfoxide (1% vol./vol.) was added to the annealing and extension steps.

Alkaline phosphatase activity.

Even though alkaline phosphatase has been characterized in some Gram positive organisms such as Enterococcus faecalis (Rothschild et al., 1991, In "Genetics and Molecular Biology of Streptococci, Lactococci, and Enterococci.", Dunny, et al., Washington D.C. American Society for Microbiology, pp. 45–48) and B. subtilis (Chesnut et al., 1991, Mol. Microbiol. 5:2181–90; Hulett et al., 1991, J. Biol. Chem. 266:1077–84; Sugahara et al., 1991, J. Bacteriol. 173:1824–6), nothing is known about this enzyme in S. pneumoniae. PhoA activity associated with the parental strain of S. pneumoniae was measured with chromogenic substrates in the assays described below and gave nominal results. Therefore, detection of PhoA activity due to the expression of fusion proteins in S. pneumoniae was performed in a low or negative background.

To screen for pneumococcal derived PhoA fusions in E. coli, plasmid libraries were screened in the PhoA⁻ strain CC118. Transformants were plated on LB media supplemented with 40 to 80 μg/ml of the chromogenic substrate 5-bromo4-chloro-3-indolyl phosphate (XP). Blue colonies developed in 15 to 24 hr. and indicated PhoA activity. Individual colonies were streak purified on fresh LB/XP plates to verify the blue phenotype.

To screen for PhoA⁺ mutants of S. pneumoniae, individual colonies were screened in a colony lift assay with XP as adapted from a previously described procedure (Knapp and Mekalanos, 1988, J. Bacteriol. 170:5059–5066). Individual two day old colonies were transferred to nitrocellulose filters (HAHY, Millipore, Bedford, Mass.) and air dried for two to five min. The filters were placed colony side up on No. 3 filter papers (Whatman, Inc. Clifton, N.J.), pre-soaked in 0.14M NaCl, and incubated for 10 min. at 37° C. This was repeated once and then the membranes were transferred to fresh filter papers pre-soaked in 1M Tris-HCl, pH 8.0 and incubated for 10 min. at 37° C. Finally the membranes were transferred to another fresh filter paper soaked in 1M Tris-HCl, pH 8.0, with 200 μg/ml of XP and incubated at 37° C. Blue colonies indicated PhoA⁺ mutants and were detected in 10 min. to 18 hr. Colonies were picked either directly from the filters or from the original plates. After colonies were streak purified on TSAB plates, the blue phenotype was reconfirmed in a subsequent colony lift assay.

PhoA activity expressed in strains of S. pneumoniae was determined from exponentially growing cultures. Bacteria from 10 ml cultures were isolated by centrifugation, washed once in saline and resuspended in 1 ml of 1M Tris-HCl, pH 8.0. Activity was determined by hydrolysis of p-nitrophenol phosphate in a previously described assay (Brickman and Beckwith, 1975, Mol. Biol. 96:307–316; Guitierrez et al., 1987, J. Mol. Biol. 195:289–297). Total protein was determined on lysed bacteria with Coomassie blue dye (Bradford, 1976, Anal. Biochem. 72:248–254).

Purification of DsbA.

DsbA was purified to near homogeneity from an E. coli strain (JCB607) that contains an expression vector with the corresponding gene (Bardwell et al., 1991, Cell. 67:581–589). Briefly, 2 ml of a fresh overnight culture was added to 400 ml of LB media and grown for 2 hr. at 37 ° C. The culture was adjusted to 3 mM isopropyl β-D-thiogalactopyranoside (IPTG) and grown for an additional 2 hr. Bacteria were isolated by centrifugation and resuspended in 6 ml of 100 mM Tris-HCl pH 7.6, 5 mM EDTA and 0.5M sucrose. This suspension was incubated for 10 min. on ice and the cells isolated by centrifugation. Bacteria were resuspended in 6 mL of 5 mM MgCl$_2$ and incubated for 10 min. on ice. The supernatant was isolated after centrifugation. This material contained a predominant Coomassie blue stained band with an apparent M$_r$ of 21 kDa on an SDS polyacrylamide gel, which is identical to that of DsbA, and was judged to be approximately 95% pure (data not shown).

Subcellular fractionation.

Pneumococci were separated into subcellular fractions by a modification of a previously described technique (Hakenbeck et al., 1986, Antimicrobial agents and chemotherapy. 30:553–558). Briefly, bacteria were grown in 10 ml of C+Y medium to an O. D.$_{.620}$ of 0.6, and isolated by centrifugation at 17,000×g for 10 min. Cell pellets were resuspended in 250 μl of TEP (25 mM Tris-HCl pH 8.0, 1 mM EDTA, 1 mM phenyl methyl sulfonyl fluoride). The suspension was sonicated for a total of 4 min. with 15 sec. bursts. Greater than 99% of the bacteria were broken as revealed by visual inspection. Cellular debris was removed by centrifugation (17,000×g for 10 min.). The bacterial membranes and the cytoplasmic contents were separated by centrifugation at 98,000×g for 4 hr in a Beckman airfuge. The supernatant from this final step contained the cytoplasmic fraction while the pellet contained the bacterial membranes. Samples from each fraction were evaluated for protein content and solubilized in SDS sample buffer for subsequent gel electrophoresis.

Immunological detection of fusion proteins.

Total bacterial lysates and subcellular fractions were subjected to SDS-polyacrylamide gel electrophoresis and proteins transferred to nitrocellulose membranes (Immobilon, Millipore, Bedford, Mass.) using the PhastSystem (Pharmacia LKB, Uppsula Sweden) according to the manufacturer's instructions. The membranes were probed with polyclonal anti-PhoA antibodies (5 Prime-3 Prime, Boulder, Colo.) at a dilution of 1:1000, with a peroxidase conjugated second antibody at a dilution of 1:1000. Immunoreactive bands were detected with hydrogen peroxide and diaminobenzidine or by enhanced chemiluminescence with chemicals purchased from Amersham (Arlington Heights, Ill.).

Results and Discussion

Construction of reporter plasmids and pneumococcal libraries.

In order to genetically screen for exported proteins in S. pneumoniae by insertion duplication mutagenesis, a truncated form of phoA (Guitierrez and Devedjian, 1989, Nucleic Acid Res. 17:3999) was placed in the pneumococcal shuttle vector pJDC9 (FIG. 1a) (Chen and Morrison, 1988, Gene. 64:155:164) Two vectors were created with either a unique SmaI (pHRM100) or a unique BamHI (pHRM104) cloning site 5' to phoA. The cloning sites in each vector are flanked by two KpnI sites to facilitate easy identification of an insert.

Efficient insertion duplication mutagenesis requires the cloning of an internal gene fragment within the vector prior to integration (FIG. 1b). Therefore plasmid libraries were created in E. coli with 400 to 600 base pair inserts of pneumococcal DNA. Several libraries representing approximately 2,600 individual clones were screened for translational fusions to phoA in either E. coli or S. pneumoniae.

Identification of pneumococcal PhoA fusions in E. coli.

When the pneumococcal libraries representing 1,100 independent clones were screened in the PhoA$^-$E. coli strain CC118 fifty five colonies displayed the blue phenotype when plated on media containing 5-bromo-4-chloro-3-indolyl phosphate (XP). Since the cloning vectors pHRM100 and pHRM104 do not contain an intrinsic promoter upstream from phoA, fusion proteins derived from these plasmids must have been generated from pneumococcal DNA that contains a promoter, a translational start site and functional signal sequence. DNA sequence analysis of the inserts from two of these plasmids showed a putative promoter, ribosome binding sites and coding sequences for 48 and 52 amino acids that were inframe with the coding sequence for phoA. These coding sequences have features characteristic of prokaryotic signal sequences such as a basic N-terminal region, a central hydrophobic core and a polar C-terminal region (von Heijne, 1990, J. Memb. Biol. 115:195–201) (Table 2).

TABLE 2

Predicted coding regions from two genetic loci that produced PhoA fusion proteins in both S. pneumoniae and E. coli.

Strain Signal sequence$^a$

| | | |
|---|---|---|
| SPRU2 | MKHLLSYFKPYIKESILAPLFKLLEAVFELLVPMVIA↑GIVDQSLPQ GDPRVP | (SEQ ID NO:44) |
| SPRU37 | MAKNNKVAVVTTVPSVAEGLKNVNG↑VNFDYKDEASAKEAIKEE KLKGYLTIDPRVP | (SEQ ID NO:45) |

$^a$The coding regions were identified from the DNA sequences 5' to phoA from the plasmids recovered from these strains. The arrow indicates the predicted signal peptide cleavage site based on the "-3, -1 rule" (von Heijne, 1986, Nucleic Acid Res. 14:4683–4690) and the amino acids in bold face type are from the coding region for phoA.

A putative cleavage site was identified in both sequences with an algorithm designed to identify such sites based on the "-3, -1 rule" (von Heijne, 1986, Nucleic Acid Res. 14:4683–4690). Transformation and integration of these plasmids into S. pneumoniae gave transformants that produced blue colonies in the colony lift assay and each produced anti-PhoA immunoreactive fusion proteins with an apparent M$_r$ of 55 kDa on SDS polyacrylamide gels (data not shown). These results clearly show that heterologous signal sequences from S. pneumoniae fused to PhoA are functional in both E. coli and S. pneumoniae and probably use a similar secretion pathway.

PhoA fusions to an exported pneumococcal protein.

AmiA is a pneumococcal representative of the family of bacterial permeases that are responsible for the transport of small peptides (Alloing et al., 1989, Gene. 76:363–8; Alloing et al., 1990, Mol. Microbiol. 4:633–44; Gilson et al., 1988, EMBO J. 7:3971–3974). AmiA contains a signal sequence and should be an exported lipoprotein attached to the bacterial membrane by a lipid moiety covalently linked to the N-terminal cysteine (Gilson et al., 1988, EMBO J. 7:3971–3974). We genetically engineered a pneumococcal mutant (SPRU121) that contained the 5' coding region of amiA fused inframe at codon 169 to phoA. Colonies of this mutant produced the blue phenotype when exposed to XP suggesting that the hybrid protein was exported. An immunoreactive polypeptide with the predicted $M_r$ of 67 kDa was confirmed by Western analysis of a total cell lysate (data not shown).

Identification of PhoA fusions in S. pneumoniae.

Encouraged by the detection of PhoA fusions derived from pneumococcal DNA in both E. coli and S. pneumoniae, we created a library of pneumococcal transformants that contained random chromosomal insertions of the PhoA vectors pHRM100 and pHRM104. From a bank of 1,500 clones, 75 mutants were isolated that displayed the blue phenotype in the colony lift assay with XP. Because S. pneumoniae spontaneously lyse during stationary growth due to an endogenous amidase (LytA), we were concerned that the blue phenotype of some of the mutants was the result of cell lysis and not due to the export of a fusion protein from viable cells. The DNA from 10 random blue mutants that included SPRU22, 42, 75, 81, and 98 was transformed into a lytA minus background and all still displayed the blue phenotype (data not shown).

Figure 2:
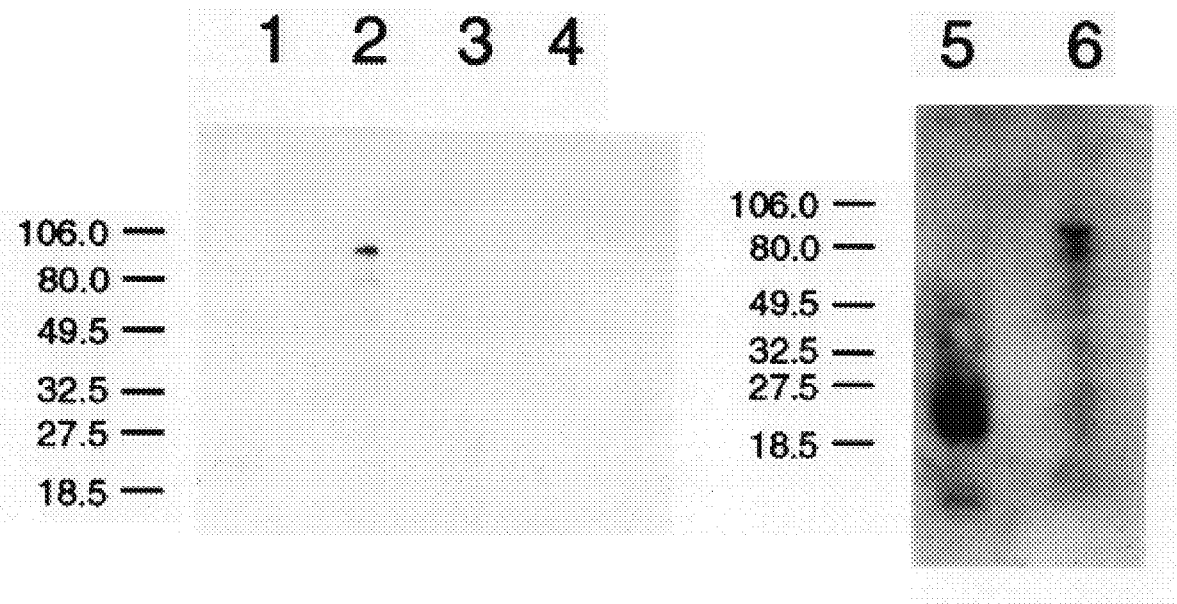
FIG. 2. Detection and trypsin susceptibility of PhoA fusions in S. pneumoniae. Total cells lysates (50 μg of protein) from R6x (lane 1; parental strain): SPRU98 (lane 2); SPRU97 (lane 3); and SPRU96 (lane 4) were applied to an 8–25% SDS polyacrylamide gel. Proteins were transferred to nitrocellulose membranes and probed with anti-PhoA antibody. Antigen-antibody complexes were detected by enhanced chemiluminescence with an appropriate peroxidase conjugated second antibody. SPRU96 and 97 contain the plasmids pHRM100 and pHRM104 randomly integrated in the chromosome. Molecular weight standards are indicated on the left. Whole bacteria from strain SPRU98 were treated with (lane 5) and without (lane 6) 50 μg/ml of trypsin for 10 min. at 37° C. Both samples were treated with a 40 fold molar excess of soy bean trypsin inhibitor. The total cell lysates (50 μg protein) were probed for immunoreactive material to PhoA as described above. Molecular weight standards are indicated on the left.

One of the mutants (SPRU98) displayed the blue phenotype on XP and expressed a 93 kDa anti-PhoA immunoreactive polypeptide (FIG. 2; lane 2). Since the coding region to phoA would produce a polypeptide with a molecular mass of 49 kDa, we can conclude that the fusion protein was being produced from a coding region corresponding to a polypeptide with a molecular mass of 44 kDa. In contrast, mutants SPRU96 and 97, that contained randomly inserted vectors and were not blue when exposed to XP, did not produce any immunoreactive material (FIG. 2; lanes 3, 4). The fusion protein from SPRU98 was proteolytically degraded when whole bacteria were exposed to low concentrations of trypsin suggesting an extracellular location (FIG. 2, lane 5). Consistent with this result was the direct measurement of alkaline phosphatase activity associated with whole bacteria. Compared to the parental strain and a PhoA mutant (SPRU97) with a randomly integrated plasmid, there was a three- to four-fold greater enzyme activity for SPRU98 (Table 3). Collectively these results suggest that PhoA fusions to exported proteins were translocated across the cytoplasmic membrane of S. pneumoniae.

TABLE 3

Alkaline phosphatase activity for a pneumococcal mutant with a gene fusion to phoA

| Strain | Integrated phoA vector[a] | Colony lift assay[b] | Phosphatase activity[c] |
|---|---|---|---|
| SPRU98 | + | blue | 44.7 ± 6 |
| SPRU97 | + | white | 18.4 ± 5 |
| R6x | 0 | white | 14.6 ± 4 |

[a]SPRU97 and SPRU98 contain the phoA vector pHRM104 randomly integrated into the chromosome as described in the text.
[b]The PhoA+ mutant was isolated based on the expression of alkaline phosphatase activity detected by exposure of individual colonies to XP in the colony lift assay.
[c]Units of alkaline phosphatase activity were determined as described in Experimental procedures. The assay was performed on washed cells from exponentially growing cultures. The results are presented as units of enzyme activity/mg of total protein.

Disulfide oxidants increase the enzyme activity of PhoA fusions in S. pneumoniae.

In E. coli, PhoA activity requires protein translocation across the cytoplasmic membrane, incorporation of $Zn^{2+}$, disulfide bond formation and dimerization. Following this activation process the enzyme is highly protease resistant (Roberts and Chlebowski, 1984). Recently two groups have identified a single genetic locus, dsbA (Bardwell et al., 1991, Cell. 67:581–589), and ppfA (Kamitani et al., 1992, EMBO J. 11:57–67), that encodes a disulfide oxidoreductase, which facilitates the formation of disulfide bonds in PhoA. A similar locus has also been identified in V. cholerae (Peek and Taylor, 1992, Proc. Natl. Acad. Sci. 89:6210–6214). Mutations in dsbA dramatically decreased PhoA activity and rendered the protein protease sensitive both in vitro and in vivo (Bardwell et al., 1991, Cell. 67:581–589; Kamitani et al., 1992, EMBO J. 11:57–67). Since the enzyme activity associated with the PhoA fusions in S. pneumoniae was universally 10 fold lower than values obtained with fusions in E. coli (data not shown) and due to the protease sensitivity of the PhoA fusion depicted in FIG. 2, we hypothesized that the addition of DsbA or a strong disulfide oxidant would promote disulfide bond formation, increase enzyme activity and retard proteolytic degradation.

SPRU98 which produces a PhoA fusion protein with an $M_r$ of 93 kDa was grown in either the presence of 10 μM DsbA or 600 μM 2-hydroxyethel disulfide, a strong disulfide oxidant. Under both conditions enzyme activity was increased at least two fold (Table 4).

TABLE 4

Effect of disulfide oxidants on the alkaline phosphatase activity

| Agent | |
|---|---|
| 10 μM DsbA | 138.4 ± 7 |
| 600 μM 2-hydroxyethel disulfide | 107.5 ± 8 |
| Control | 51.2 ± 5 |

[a]The strain SPRU98 (10 ml) was grown in the presence of the indicated agents to mid log phase ($OD_{620}$: 0.4), concentrated and assayed for alkaline phosphatase activity. Hydrolysis of p-nitrophenol phosphate was determined with whole bacteria in the presence of 1M Tris-HCl, pH 8.0 for one hr. at 37° C. Activity units are expressed per mg of total protein.

Figure 3:
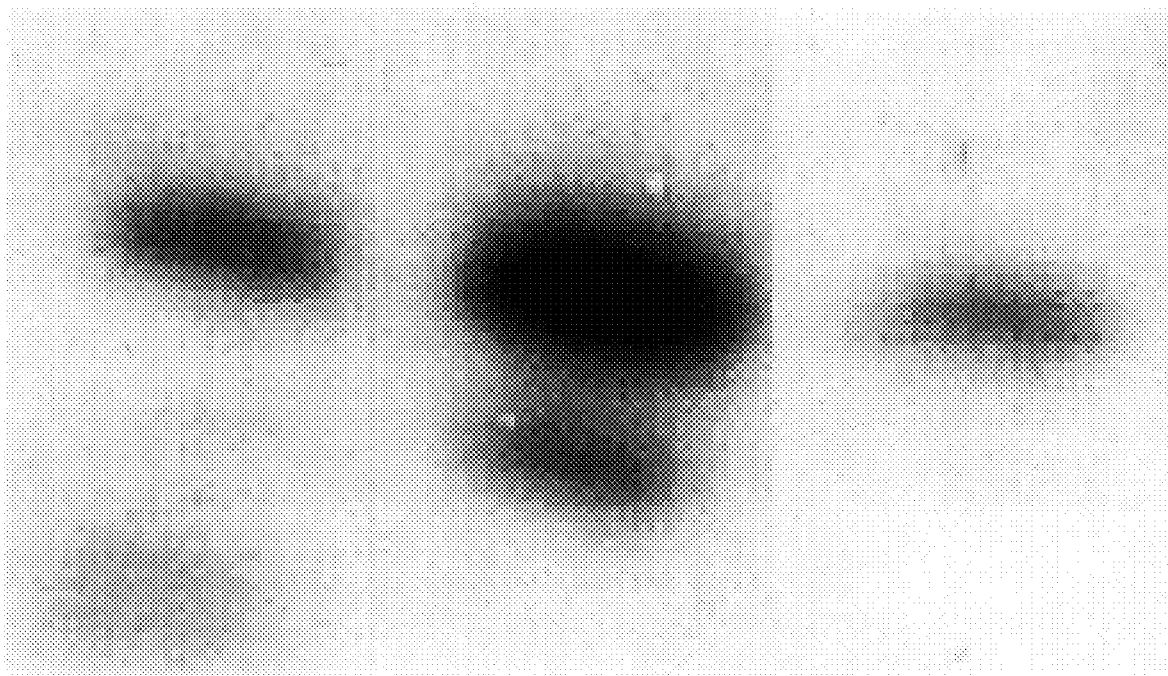
FIG. 3. PhoA fusion products are more stable when bacteria are grown in the presence of disulfide oxidants. Cultures of SPRU98 were grown in the presence of either 600 μM 2-hydroxyethel disulfide (lane 1), 10 μM DsbA (lane 2) or without any additions (lane 3). Total cell lysates (50 μg of protein) were applied to an 8–25% SDS polyacrylamide gel. The proteins were then probed for inmmunoreactive material with anti PhoA antibody as described in FIG. 2.

Compared to the control, there was also an increased amount of immunoreactive protein detected in the presence of these two compounds (FIG. 3). This suggested increased protein stability and resistance to intrinsic proteolysis. Since there was only a modest increase in enzyme activity conveyed by these compounds, we propose that there may be other factors required for the correct folding of PhoA that are absent in S. pneumoniae. It is of note that the derived sequences of other alkaline phosphatase isozymes identified in the Gram positive organisms B. subtilis (Chesnut et al., 1991, Mol. Microbiol. 5:2181–90; Hulett et al., 1991, J. Biol. Chem. 266:1077–84; Sugahara et al., 1991, J. Bacteriol. 173:1824–6) and Enterococcus faecalis contain only one or no cysteine residues. This may suggest that the presence of an oxido-reductase system for the correct folding of these intra or intermolecular disulfide bonds may be a unique property of some Gram negative organisms which contain a well defmed periplasm.

Identification of exported proteins by sequence analysis of the PhoA fusions from S. pneumoniae.

The plasmids containing pneumococcal inserts were recovered in E. coli from 48 pneumococcal mutants that displayed the blue phenotype on XP. Digestion of these plasmids with KpnI dissects the pneumococcal inserts from the parent vector. The size of the inserts were all approximately 400 to 900 base pair. Preliminary sequence analysis of the 48 inserts revealed 21 distinct sequences, thus demonstrating a sibling relationship between some of the mutants. Long coding regions corresponding to 50 to 200 amino acids inframe with PhoA were established for most of the inserts, nine of which are presented in FIG. 4. Using the BLAST algorithm (Altschul et al., 1990, J. Mol. Biol. 215:403–410), the derived protein sequences were analyzed for similarity to sequences deposited in the most current version of the non redundant protein database at the National Center for Biotechnology Information (Washington, D.C.). Sequence from these nine inserts (FIG. 4) revealed coding regions with similarity to families of eight known exported or membrane associated proteins (FIG. 5). Those proteins encoded by the genes that correspond to the potential reading frames without a known function are designated with the preface exp (exported protein) to describe the different genetic loci.

No similarity between the derived sequences from the other inserts to those in the data base was detected. The sequences for all nine inserts will be made available in Genbank (Accession numbers: to be assigned) after the filing date of this application.

Exp1 showed similarity to the family of permeases responsible for the transport of small peptides in both Gram negative and Gram positive bacteria (FIG. 5A). The reading frame identified showed the greatest similarity to the exported protein, AmiA, from S. pneumoniae (Alloing et al., 1990, Mol. Microbiol. 4:633–44). The ami locus was first characterized in a spontaneous mutant resistant to aminopterin (Sicard, 1964, Genetics. 50:31–44; Sicard and Ephrussi-Taylor, 1965). The wild type allele may be responsible for the intracellular transport of small branched chain amino acids (Sicard, 1964). Exp1 is clearly distinct from AmiA and represents a related member of the family of permeases present in the same bacteria. E. coli has at least three peptide permeases while B. subtilis has at least two (for a review see (Higgins et al., 1990, J. Bioengen. Biomembranes. 22:571–92)). Mutations in an analogous locus Spo0K from B. subtilis inhibit sporulation and dramatically decrease transformation efficiency in naturally competent cells (Perego et al., 1991, Mol. Microbiol. 5:173–85; Rudner et al., 1991, J. Bacteriol). Recent results have shown that mutations in exp1 also decrease transformation efficiency in S. pneumoniae whereas mutations in amiA did not. Therefore, two distinct peptide permeases from two different Gram positive bacteria affect the process of transformation in these naturally competent bacteria.

Both the DNA and derived protein sequences of exp2 were identical to ponA (basepairs 1821–2055) which encodes penicillin-binding protein 1A (PBP1a) (Martin et al., 1992a, J. Bacteriol. 174:4517–23) (FIG. 5B). This protein belongs to the family of penicillin-interacting serine D, D-peptidases that catalyze the late steps in murein biosynthesis. PBP1a is routinely isolated from pneumococcal membrane preparations and is generally considered an exported protein (Hakenbeck et al., 1991, J. Infect. Dis. 164:313–9; Hakenbeck et al., 1986, Antimicorbial Agents and Chemotherapy. 30:553–558; Martin et al., 1992, Embo J. 11:3831–6). In E. coli deletions of both PBP1a and PBP1b are lethal to the cell but the bacteria are able to compensate if either gene is deleted (Yousif et al., 1985, J. Gen. Microbiol. 131:2839–2845). It would be interesting to compare the peptidoglycan profile of SPRU42 to the parent strain to determine if the gene fusion to PBP1a alters enzyme function.

Exp3 showed significant sequence similarity to PilB from N. gonorrhoeae (FIG. 5C) (Taha et al., 1988, EMBO J. 7:4367–4378). There were two regions of similarity which correspond to the C-terminal domain of PilB. There was a short gap of 25 amino acids for Exp3 and 37 amino acids for PilB which showed no similarity. This suggests a modular structure function relationship for these two proteins. Consistent with this result, PhoA-PilB hybrids were localized to the membrane fraction of N. gonorrhoeae (Taha et al., 1991, Mol. Microbiol 5:137–48) indicating membrane translocation.

It has been suggested that PilA and PilB are members of the family of two component sensor regulators that control pilin gene expression and that PilB is a transmembrane sensor with the conserved transmitter region that contains kinase activity in the C-terminal region of the protein (Taha et al., 1991, Mol. Microbiol. 5:137–48; Taha et al., 1992, J. Bacteriol. 174:5978–81). The conserved histidine residue ($H_{408}$) in PilB required for autophosphorylation that is characteristic of this family is not present in Exp3. Since no pilin has been identified on S. pneumoniae one would assume a different target site for gene regulation by Exp3.

The coding region identified with Exp4 suggests that it is similar to the ubiquitous family of Clp proteins found in both eukaryotes and prokaryotes (FIG. 5D) (for a review see Squires and Squires, 1992, J. Bacteriol. 174:1081–1085). Exp4 is most similar to the homolog CD4B from tomato (Gottesman et al., 1990, Proc. Natl. Acad. Sci. U.S.A. 87:3513–7) but significant similarity was also noted to ClpA and ClpB from E. coli. It has been proposed that these proteins function either as regulators of proteolysis (Gottesman et al., 1990, Proc. Natl. Acad. Sci. U.S.A. 87:3513–7) or as molecular chaperones (Squires and Squires, 1992, J. Bacteriol. 174:1081–1085). One universal feature of the Clp proteins is a long leader sequence that implies membrane translocation (Squires and Squires, 1992, supra, J. Bacteriol. 174:1081–1085). Indeed, plant ClpC is translocated into chloroplasts (Moare, 1989, Ph.D. thesis. University of Wisconsin, Madison). Even though little is known about the subcellular localization of the other Clp proteins, our results suggest translocation of the pneumococcal homolog across the bacterial membrane.

Exp5 showed similarity to PtsG from B. subtilis (Gonzy-Tréboul et al., 1991, Mol. Microbiol. 5:1241–1249) which is a member of the family of phosphoenolpyruvate:carbohydrate phosphotransferase permeases that are found in both Gram positive and Gram negative bacteria (for a review see Saier and Reizer, 1992, J. Bacteriol. 174:1433–1448) (FIG. 5E). These permeases are polytopic membrane proteins with several translocated domains.

Analysis of the insert recovered from Exp6 revealed a coding region with similarity to glycerol-3-phosphate dehydrogenases from several prokaryotic species (FIG. 5F). It is most similar to GlpD from B. subtilis (Holmberg et al., 1990, J. Gen. Microbiol. 136:2367–2375). This enzyme is a membrane associated flavoprotein forming a complex with cytochrome oxidases which are integral membrane proteins. Besides converting glycerol-3-phosphate to dihydroxyacetone phosphate and glyceraldehyde-3phosphate for subsequent entry into the glycolytic pathway, this enzyme delivers electrons to the cytochrome oxidases for subsequent transport. It has been proposed that these dehydrogenases are bound to the inner surface of the cytoplasmic membrane via nonspecific hydrophobic interactions (Halder et al., 1982, Biochemistry. 21:4590–4606; Koland et al., 1984, Biochemistry. 23:445–453; Wood et al., 1984, Biochem. J. 222:519–534). Alternatively it has been proposed that there are a specific and saturable number of binding sites between the dehydrogenases and the cytochromes serving to anchor the dehydrogenases to the cytoplasmic membrane. The data reported here suggest that in S. pneumoniae a segment of the dehydrogenase is translocated to the outer surface of the bacteria (Kung and Henning, 1972, Proc. Natl. Acad. Sci. U.S.A. 69:925–929). Translocation of the catalytic domain would certainly not alter enzyme function. In reconstituted inside out membrane vesicles, electron transfer to the cytochromes occurred when dehydrogenases were added to either side of the vesicles (Halder et al., 1982, Biochemistry. 21:4590–4606).

Analysis of the derived sequence for Exp7 showed similarity to the family of both eukaryotic and prokaryotic P-type ($E_1E_2$-type) cation transport ATPases responsible for the transport of cations such as $Ca^{2+}$, $Mg^{2+}$, $K^+$, $Na^+$, and $H^+$(FIG. 5G). These ATPases are intrinsic membrane proteins with several translocated domains. Examples have been identified in *E. faecalis* (Solioz et al., 1987, J. Biol. Chem. 262:7358–7362), *Salmonella typhimurium* (Snavely et al., 1991, J. Biol. Chem. 266:815–823), *E. coli* (Hesse et al., 1984, Proc. Natl. Acad. Sci. U.S.A. 81:4746–4750), *Neurospora crassa* (Addison, 1986, J. Biol. Chem. 26:14896–14901; Hager et al., 1986, Proc. Natl. Acad. Sci. U.S.A. 83:7693–7697), *Saccharomyces cerevisiae* (Rudolph et al., 1989, Cell. 58:133–145) and the sarcoplasmic reticulum of rabbit skeletal muscle (Brandi et al., 1986, Cell. 44:597–607; Serrano et al., 1986, Nature. 689–693). Exp7 is most similar to MgtB from *S. typhimurium*, which is one of three genetic loci responsible for the transport of $Mg^{2+}$ (Snavely et al., 1991, J. Biol Chem. 266:815–823). The identified region contains the highly conserved aspartyl residue, which is the site for ATP dependent autophosphorylation. Based on the similarity to MgtB, the fusion in Exp7 probably occurred in the C-terminal region of the protein. A predicted model for the transmembrane loops of MgtB suggested that this region would be on the cytoplasmic surface (Snavely et al., 1991, J. Biol. Chem. 266:815–823). The data with the PhoA fusion to Exp7 suggests that location of this region on the cytoplasmic surface is not the case in *S. pneumoniae*.

Exp8 shows similarity to the family of traffic ATPases, alternatively called the ATP binding cassette (ABC) superfamily of transporters, which are found in both prokaryotes and eukaryotes (reviewed in Ames and Lecar, 1992, Faseb J. 6:2660–6) (FIG. 5H). Exp8 is most similar to the transmembrane proteins responsible for the translocation of bacterial RTX proteins such as the α-hemolysins, which are eukaryotic cytotoxins found in both Gram negative and Gram positive organisms (reviewed in Welch, 1991, Mol. Microbiol. 5:521–528). The fusion protein containing Exp8 is most similar to CyaB a component of the cya operon in *Bordetella pertussis* (Glaser et al., 1988, Mol. Microbiol. 2:19–30; Glaser et al., 1988, EMBO J. 7:3997–4004). This locus produces the adenylate cyclase toxin which is a also member of the RTX family of bacterial toxins. It does not go without notice that the comA locus in *S. pneumoniae* is also a member of this family (Hui and Morrison, 1991, J. Bacteriol. 173:372–81).

The derived sequence for exp9 from two regions of the recovered insert are presented in FIG. 4. Analysis of this sequence revealed that Exp9 is a member of the D-E-A-D protein family of ATP-dependent RNA helicases (for a review see (Schmid and Linder, 1992, Mol. Microbiol. 6:282–292)). It is most similar to DEAD from *E. coli* (FIG. 5I) (Toone et al., 1991, J. Bacteriol. 173:3291–3302). A large number of helicases have been identified from many different organisms. At least five different homologs have been identified in *E. coli* (Kalman et al., 1991, The New Biologist 3:886–895). The hallmark of these proteins is the conserved DEAD sequence within the B motif of an ATP binding domain (Walker et al., 1982, EMBO J. 1:945–951). The DEAD sequence was identified in the derived sequence from the 5' end of the insert from exp9.

Figure 6:
FIG. 6. Subcellular localization of the Exp9-PhoA fusion. The membrane (lane 1) and cytoplasmic (lane 2) fractions (50 μg of protein for each sample) of SPRU17 were applied to a 10–15% SDS polyacrylamide gel. The proteins were transferred to nitrocellulose and probed with anti-PhoA antibody. Molecular weight standards are indicated on the left.

Two studies have suggested that different homologs in *E. coli* may play a role in translation by affecting ribosome assembly (Nishi et al., 1988, Nature. 336:496–498; Toone et al., 1991, J. Bacteriol. 173:3291–3302). No published studies have reported either export or membrane association of these proteins. Therefore it was surprising to identify a PhoA$^+$ mutant harboring this fusion. Subcellular fractionation clearly shows the majority of the fusion protein associated with the membrane fraction of the bacteria (FIG. 6), although this could be an anomaly observed only with the fusion protein.

Recently, comF in *B. subtilis* has been shown to contain a similar RNA/DNA helicase with a DEAD sequence (Londoñó—Vallejo and Dubnau, Mol. Microbiol.). Mutations in this locus render the bacteria transformation deficient. Subsequent studies have shown the helicase to be a membrane associated protein and it has been suggested that it may play a role in the transport of DNA during transformation (D. Dubnau, personal communication). Preliminary experiments have not shown a great difference in the transformability of a mutant expressing the Exp9-PhoA fusion. If there are a class of helicases associated with the membrane, it is tempting to speculate that Exp9 may be involved in the translation of polypeptides destined to be exported.

In conclusion, this Example demonstrates the development of a technique that successfully mutated and identified several genetic loci in *S. pneumoniae* that encode homologs of known exported proteins. It is clear from our results that the majority of the loci that have been identified encode exported proteins that play a role in several diverse processes that occur either at the cytoplasmic membrane or outside the bacteria. As with the use of PhoA mutagenesis in other organisms, a note of caution is also advised with this technique in *S. pneumoniae*. Not all loci identified may encode exported proteins. It is certainly possible that due to several factors such as cell lysis some false positives may be generated. As demonstrated in the following Example, additional assays to demonstrate the functional activity of the mutant putative exported protein can be performed.

Given these results, the majority of the loci identified to date encode exported proteins, some of which play a role in signal transduction, protein translocation, cell wall biosynthesis, nutrient acquisition or maintaining a chemiosmotic balance.

EXAMPLE 2

MUTATION OF SOME EXPORTED PROTEINS AFFECTS ADHERENCE

In this Example, the ability of encapsulated and unencapsulated pneumococci to adhere to lung cells was determined. The results indicate that both types of pneumococci adhere to mixed lung cells and to Type II lung cells, although the preference was for type II cells. Also, the results suggest that the type 2 encapsulated strain has a slightly greater ability to adhere than the unencapsulated variant.

The effect of mutations to exported proteins on the ability of the mutated *S. pneumoniae* strains to adhere to human umbilical vein endothelial cells (HUVEC) and lung Type II cells was also assayed. The results demonstrated that some of the exported proteins have direct or indirect roles in adhesion of *S. pneumoniae* to either HUVEC or lung cells, or both.

Materials and Methods

Preparation of mixed and type II alveolar cells from rabbit.

As described by Dobbs and Mason (1979, J. Clin. Invest. 63:378–387), lungs were removed from the rabbit, minced and digested with collagenase, elastase and DNase for 60 min at 37° C. Large pieces were removed over a gauze filter and cells were pelleted and washed twice. The mixed lung cells were resuspended in 20 ml of calcium containing buffer supplemented with 0.5% albumin at a density of $10^4$ per ml. Alveolar type II cells were purified from the mixed lung cell suspension by layering the suspension on an albumin gradient of 10 ml at 16.5 g % over 10 ml at 35 g % and centrifuged at 1200 rpm for 20 min at 4° C. The top 26 ml of the gradient were discarded and cells in the next 12 ml were harvested, washed and adjusted to a concentration of $10^4$ cells per ml. Viability of the cells was greater than 90% by as assessed by Trypan blue exclusion, and greater than 80% of the cells contained osmiophilic lamellar bodies typical of Type II cells when examined by electron microscopy.

Adherence assay with mixed and Type II alveolar cells.

About $10^3$ to $10^9$ type II (encapsulated) or R6 (unencapsulated) pneumococci were added to $10^4$ lung cells in a 1 ml volume for 30 min at 37° C. Lung cells were separated from non-adherent bacteria by 6 rounds of washing by centrifugation at 270×g for 5 min. Bacteria adherent to the final cell pellet were enumerated by plating and by Gram stain.

HUVEC and Type II lung alveolar cell adherence assays.

HUVEC (Clonetics, San Diego, Calif.) and Type II alveolar cell line cells (ATCC accession number A549) were cultured 4–8 days and then were transferred to Terasaki dishes 24 hours before the adherence assay was performed to allow formation of a confluent monolayer (Geelen et al., 1993, Infect. Immun. 61:1538–1543). Bacteria were labelled with fluorescein (Geelen et al., supra), and adjusted to a concentration of $5 \times 10^7$, or to concentrations of $10^5$, $10^6$ and $10^7$ cfu per ml, and added in a volume of 5 µl to at least 6 wells. After incubation at 37° C. for 30 min, the plates were washed and fixed with PBS/glutaraldehyde 2.5%. Attached bacteria were enumerated visually using a Nikon Diaphot Inverted Microscope equipped with epifluorescence.

Mutant Strain SPRU25.

An additional mutant strain of R6, SPRU25, was generated as described in Example 1, above.

Results and Discussion

Figure 7:
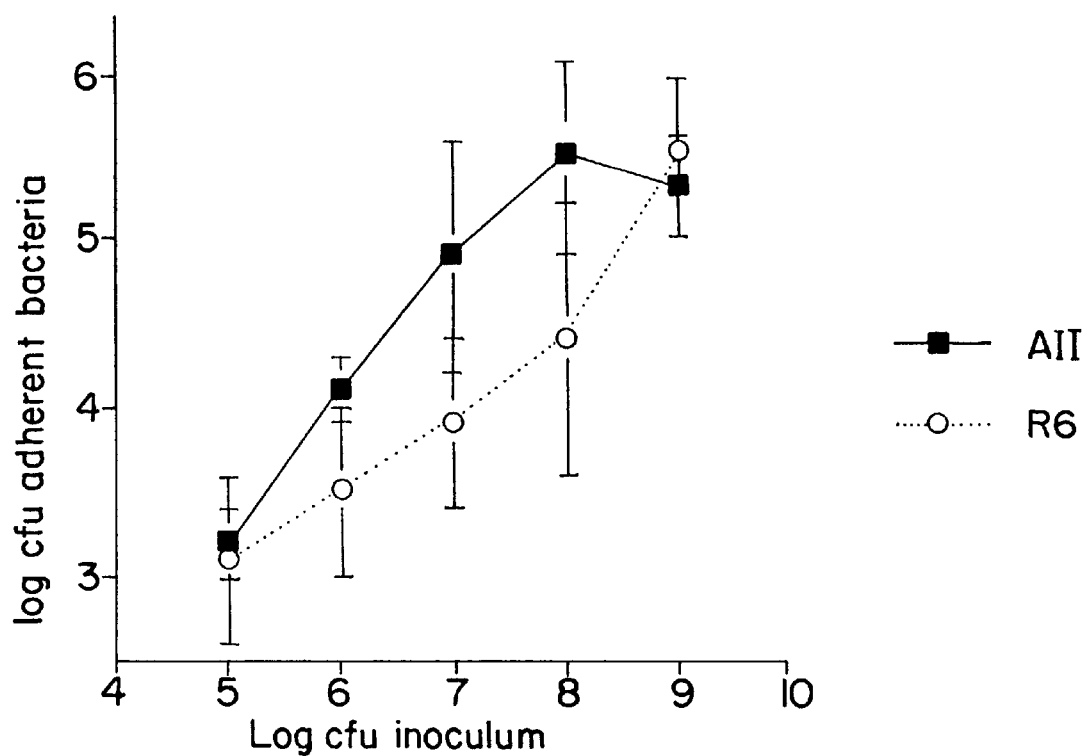
FIG. 7. Adherence of type 2 AII (■) or unencapsulated R6 (○) pneumococci to alveolar Type II cells of rabbit. The adherence assay was performed as described in Example 2, infra.

Adherence of encapsulated type 2 and unencapsulated R6 pneumococci to mixed lung cells (data not shown) was consistently 1–2 logs less at each inoculum than to purified Type II cells. This indicated that Type II cells were the preferred target for the bacteria. The concentration curve for Type II cells is shown in FIG. 7. A consistent but statistically insignificant difference was noted between encapsulated an unencapsulated strains suggesting the type II strain might have a slightly greater ability to adhere than the unencapsulated variant.

Mutant strains (Table 1) were tested for the ability to adhere to HUVEC and lung Type II cells. Strains SPRU98, SPRU42, SPRU40, SPRU25 and SPRU121 were found to have reduced adhesion activity compared to the R6 wildtype strain. The adherence of other strains was not significantly affected by the mutation of exported proteins (data not shown).

Figure 8:
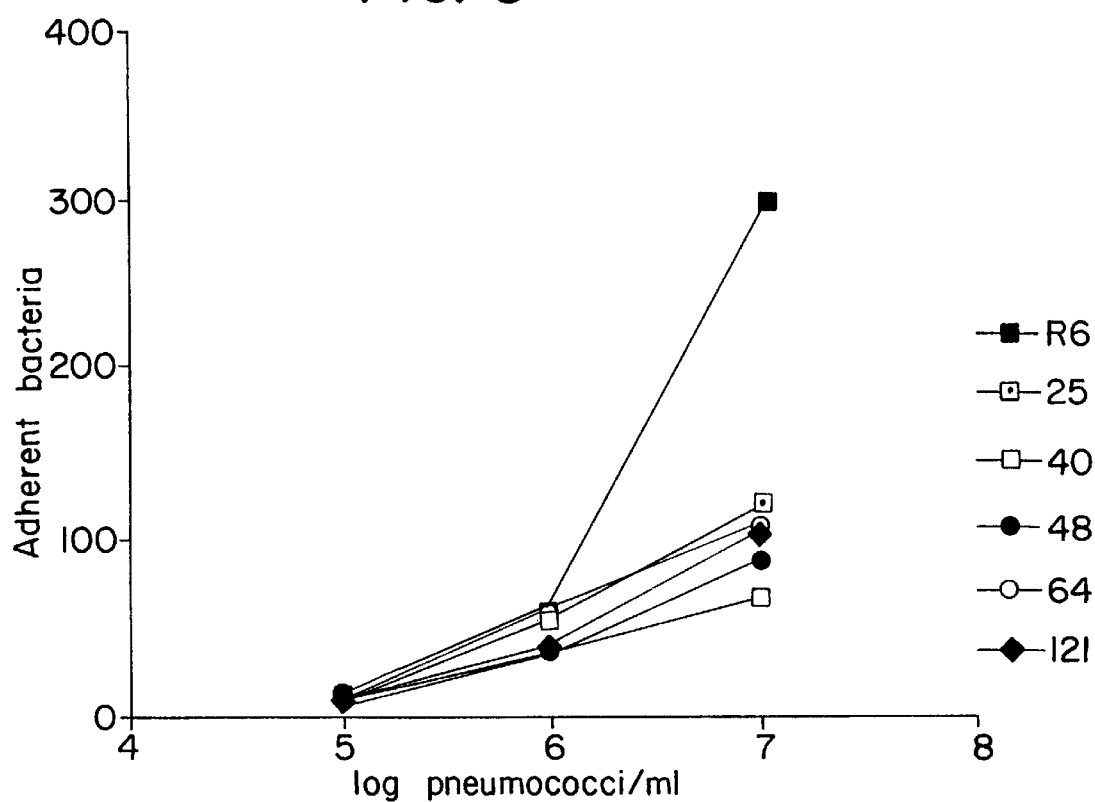
FIG. 8. Titration of the adherence of pneumococcal mutants to human umbilical vein endothelial cells (HUVEC). The mutant strains tested are listed on Table 1. Mutation of exp1, strain SPRU98 (●); exp2, strain SPRU64 (○); exp3, strain SPRU40 (■); exp10, strain SPRU25 (◧); and amiA, strain SPRU121 (♦) resulted in a decrease in the ability of the mutant strain to adhere. Strain R6 (■) is wildtype S. pneumoniae.
Figure 9:
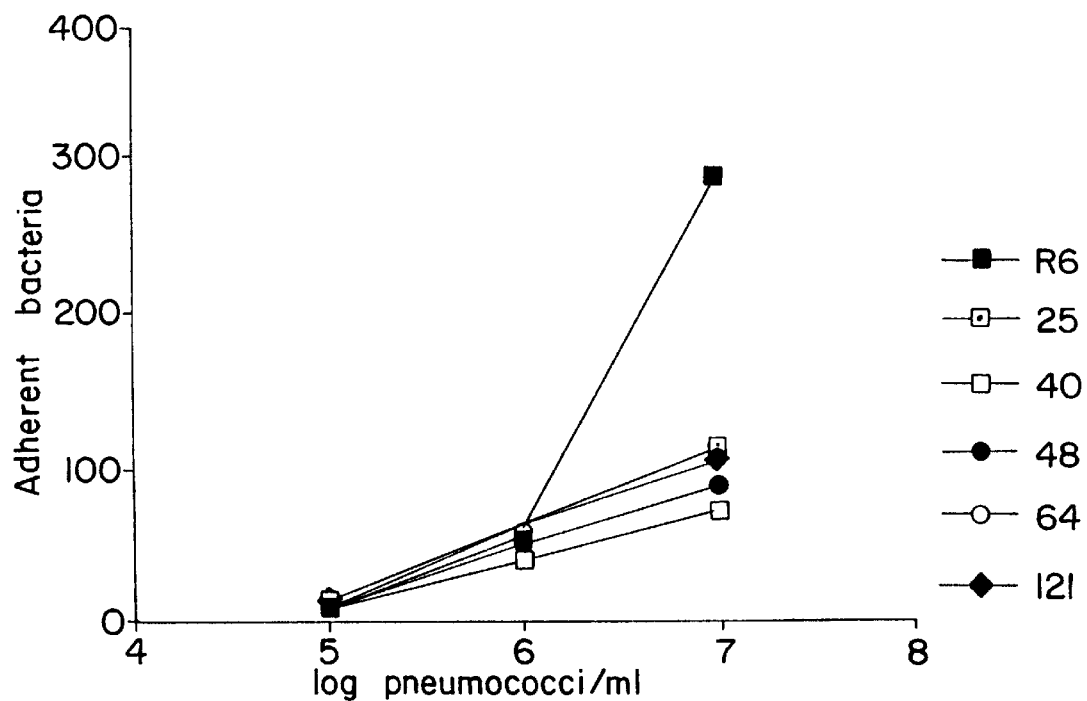
FIG. 9. Adherence of pneumococcal mutants to lung Type II cells. The exported gene mutation and strain designations are as described for FIG. 8.

The bacteria were titrated to $10^5$, $10^6$ and $10^7$ cfu per ml and tested for the ability to adhere to HUVEC (FIG. 8) and lung Type II (FIG. 9) cells. At the lowest concentration, the numbers of adherent bacteria were relatively the same between the adherence deficient mutants and R6. At $10^6$, and more notably at $10^7$, cfu per ml, the difference between binding by the mutants to both HUVEC and lung Type II cells varied from significant to dramatic.

Homologies of the exported proteins of strains SPRU98, SPRU42, and SPRU40 are discussed in Example 1, above. SPRU121 represents a mutation of the amiA locus. The results of this experiment provide unexpected evidence that the AmiA exported protein is involved in adhesion. SPRU25 is a strain generated as described in Example 1, with a mutation at the exp10. No genes or proteins with homology to the nucleic acid [SEQ ID NO:21] or amino acid [SEQ ID NO:22] sequences of this exported protein were found. The identified portion of the exp10 nucleotide and Exp10 amino acid sequences are shown in FIG. 10.

These results clearly indicate that exported proteins of S. pneumoniae that play a role in adhesion of the bacterium to cells can be identified.

EXAMPLE 3

PEPTIDE PERMEASES MODULATE TRANSFORMATION

The present example relates to further elucidation of the sequence and function of Exp1, a mutant that consistently transformed 10 fold less than the parent strain. The complete sequence analysis and reconstitution of the altered locus revealed a gene, renamed plpA (permease like protein), which encodes a putative substrate binding protein belonging to the family of bacterial permeases responsible for peptide transport. The derived amino acid sequence for this gene was 80% similar to AmiA, a peptide binding protein homolog from pneumococcus, and 50% similar over 230 amino acids to Spo0KA which is a regulatory element in the process of transformation and sporulation in Bacillus subtilis. PlpA fusions to alkaline phosphatase (PhoA) were shown to be membrane associated and labeled with [$^3$H] palmitic acid which probably serves as a membrane anchor. Experiments designed to define the roles of the plpA and ami determinants in the process of transformation showed that: 1] Mutants with defects in plpA were >90% transformation deficient while ami mutants exhibited up to a four fold increase in transformation efficiency. 2] Compared to the parental strain, the onset of competence in an ami mutant occurred earlier in logarithmic growth, while the onset was delayed in a plpA mutant. 3] The plpA mutation decreases the expression of a competence regulated locus. Since the permease mutants would fail to bind specific ligands, it seems likely that the substrate-permease interaction modulates the process of transformation.

This example demonstrates through mutational analysis that these two peptide permeases have distinct effects on the induction of competence as well as on transformation efficiency. Therefore, we propose that peptide permeases mediate the process of transformation in pneumococcus through substrate binding and subsequent transport or signaling and that these substrates may be involved in the regulation of competence.

Materials and Methods

Strains and Media. The strains of S. pneumoniae used in this Example are described in Example 1, in particular in Table 1. Table 5 lists other pneumococcal strains used in this study and summarizes their relevant characteristics. Escherichia coli strains used are described in Example 1.

TABLE 5

Bacterial strains of *Streptococcus pneumoniae* used in this study

| Strain | Relevant Characteristics | Integrated plasmid | Source |
| --- | --- | --- | --- |
| R6x | hex−, Parent strain | none | (Tiraby and Fox, 1973) |
| SPRU58 | plpA − phoA fusion | pHplp10 | Current study |
| SPRU98 | plpA − phoA fusion | pHplp1 | (Example 1) |
| SPRU107 | plpA− | pJplp1 | Current study |
| SPRU114 | amiA− | pJamiA1 | Current study |
| SPRU121 | amiA − phoA fusion | pHamiA1 | (Example 1) |
| SPRU122 | plpA− | pJplp9 | Current study |
| SPRU148 | amiC− | pJamiC1 | Current study |
| SPRU100 | exp10 − phoA fusion | | manuscript in preparation |
| SPRU156 | plpA−, exp10 − phoA fusion | pWplp9 | manuscript in preparation |

*S. pneumoniae* plating and culture conditions are described in Example 1. For labeling studies cultures were grown in a chemically defined media ($C_{DEN}$) prepared as described elsewhere (Tomasz, 1964, Bacteriol. Proc. 64:29). *E. coli* were grown in either liquid Luria-Bertani media or on solid TSA media supplemented with 500 μg/ml erythromycin or 100 μg/ml ampicillin where appropriate. For the selection and maintenance of pneumococcus containing chromosomally integrated plasmids, bacteria were grown in the presence of 0.5 μg/ml erythromycin.

PhoA+ libraries and mutagenesis. Libraries of pneumococcal mutants expressing PhoA fusions were created by insertional inactivation with the non replicating pneumococcal *E. coli* shuttle vectors pHRM100 or pHRM104. The pneumococcal *E. coli* shuttle vector pJDC9 was used for gene inactivation without the generation of phoA fusions. The plasmid constructs used for mutagenesis are shown in FIG. 7. The details for these procedures are described in Example 1.

Pneumococcal transformation. To screen large numbers of mutants for a decrease in transformation efficiency, single colonies were transferred to 96 well microtiter plates containing 250 μl of liquid media and chromosomal DNA (final concentration 1 μg/ml) from a streptomycin resistant strain of pneumococcus ($Str^r$ DNA). After incubation for 16 h at 37° C., 5 μl samples were plated onto solid media with and without antibiotic to determine transformation efficiency. Control strains produced approximately $10^5$ $Str^r$ transformants/ml while transformation deficient candidates produced less than $10^4$ $Str^r$ transformants/ml.

The permease mutants were assessed in a more defined transformation assay (FIG. 15). Stock cultures of bacteria were diluted to a cell density of approximately $10^6$ cfu/ml in C+Y media containing $Str^r$ DNA. This solution was dispensed into 250 μl aliquots in a 96 well microtiter plate and the bacteria were grown for 5 hours at 37° C. to an $OD_{620}$ of approximately 0.6. Total bacteria and $Str^r$ transformants were determined by serial dilution of the cultures onto solid media with and without antibiotic. Transformation efficiency was calculated as the percent of $Str^r$ transformants/total number of bacteria and compared to the parent strain, R6x.

Competence profiles which assess transformation were generated from cultures grown in liquid media. Stocks of bacteria were diluted to a cell density of approximately $10^6$ cfu/ml into fresh C+Y media (10 ml) and grown at 37° C. Samples (500 μl) were withdrawn at timed intervals, frozen and stored in 10% glycerol at −70° C. These samples were thawed on ice then incubated with $Str^r$ DNA for 30 min at 30° C. DNAse was added to a final concentration of 10 μg/ml to stop further DNA uptake and the cultures were transferred to 37° C. for an additional 1.5 h to allow the expression of antibiotic resistance. Transformation efficiency was calculated as described above.

Recombinant DNA techniques. Standard DNA techniques including plasmid mini preparations, restriction endonuclease digests, ligations, transformation into *E. coli* and gel electrophoresis were according to standard protocols (Sambrook et al., 1989, supra). Restriction fragments used in cloning experiments were isolated from agarose gels using glass beads (Bio 101) or phenol extractions. Large scale plasmid preparations were prepared using the affinity columns according to the manufacturer's instructions (Qiagen).

Double stranded DNA sequencing was performed by the Sanger method (Sanger et al., 1977, Proc. Natl. Acad. Sci. USA 74:5463–67) using [a-$^{35}$S]-dATP (New England Nuclear) and the Sequenase Version 2.0 kit (United States Biochemical Corp.), according to the manufacturer's instructions. Dimethysulphoxide (1% v/v) was added to the annealing and extension steps.

The polymerase chain reaction (PCR) was performed using the Gene Amp Kit (Perkin Elmer Cetus). Oligonucleotides were synthesized by Oligos Etc. Inc. or at the Protein Sequencing Facility at The Rockefeller University.

In vivo labeling of PlpA-PhoA. Frozen stocks of pneumococcus were resuspended in 4 ml of fresh $C_{DEN}$ media and grown to an $OD_{620}$ of 0.35 at 37° C. Each culture was supplemented with 100 μCi of [9,10-$^3$H] palmitic acid (New England Nuclear) and grown for an additional 30 min. Cells were harvested by centrifugation and washed three times in phosphate buffered saline (PBS). The final cell pellet was resuspended in 50 μl of lysis buffer (PBS; DNAse, 10 μg/ml; RNAse 10 μg/ml; 5% [v/v] deoxycholate) and incubated for 10 min at 37° C. To immuno precipitate the PlpA-PhoA fusion protein the cell lysate was incubated with 20 μl of anti-PhoA antibodies conjugated to Sepharose (5'3' Inc.) for 1 h at 4° C. The suspension was washed three times with equal volumes of PBS and once with 100 μl 50 mM Tris-HCl pH 7.8, 0.5 mM dipotassium ethylenediaminetetra-acetate (EDTA). The final supernatant was discarded and the resin was resuspended in 30 μl of SDS sample buffer, boiled for 5 min and subjected to SDS polyacrylamide gel electrophoresis and autoradiography.

Subcellular fractionation. Pneumococci were fractionated into subcellular components by a previously described technique (Hakenbeck et al., 1986, Antimicrob. Agents Chemother. 30:553–8). Briefly, bacteria were grown in 400 ml of C+Y medium to an $OD_{620}$ of 0.6 and isolated by centrifugation at 17,000 g for 10 min. The cell pellet was resuspended in a total volume of 2 ml of TEPI (25 mM Tris-HCl, pH 8.0, 1 mM EDTA, 1 mM phenyl methyl sulfonyl fluoride, 20 μg/ml leupeptin and 20 μg/ml aprotinin). One half volume of washed glass beads was added and the mixture was vortexed for 15 to 20 min at 4° C. until the cells were broken as documented by microscopic inspection. The suspension was separated from the glass beads by filtration over a cintered glass funnel. The beads were washed with an additional 5 ml of TEPI. The combined solutions were centrifuged for 5 min at 500 g to separate cellular debris from cell wall material, bacterial membranes and the cytoplasmic contents. The supernatant was then spun for 15 min at 29,000 g. The pellet contained the cell wall fraction while the supernatant was subjected to another centrifugation for 2 h at 370,000 g. The supernatant from this procedure contained the cytoplasmic fraction while the pellet contained the bacterial membranes. Samples from each fraction were evaluated for protein content and solubilized in SDS sample buffer for subsequent gel electrophoresis. PlpA-PhoA fusion proteins were detected with anti PhoA antiserum (5'3' Inc.) and visualized indirectly by enhanced chemiluminescence as described in Example 1.

Figure 18:
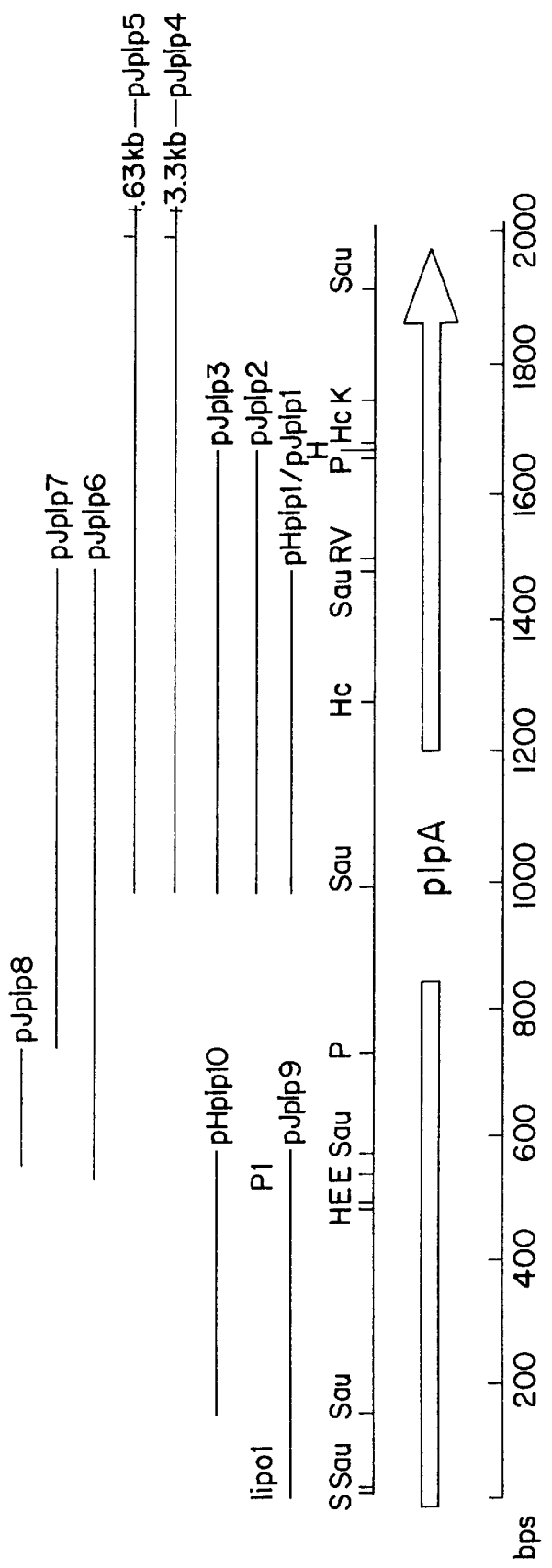
FIG. 18. Physical map of plpA and recombinant plasmids generated from various cloning procedures. Plasmids with the preface pH contain inserts in the PhoA vector pHRM104 while plasmids with the preface pJ contain inserts in the vector pJDC9. Most plasmids were created by "chromosome walking" with the integrated plasmid pJplp1. The plasmid pJplp9 was created by "homology cloning" with the oligonucleotides lipo1 and P1. See experimental procedures for details. Restriction endonuclease sites are shown: H (HindIII), Hc (HincII), E (EcoRI), K (KpnI), P (PstI), R (EcoRV), Sau (SauIIIa), S (SphI).

Recovery and sequencing of plpA. FIG. 18 shows a restriction endonuclease map of plpA and fragments of various subclones. Plasmids with fragments cloned into pHRM104 have the prefix H while those cloned into pJDC9 have the prefix J. The integrated plasmids pHplp1 and pHplp10 were isolated from SPRU98 and SPRU58 respectively by transformation into E. coli of spontaneously excised plasmids which contaminate chromosomal preparations of DNA. "Chromosome walking" was used to isolate most of plpA and the downstream region. The 500 bp insert from pHplp1 was cloned via KpnI into pJDC9 to produce pJplp1 which was shuttled back into pneumococcus to produce SPRU107. Chromosomal DNA from SPRU107 was digested with various restriction endonucleases that cut the vector once but not within the original fragment. The DNA was religated and transformed into E. coli with selection for the vector. Using this procedure PstI produced pJplp2 and HindIII produced pJplp3 which both extended the 3' region of the original fragment in pJplp1 by 190 bp, while SphI produced pJplp4 which contained an additional 3.8 kb. Subcloning of a 900 bp internal fragment of pJplp4 into pJDC9 gave plasmid pJplp5, containing 630 bp downstream from the 3' end of plpA. A further 450 bp was isolated upstream from the original fragment using EcoRI (pJplp6). A 730 bp internal fragment of pJplp6 was cloned into pJDC9 giving pJplp7, and a 200 bp EcoRI/PstI internal fragment of pJplp6 was cloned into the appropriate sites of pJDC9 to produce pJplp8.

The region upstream of the original fragment of plpA was obtained by "homology cloning" using degenerate and specific oligonucleotides with chromosomal DNA in a polymerase chain reaction (PCR). The degenerate oligonucleotide, lipo1, (GCC GGA TCC GGW GTW CTT GCW GCW TGC where W is A+T) (SEQ ID NO: 49) was based on the lipoprotein precursor consensus motif present in AmiA (Alloing et al., 1990, Mol. Microbiol. 4:633–44) and SarA, a peptide permease binding protien homolog from S. gordonii (Jenkinson, 1992, Infect. Immun. 60:1225–8). The specific oligonucleotide, P1, (TAC AAG AGA CTA CTT GGA TCC) (SEQ ID NO: 50) was complimentary to the 5' end of the insert in pJplp6. To prevent amplification of the highly homologous amiA gene, chromosomal DNA was used from SPRU114, which has a disrupted amiA. The chromosomal DNA was first digested with XhoI to give shorter templates. PCR conditions were 40 cycles at 94° C. for 30 seconds for denaturing, 40° C. for 30 seconds for annealing and 72° C. for 1 min for extension. A 600 bp product was obtained, gel purified, digested with BamHI and cloned into Bluescript KS (Stratagene) giving pBSplp9. The BamHI digested fragment was then subcloned into pJDC9 to produce pJplp9. This plasmid was transformed into pneumococcus to give SPRU122.

Generation of a plpA mutant containing a competence regulated gene fused to alkaline phosphatase. The 600 bp BamHI fragment from pBSplp9 was ligated to SauIIIa digested pWG5 (Lacks et al., 1991, gENE 104:11–17) resulting in pWplp9. This plasmid was transformed into SPRU100, which contains a gene, exp10, from the competence regulated rec locus, fused to phoA, giving SPRU156. Correct integration of the vector into the chromosome was confirmed by PCR. Alkaline phosphatase activity was measured as described in Example 1, but with a final substrate concentration (p-nitrophenyl phosphate, Sigma) of 2.5 mg/ml. The activity units were calculated using the following formula:

$$\frac{OD_{420} - 1.75 \times OD_{550}}{\text{time (h)} \times OD_{600} \text{ (of resuspended culture)}}$$

Generation of ami mutants. Internal fragments of ami obtained by PCR and restriction endonuclease digestion were ligated into the appropriate shuttle vectors and transformed into pneumococcus to produce the various ami mutants.

Construction of the gene fusion between amiA and phoA has been previously described in Example 1 to give SPRU121. To obtain a truncated amiA, oligonucleotides ami1 (ACC GGA TCC TGC CAA CAA GCC TAA ATA TTC) (SEQ ID NO: 51) and ami2 (TTT GGA TCC GTT GGT TTA GCA AAA TCG CTT) (SEQ ID NO: 52) were used to generate a 720 bp product at the 5' end of amiA. This fragment was digested with HindIII and EcoRI, which are within the coding region of amiA, and the corresponding 500 bp fragment was cloned into pJDC9. The resulting plasmid pJamiA was transformed into pneumococcus to produce SPRU114. To inactivate amiC, oligonucleotides amiC1 (CTA TAC CTT GGT TCC TCG) (SEQ ID NO: 53) and amiC2 (TTT GGA TTC GGA ATT TCA CGA GTA GC) (SEQ ID NO: 54), which are internal to amiC, were used to generate a 300 bp product using PCR. The resulting fragment was digested with BamHI and cloned into pJDC9 producing the plasmid, pJamiC1, which was transformed into pneumococcus to produce SPRU148.

Northern analysis. RNA was prepared according to procedures adapted from Simpson et al. (1993, FEMS Microbiol. Lett. 108:93–98). Bacteria were grown to an $OD_{620}$ of 0.2 in C+Y media, pH 8.0. After centrifugation (12,000 g, 15 min, 4° C.) the cell pellet was resuspended in 1/40 volume of lysing buffer (0.1% deoxycholate, 8% sucrose, 70 mM dithiothreitol). SDS was added to 0.1% and the suspension incubated at 37° C. for 10 min. Cellular debris was removed and an equal volume of cold 4M lithium chloride was added to the supernatant. The mixed suspension was left on ice overnight then centrifuged at 18,500 g, for 30 min at 4° C. The pellet containing RNA was resuspended in 1.2 ml cold sodium acetate (100 mM, pH 7.0) and 0.5% SDS, extracted three times with an equal volume of phenol/chloroform/isoamyl alcohol (25:24:1) and once with an equal volume of chloroform/isoamyl alcohol (24:1). The RNA was precipitated with ethanol and resuspended in sterile water. The yield and purity was determined by spectrophotometry with a typical yield of 300 µg RNA from 80 ml of culture.

Samples of RNA were separated by electrophoresis in 1.2% agarose/6.6% formaldehyde gels (Rosen and Villa-Komaroff, 1990, Focus 12:23–24). The gel was rinsed in water, and the RNA transferred to nitrocellulose filters (Schleicher and Schuell) by capillary blotting (Sambrook et al., 1989, supra). Prehybridization was for 4 h in 0.2% Denhardts (1× Denhardts is 1% Ficoll, 1% polyvinylpyrrolidone, 1% bovine serum albumin), 0.1% SDS, 3× SSC (1× SSC is 150 mM NaCl, 15 mM sodium citrate), 10 mM HEPES, 18 µg/ml denatured salmon sperm DNA and 10 µg/ml yeast tRNA at 65° C. with gentle agitation. The DNA probe used to detect plpA transcripts was a 480 bp HindIII-BamHI fragment from pJplp9. For detection of amiA transcripts, the DNA probe was a 720 bp PCR product generated with oligonucleotides ami1 and ami2 (described above). The DNA fragments were labeled with [a-$^{32}$P]-dCTP using the Nick Translation System (New England Nuclear). Hybridization was at 65° C. overnight. Hybridization washes were 2× SSC, 0.5% SDS for 30 min at room temperature, followed by 3×30 min washes at 65° C. in 1× SSC, 0.5× SSC and 0.2× SSC, all containing 0.5% SDS.

Results

Figure 12B:
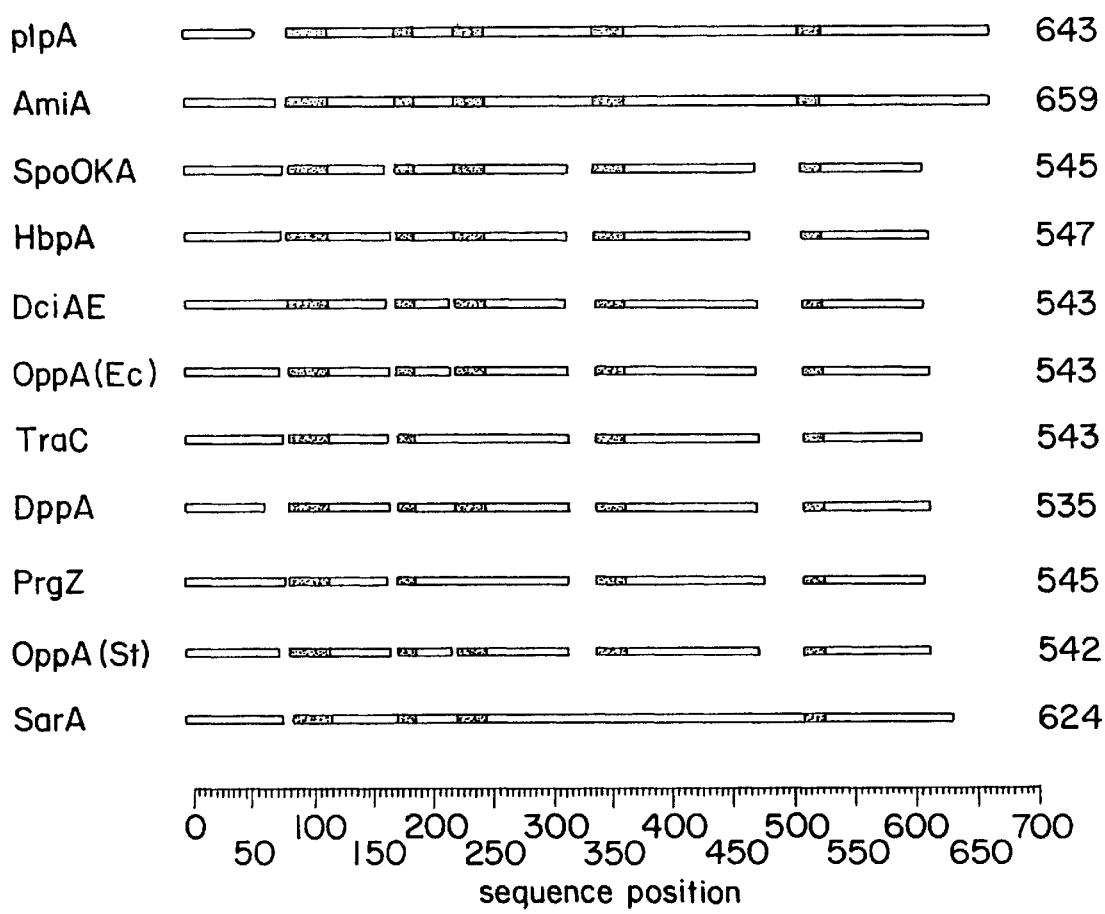
FIG. 12. Sequence analysis of peptide binding proteins. A; Sequence alignment of PlpA and AmiA. Identical residues are boxed. B; Sequence alignments for the substrate binding proteins from the permeases of different bacterial species: PlpA, S. pneumoniae (this study); AmiA, S. pneumoniae. The reported sequence for amiA (Alloing et al., 1990, Mol. Microbiol. 4:633–644) has now been changed due to a sequencing error and the corrected sequence is now in Genbank); Spo0KA, B. subtilis (Perego et al., 1991, Mol. Microbiol. 5:173–185; Rudner et al., 1991, J. Bacteriol. 173:1388–98); HbpA, H. influenzae (Hanson et al., 1992, Infect. Immun. 60:2257–66); DciAE, B. subtilis (Mathiopoulos et al., 1991, Mol. Microbiol. 5:1903–13); OppA (Ec), E. coli (Kashiwagi et al., 1990, J. Biol. Chem. 265:8387–91); TraC, E. faecalis (Tanimoto et al., 1993, J. Bacteriol. 175:5260–64); DppA, E. coli (Abouhamad et al., 1991, Mol. Microbiol. 5:1035–47); PrgZ, E. faecalis (Ruhfel et al., 1993, J. Bacteriol. 175:5253–59); OppA (St) S. typhimurium (Hiles et al., 1987, J. Mol. Biol. 195:125–142) and SarA, S. gordonii. The derived amino acid sequences were aligned with the MACAW software package (Schuler et al., 1993, Proteins Struct. Funct. Genet. 9:180–190). The black boxes and hatched boxes denote regions of high sequence similarity with probability values less than or equal to $1.3 \times 10^{-7}$, with the effective size of the space searched derived from the lengths of all the sequences in the database.

Identification of a transformation deficient mutant with a defect in a peptide permease. To identify exported proteins in mutants as described in Example 1, supra, that participate in the process of transformation, 30 PhoA⁺ mutants were assesed for a decrease in transformation efficiency. In an assay designed to screen large numbers of mutants, transformation of a chromosomal mutation for streptomycin resistance (Str$^r$) into the parental strain (R6x) produced approximately 10⁵ cfu/ml Str$^r$ transformants. The PhoA⁺ mutant, SPRU98 consistently showed a 90% reduction in the number of Str$^r$ transformants (10⁴ cfu/ml). Transformation of the PhoA⁺ mutation into the parent R6x produced strains that were both PhoA⁺ and transformation deficient demonstrating that the mutation caused by the gene fusion was linked to the defect in transformation. The growth rate of SPRU98 was identical to the parental strain suggesting that the transformation deficient phenotype was not due to a pliotropic effect related to the growth of the organism (data not shown). Recovery and identification of the mutated locus in SPRU98 revealed plpA (permease like protein) (FIG. 11, SEQ ID NO:46), which corresponds to exp1. The derived amino acid sequence of plpA (SEQ ID NO: 47) Showed extensive similarity to the substrate binding proteins associated with bacterial permeases (for a review, see Tam and Saier, 1993, Microbiol. Rev. 57:320–346) with the greatest similarity to AmiA (60% sequence identity) (FIG. 12A; SEQ ID NO: 48). Alignment of PlpA with the binding proteins from the family of bacterial peptide permeases revealed several blocks of sequence similarity that suggest functional motifs common to all members of this family (FIG. 12B).

Most examples of peptide permeases have a genetic structure that consists of five genes that encode an exported substrate binding protein, and two integral membrane proteins and two membrane associated proteins that are responsible for substrate transport across the cytoplasmic membrane (for reviews, see Higgins, 1992, Annu. Rev. Cell. Biol. 8:67–113; Tam and Saier, 1993, supra). Sequence analysis 630 bp immediately downstream and in the region 3.3 kb downstream of plpA, did not reveal any coding sequences that are homologs of these transport elements (data not shown). Therefore, if PlpA is coupled to substrate transport, then it may occur through the products of a distinct allele. This is not without precedence. In *Salmonella typhimurium*, the hisJ and argT genes encode the highly similar periplasmic binding proteins J and LAO. Both of these proteins deliver their substrates to the same membrane associated components (Higgins and Ames, 1981, Proc. Natl. Acad. Sci. USA 78:6038–42). Likewise, the periplasmic binding proteins LS-BP and LIV-BP of *Escherichia coli*, which transport leucine and branched chain amino acids, also utilize the same set of membrane-bound components (Landick and Oxender, 1985, J. Biol. Chem. 260:8257–61). We were unable to recover the 5' end of plpA perhaps due to toxicity of the expressed protein in *E. coli*. Similar difficulties have been encountered in cloning the genes of other pneumococcal permeases such as amiA and malX (Alloing et al., 1989, supra; Martin et al., 1989, Gene 80:227–238). Based on sequence similarity between the derived sequences of plpA and amiA all but 51 bp of the 5' end of the gene was cloned.

Membrane localization and post translational covalent modification of PlpA. Both PlpA and AmiA contain the LYZCyz (Y=A, S, V, Q, T: Z=G, A: y=S, T, G, A, N, Q, D, F: z=S, A, N, Q, G, W, E) consensus sequence in the N terminus which is the signature motif for post translational lipid modification of lipoproteins in bacteria (Gilson et al., 1988, EMBO J. 7:3971–74; Yamaguchi et al., 1988, Cell 53:423–32). In gram positive organisms this modification serves to anchor these polypeptides to the cytoplasmic membrane (Gilson et al., 1988, supra). Specific examples of permease substrate binding proteins containing this consensus sequence include SarA from *Streptococcus gordonii* (Jenkinson, 1992, Infect. Immun. 60:1225–8), Spo0KA from *B. subtilis* (Perego et al., 1991, Mol. Micribiol. 5:173–185; Rudner et al., 1991, J. Bacteriol. 173:1388–98), TraC and PrgZ from *E. faecalis* (Ruhfel et al., 1993, J. Bacteriol. 175:5253–59; Tanimoto et al., 1993, J. Bacteriol 175:5260–64) and MalX from *S. pneumoniae* (Gilson et al., 1988, supra).

In support of this proposal, FIG. 13 shows that the PlpA-PhoA protein is exported and associated primarily with the cytoplasmic membranes. Small amounts were also detected in the cell wall fraction and in the culture supernatant suggesting that some of PlpA may be released from the membrane. This is also seen for the peptide binding protein OppA (Spo0KA) from *B. subtilis*, where OppA is initially associated with the cell but increasing proportions are released during growth (Perego et al., 1991, supra). Thus PlpA and OppA may be present on the outside of the cell in a releasable form as has been proposed for other lipoproteins in gram positive bacteria (Nielsen and Lampen, 1982, J. Bacteriol. 152:315–322). Although it cannot be ruled out that the presence of the fusion protein in these fractions does not reflect the location of the native molecule but rather the processing of a foreign protein, this seems unlikely, since other membrane associated PhoA fusions are firmly associated with cytoplasmic membranes.

Finally, a [³H] palmitic acid labeled 93 kDa protein corresponding to the PlpA-PhoA fusion protein was immuno precipitated from SPRU98 which contains a plpA-phoA genetic construct (FIG. 13, lower panel). In contrast, no similarly labeled protein was detected in either the parental control or in SRPU100 which contains an undefined PhoA fusion. This demonstrates in vivo post translational lipid modification of PlpA.

Figure 14:
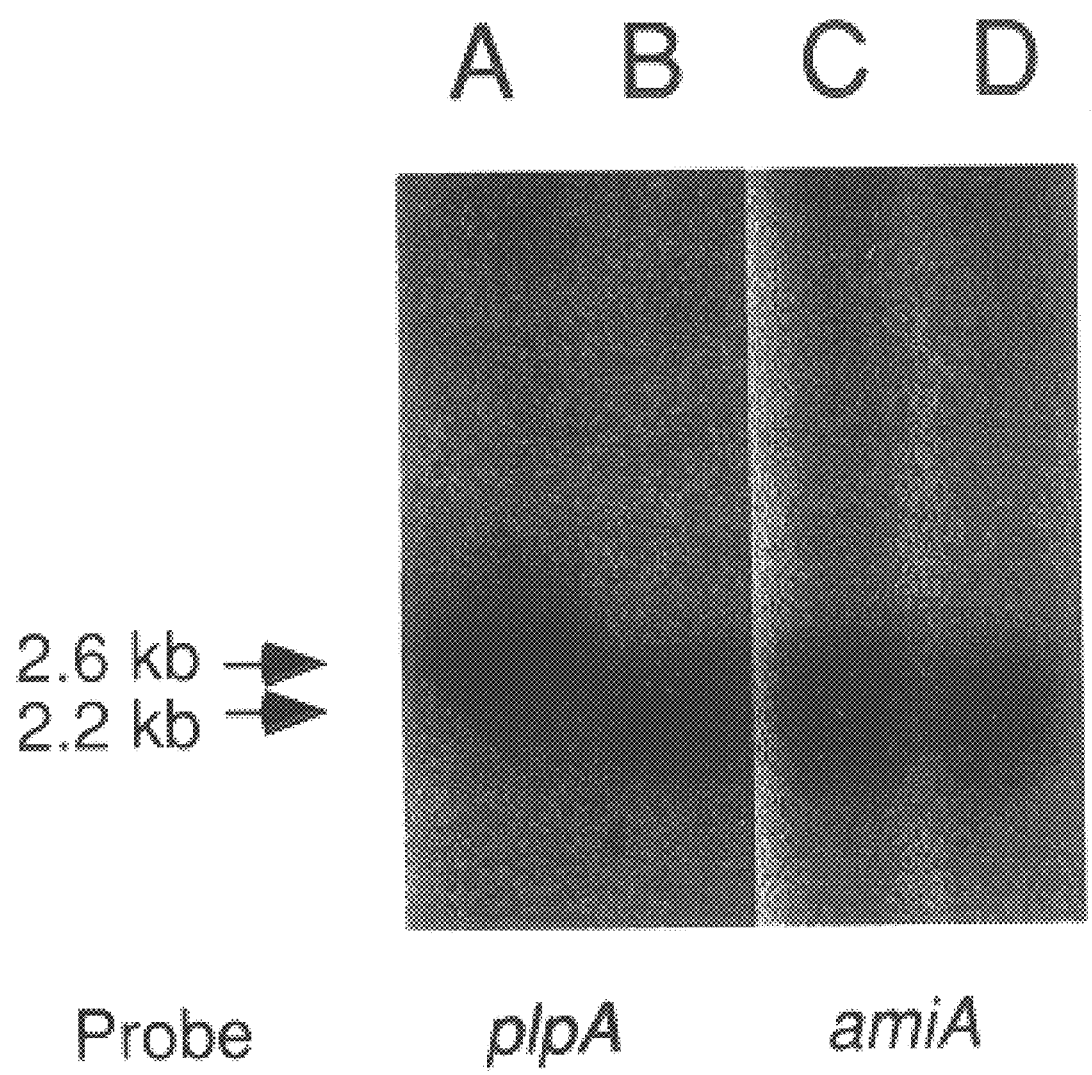
FIG. 14. Northern analysis of pneumococcal peptide permases. RNA (10 μg) prepared from SPRU107 (pJDC9::plpA) (lanes A and C) and R6x (lanes B and D) was hybridized to DNA probes from plpA (lanes A and B) or amiA (lanes C and D). Molecular weights are indicated.

Transcriptional analysis of plpA and amiA. Transcripts of 2.2 kb were detected with probes specific for plpA and amiA in RNA preparations from R6x cells (FIG. 14). This is similar in size to the coding region for both genes. To eliminate the possibility of cross hybridization between the probes for plpA and amiA, high stringency washes were done after hybridization (see experimental procedures). The specificity of the probes was also demonstrated when RNA prepared from the mutant SPRU107, which contains a plasmid insertion in plpA, was probed with amiA and plpA. The amiA transcript remained at 2.2 kb while the plpA transcript shifted to 2.6 kb. In SPRU107, plpA is disrupted at bp 1474 by pJDC9. The plpA transcript would be 520 bp smaller than the full length transcript (1.7 kb), with an additional 800 bp from pJDC9 giving a transcript of about 2.5 kb, which is similar to the 2.6 kb transcript detected.

A single transcript corresponding to the size of plpA suggests that plpA is not part of an operon. This is confirmed by sequence analysis downstream of plpA which did not reveal any homologs to genes encoding transport elements commonly associated with peptide permeases (data not shown). Also, a potential rho independent transcription terminator was identified 21 bp downstream from the translational stop codon of plpA (FIG. 11).

Mutations in the PlpA and AmiA permeases have distinct effects on the process of transformation. To determine the effect of permeases during competence, we assessed the transformation efficiency of mutants with defects in either plpA or ami. In this assay, strains of bacteria were transformed with a selectable marker through a complete competence cycle followed by a subsequent outgrowth and then plated for the selection of the cells which have incorporated the antibiotic marker. Results are thus a measure of the total number of transformed cells during competence. Mutants that produced either truncated or PhoA fusions of PlpA exhibited a two to ten fold decrease in transformation efficiency (FIG. 15). In mutants with a disruption at $Asp_{492}$ of PlpA, the presence (SPRU98) or absence of PhoA (SPRU107), did not affect the 90% decrease in transformation efficiency. On the other hand, a mutant (SPRU122) producing a truncated PlpA at $Asp_{192}$ exhibited a 90% decrease in transformation efficiency, while in SPRU58 the fusion to PhoA at $Leu_{197}$ partially restored the parental phenotype. In this construct it is possible that PhoA conveys functionality by contributing to the chimera's tertiary structure thus affecting its ability to bind its substrate.

In contrast, mutants with defects in ami were transformation proficient. Mutants that produced AmiA truncated at $Pro_{191}$ either in the presence (SPRU121) or absence (SPRU114) of PhoA showed a modest increase in transformation efficiency (FIG. 15). Moreover, mutant SPRU148 with a disruption in AmiC ($Ile_{126}$) showed a four-fold increase in transformation efficiency. In this mutant we presume that AmiA is produced and thus capable of binding its substrate. Therefore, the increase observed with the amiC mutant suggests that substrate transport via the ami encoded transport complex may regulate transformation in addition to substrate binding by AmiA. Finally, even though PlpA and AmiA are highly related structures (60% sequence identity) the disparate effects observed with plpA and ami mutations on transformation efficiency suggest that substrate specificity conveys these differences.

Figure 16:
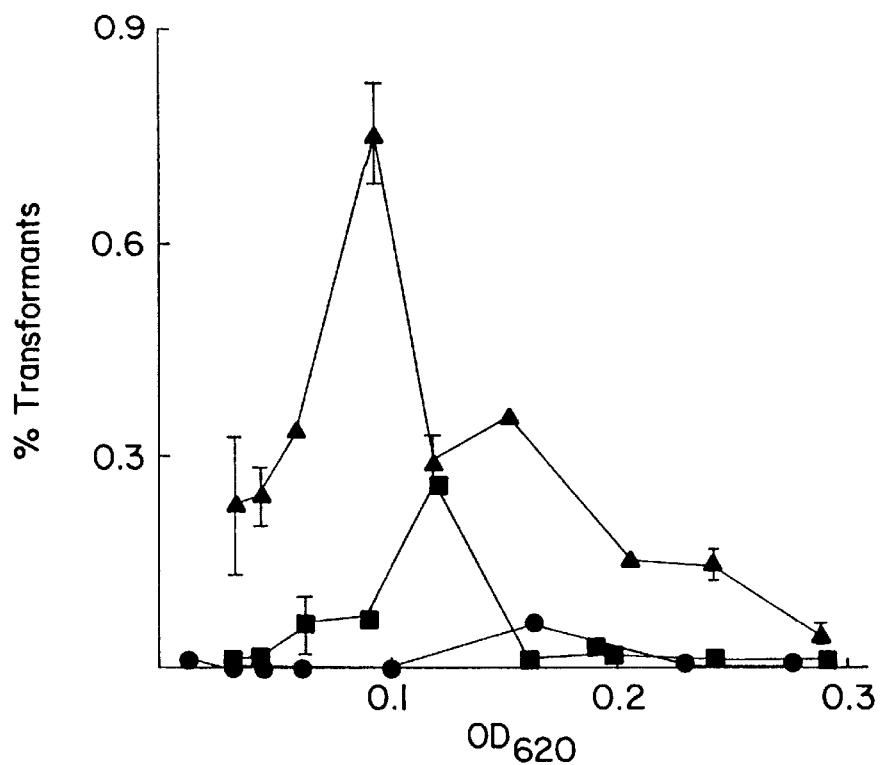
FIG. 16. Competence profiles of pneumococcal permease mutants. The percentage of transformable cells was determined at specific ODs during early logarithmic growth for R6x n, SPRU107 1 (pJDC9::plpA), and SPRU114 s (pJDC9::amiA). The results are representative of three separate experiments.

Transformation occurs during a single wave of competence early in logarithmic growth (FIG. 16). Therefore, regulation of this process may occur by either modifying the onset of competence (a shift in the curve) or by altering the expression of competence induced genes, leading to a change in the number of successfully transformed cells. To determine if the permeases regulate the process of transformation we compared the competence profiles of the permease mutants with the parental strain. This analysis measures the number of transformed cells in the population of cells at various stages of growth during a competence cycle. FIG. 16 shows a single wave of competence for the parental strain (R6x) with a maximal transformation efficiency of 0.26% at an $OD_{620}$ of 0.12. This corresponds to a cell density of approximately $10^7$ cfu/ml. A plpA mutant (SPRU107) underwent a similar wave of transformation with a maximal transformation efficiency of only 0.06% at a higher cell density. In contrast, an amiA mutant (SPRU114) underwent a wave of transformation that persisted over more than one doubling time with a maximal transformation efficiency of 0.75%. The onset of the competence cycle in SPRU114 occurred at an earlier cell density beginning by an $OD_{620}$ of 0.03. From this data we conclude that mutations in either permease has a dual effect on the process of transformation, affecting both the induction of the competence cycle as well as modulating the successful number of transformants.

Figure 17:
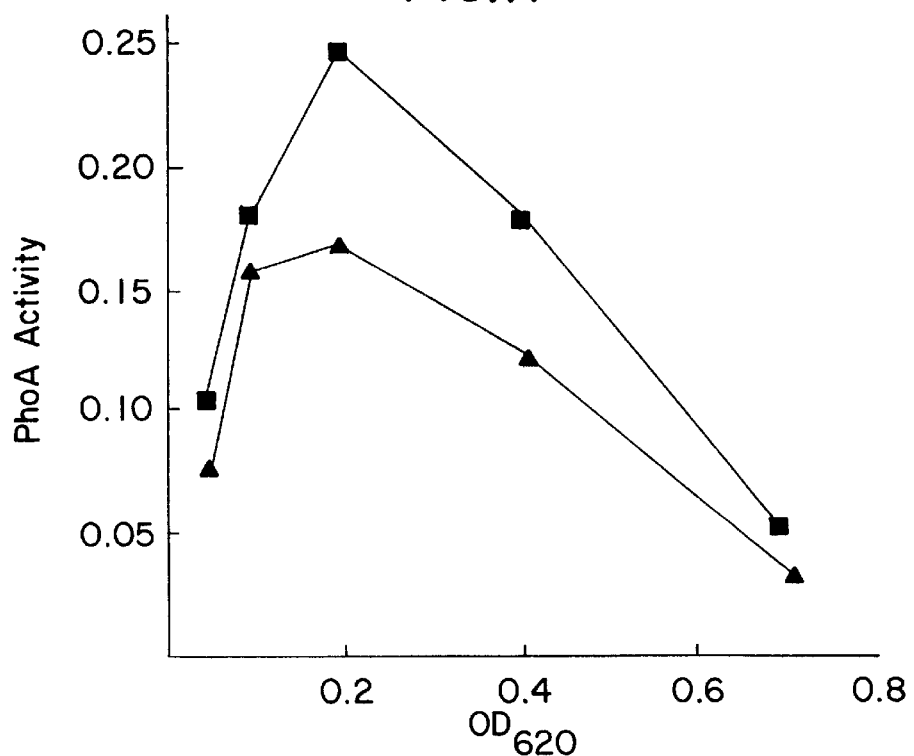
FIG. 17. Effect of a mutation in plpA on the expression of the competence regulated rec locus. Alkaline phosphatase activity was measured for SPRU100, n (PhoA$^+$, pHRM104::exp10) and SPRU156, s (PhoA$^+$, pHRM104::exp10; pWG5::plpA) during logarithmic growth of pneumococcus which produces a normal competence cycle. Each value is the average of two data points with a standard error of the mean that did not exceed 10% of that point. These results are representative of three independent experiments.

A mutation in plpA causes a decrease in the expression of a competence regulated locus. The rec locus in pneumococcus, which is required for genetic transformation, contains two genes, exp10 and recA. Results with a translational exp10-phoA gene fusion have demonstrated a 10 fold increase in enzyme activity with the induction of competence demonstrating that this is a competence regulated locus. To determine if the peptide permeases directly affect the expression of this competence induced locus, we constructed a mutant (SPRU156) with a null mutation in plpA and the exp10-phoA gene fusion. By measuring alkaline phosphatase activity during growth, we showed that compared to an isogenic strain (SPRU100), the mutant harboring the plpA mutation demonstrated almost a two fold decrease in the expression of the exp10-phoA fusion (FIG. 17). Therefore, these results show that at least plpA directly affects the signaling cascade responsible for the expression of a competence regulated gene required for transformation.

Discussion

The newly identified export protein Exp1, is encoded by the genetic determinant, renamed herein plpA. This locus, along with the ami locus, modulates the process of transformation in S. pneumoniae. Both loci encode highly similar peptide binding proteins (PlpA, AmiA) that are members of a growing family of bacterial penneases responsible for the transport of small peptides (FIG. 11b). Examples of these peptide binding proteins have been associated with the process of genetic transfer in several bacteria. In B. subtilis, inactivation of spo0KA, the first gene of an operon with components homologous to the peptide permeases, caused a decrease in transformation efficiency as well as arresting sporulation (Perego et al., 1991, supra; Rudner et al., 1991, supra). The substrate for Spo0KA is not known. B. subtilis produces at least one extracellular differentiation factor that is required for sporulation (Grossman and Losick, 1988, supra) and it has been proposed that this transport system could be involved in sensing this extracellular peptide factor which may be required for competence and sporulation.

Conjugal transfer of a number of plasmids in E. faecalis is controlled by small extracellular peptide pheromones. Recent genetic analyses have identified two plasmid encoded genes, prgZ and traC, whose derived products are homologous to the peptide binding proteins. Experimental evidence suggests that these proteins may bind the peptide pheromones thus mediating the signal that controls conjugation (Ruhfel et al., 1993, supra; Tanimoto et al., 1993, supra). The absence of membrane transport elements is a common feature between the prgZ, traC and plpA determinants which implies either that transport is not required for signal transduction or that a distinct allele is required for transport.

Mutations in plpA and ami cause a decrease or an increase in transformation efficiency, respectively. In addition, mutations in these loci affect the induction of the growth stage specific competent state. Compared to the parent strain, a mutation in ami induces an earlier onset of competence while a mutation in plpA delays this induction. Furthermore, a translational fusion to a competence regulated locus has shown that a mutation in plpA directly affects the expression of a gene required for the process of transformation. Given that the induction of competence occurs as a function of cell density (Tomasz, 1966, J. Bacteriol. 91:1050–61), it is reasonable to propose that these permeases serve as regulatory elements that modulate the cell density dependent induction of competence by mediating the binding and or transport of signaling molecules. Small peptides which are the presumed substrates for permeases in other bacteria or the extracellular pneumococcal activator protein are likely candidates as ligands for these permeases. Because peptide permease defective mutants of *Salmonella typhimurium* and *Escherichia coli* fail to recycle cell wall peptides released into culture media, it has been proposed that these permeases bind and transport cell wall peptides (Goodell and Higgins, 1987, J. Bacteriol. 169:3861–65; Park, 1993, J. Bacteriol. 175:7–11). Thus, cell wall peptides are likely candidates. Recent genetic evidence suggests that divalent cation ($Ni^{2+}$) transport is also coupled to peptide permease function in *E. coli* (Navarro et al., 1993, Mol. Microbiol. 9:1181–91). It has also been shown that extracellular $Ca^{2+}$ coupled to intracellular transport can affect transformation (Trombe, 1993, J. Gen. Microbiol. 139:433–439; Trombe et al., 1992, J. Gen. Microbiol. 138:77–84). Therefore, peptide permease mediated divalent cation transport is also a viable model for intracellular signaling and subsequent modulation of transformation.

EXAMPLE 4

A PYRUVATE OXIDASE HOMOLOG REGULATES ADHERENCE

The present Example describes isolation and sequence determination of an Exp mutant that encodes a pyruvate oxidase homolog. This new protein rates bacterial adherence to eucaryotic cells.

Bacterial adhesion to epithelial cells of the nasopharynx is recognized as a requirement for colonization of the mucosal surface and infection. Pneumococcal cell wall and proteins of the bacterial surface mediate attachment to eukaryotic cells. The molecular determinants that pneumococcus recognizes on the surface of the eucaryotic cell are complex sugars, particularly GlcNAcβ1-3Gal or GalNAcβ1-4Gal carbohydrate moieties.

Mutants, as described in Example 1, supra, were screened for loss of binding to type II lung cells (T2LC), human endothial cells (HUVEC), and to GlcNAcβ1-3Gal sugar receptors in a hemagglutination assay that reflects adherence to cells in the nasopharynx.

One out of 92 independent mutants, named Pad1 (pneumococcal adherence 1), exhibited an inability to hemagglutinate the GlcNAcβ1-3Gal sugar receptor on neuraminidase-treated bovine erythrocytes as described (Andersson et al., see Example 2). Hemagglutination of neuraminidase treated bovine erythrocytes reflects adherence to cells in the nasopharynx. Directed mutagenesis of the parent strain inactivating pad1 reconfirmed that the loss of hemagglutination was linked to this locus.

Figure 19A:
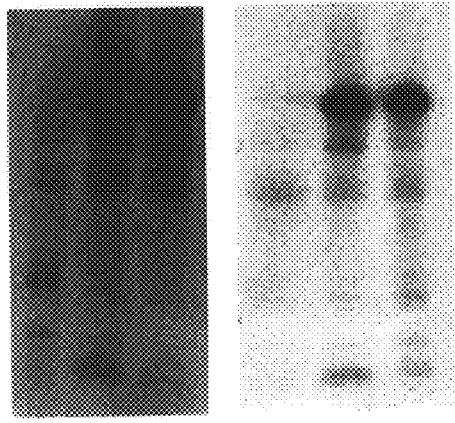
FIG. 19. Adherence of R6 wild-type (□) and Pad1 mutant (■) pneumococci to type II lung cells. This assay was performed as described in Example 2.
Figure 19B:
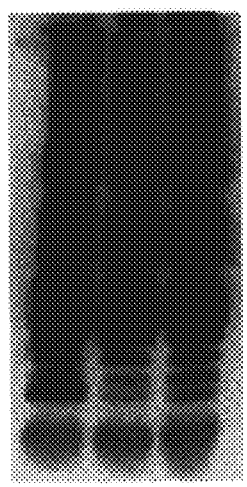

This mutant also exhibited a greater than 70% decrease in adhesion to T2LCs and HUVECs, as shown in FIG. 19.

Recovery and reconstitution of the mutated locus pad1 revealed an open reading frame of 1.8 kb with sequence similarity to enzymes in the acetohydroxy acid synthase-pyruvate oxidase family. In particular, pad1 shares 51% sequence similarity with recombinant pox, and 32% similarity with poxB. Targeted genetic disruption of the locus in the parent strain showed that mutation at this locus was responsible for the loss of adherence in all three assays.

Figure 20:
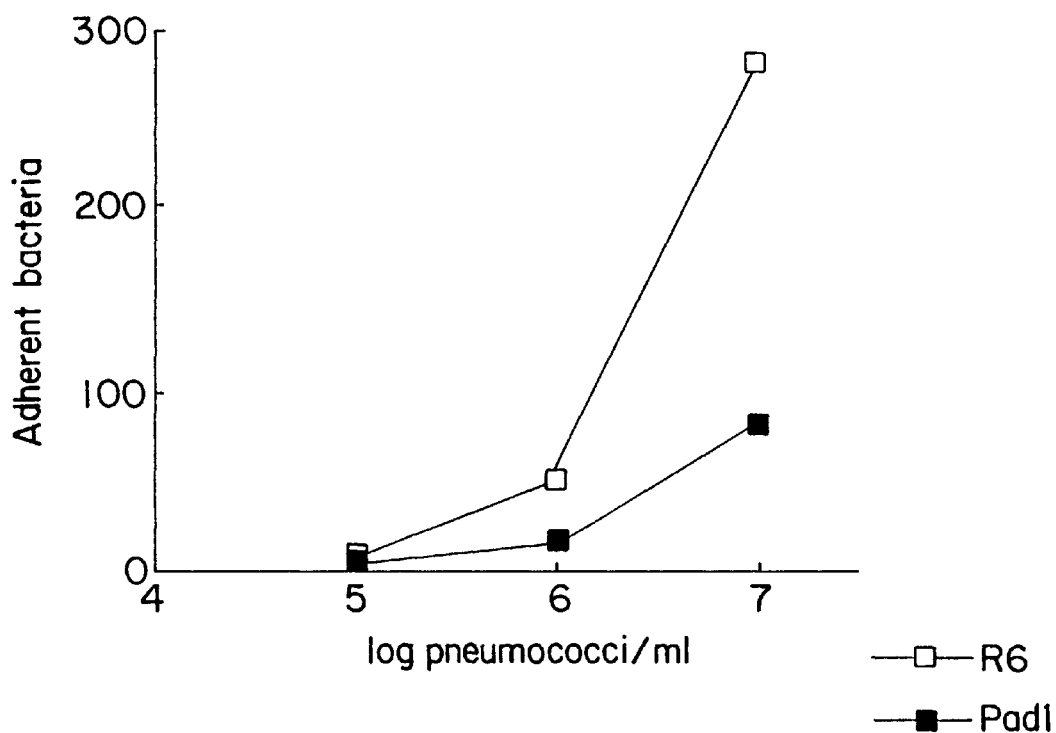
FIG. 20. (A) Subcellular localization of Pad1-PhoA fusion detected by Western analysis with anti-PhoA antisera., The cells were separated into the membrane components (Lanes A–C) and cytoplasmic components (Lanes D–F). Lanes A,D—R6 wild-type (parent) cells; B,E—Pad1 mutant cells; C,F—Pad1b mutant cells. (B) Probe of bacterial lysate with antibody to whole bacteria by Western analysis. Lanes A, B and C correspond to (A). The Pad1 mutants lack a 17 kDa immunogenic membrane associated protein found in the R6 bacteria.

Subcellular fractionation of a mutant that expressed a Pad1-PhoA fusion showed that the protein localized to the membrane and the cytoplasm (FIG. 20A). Comparison of antigenic surface components in the parent and mutant strain showed that loss of a 17 kDa polypeptide that did not correspond to Pad1 (FIG. 20B).

These results indicate that Pad1 affects pneumococcal adherence to multiple cell types, possibly by regulating the expression of bacterial adhesins.

Figure 21:
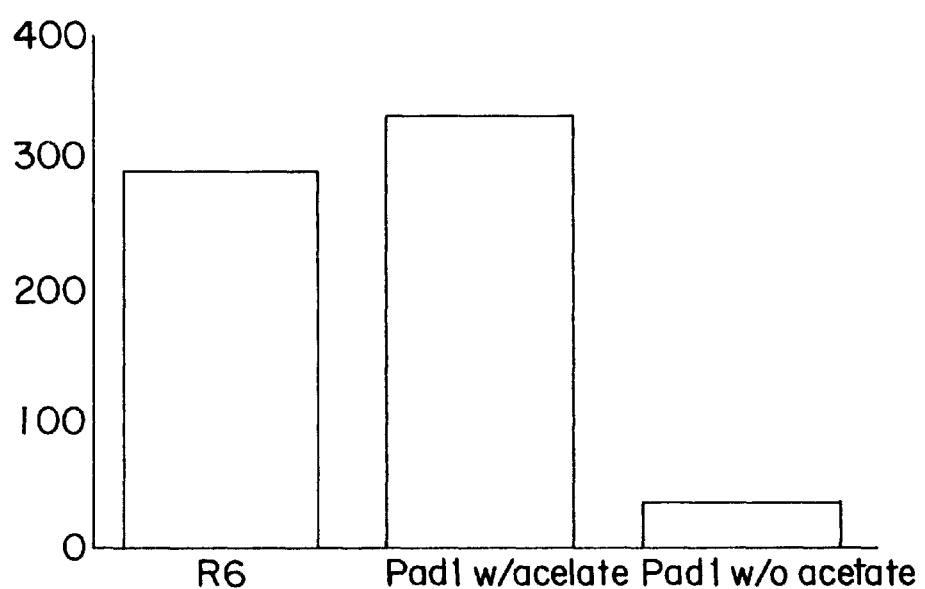
FIG. 21. Adherence of R6 bacteria and Pad1 mutants grown in the presence and absence of acetate. Growth in acetate corrects the Pad1 adherence defect.
Figure 22:
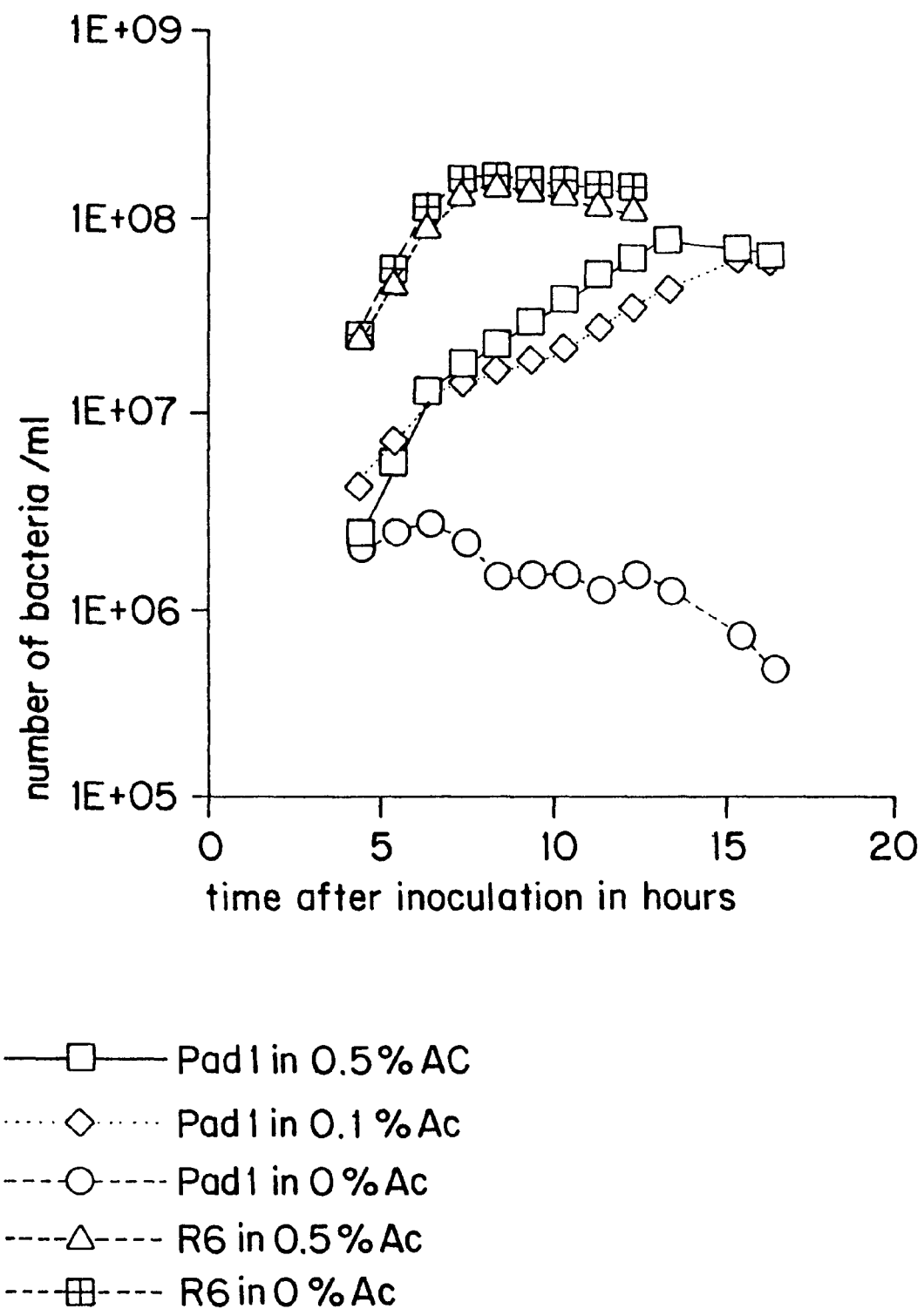
FIG. 22. Growth of the Pad1 mutant and R6 bacteria in the presence or absence of acetate. The Pad1 mutant was grown in chhemically defined growth medium for S. pneumodiae in the presence of 0% (○), 0.1% (◇) and 0.5% (□) acetate. R6 was grown in the presence of 0% (square plus) and 0.5% (△).

The Pad1 mutant required acetate for growth in a chemically defined media (FIGS. 21 and 22). Growth in acetate restored the adhesion properties of the bacteria to both lung and endothelial cells.

The nucleotide sequence information for the pad1 promoter region shows a putative −35 site, a −10 taatat sequence, a ribosome binding site, and a translation start site (FIG. 23A) (SEQ ID NO: 55). The deduced protein translation of this region is also provided (FIG. 23B) (SEQ ID NO: 56). The nucleotide coding sequence and deduced amino acid sequence of Pad1 are shown in FIGS. 23C (SEQ ID NO: 57) and 23D (SEQ ID NO: 58), respectively.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

It is also to be understood that all base pair sizes given for nucleotides and all molecular weight information for proteins are approximate and are used for the purpose of description.

Various references are cited throughout this specification, each of which is incorporated herein by reference in its entirety.

What is claimed is:

1. An isolated polypeptide comprising the amino acid sequence of SEQ ID: NO 56.

2. An isolated polypeptide comprising the amino acid sequence of SEQ ID NO: 58 (FIG. 23D).

* * * * *